(12) United States Patent
Dimitroff et al.

(10) Patent No.: US 11,858,998 B2
(45) Date of Patent: Jan. 2, 2024

(54) GLYCOME FACTORS DRIVING MELANOMA PROGRESSION

(71) Applicants: Charles J. Dimitroff, Coral Gables, FL (US); Asmi Chakraborty, Boston, MA (US)

(72) Inventors: Charles J. Dimitroff, Coral Gables, FL (US); Asmi Chakraborty, Boston, MA (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/101,285

(22) Filed: Jan. 25, 2023

(65) Prior Publication Data

US 2023/0235066 A1 Jul. 27, 2023

Related U.S. Application Data

(60) Provisional application No. 63/303,325, filed on Jan. 26, 2022.

(51) Int. Cl.
*C07K 16/28* (2006.01)
*A61P 35/00* (2006.01)

(52) U.S. Cl.
CPC .......... *C07K 16/2851* (2013.01); *A61P 35/00* (2018.01)

(58) Field of Classification Search
CPC ............ C07K 2317/76; C07K 16/2851; A61K 48/005; A61P 35/00
See application file for complete search history.

(56) References Cited

U.S. PATENT DOCUMENTS

2003/0050266 A1* 3/2003 Fisher .................... A61K 38/19
435/320.1

FOREIGN PATENT DOCUMENTS

WO   WO-2015200601 A2 * 12/2015   ........... A61K 31/702

OTHER PUBLICATIONS

Keizer et al (Clinical Pharmacokinetics, 2010, vol. 49, pp. 493-507) (Year: 2010).*
Ballarin-Gonzalez et al (Molecular Therapy-Nucleic Acids, 2013, vol. 2, e76) (Year: 2013).*
Wu et al, RSC Adv., 2020, vol. 10, pp. 19636-19642 (Year: 2020).*
Pal et al, Org. Biomol. Chem, vol. 16, pp. 6295-6305 (Year: 2018).*
Kamposioras et al (Critical Reviews in Oncology/Hematology, 2011, vol. 78, pp. 112-126) (Year: 2011).*
Siu et alt (Biomaterials, 2014, vol. 35, pp. 3435-3442) (Year: 2014).*
Dobrowlski et al (Adv. Healthcare Mater., 2021, vol. 10, 16 pages) (Year: 2021).*
Hu et al (Signa Transduction and Targeted Therapy, 2020, vol. 5, 25 pages) (Year: 2020).*
Mumprecht and Detmar (Journal of Molecular Medicine, 2009, vol. 13, No. 8A, pp. 1405-1416) (Year: 2009).*
Bartlett and Karakousis (Surg Oncol Clin N Am, 2015, vol. 24, pp. 215-227) (Year: 2015).*
Bidon-Wagner and LePennec, Glycoconjugate Journal, 2004, vol. 19, pp. 557-563 (Year: 2004).*
Chakraborty, Asmi et al. "Hypoxia Controls the Glycome Signature and Galectin-8-Ligand Axis to Promote Protumorigenic Properties of Metastatic Melanoma." Journal of Investigative Dermatology, in press, (Year: 2022).

* cited by examiner

*Primary Examiner* — Karen A. Canella
(74) *Attorney, Agent, or Firm* — SALIWANCHIK, LLOYD & EISENSCHENK

(57) ABSTRACT

The present invention provides methods for diagnosis, prognosis, prevention and/or treatment of cancers such as melanomas. The subject invention provides biomarkers and methods for assessing the severity of a cancer/tumor and for monitoring the progressing of a cancer/tumor. The subject invention also provides therapeutic targets in cancer for developing anti-cancer therapies.

18 Claims, 33 Drawing Sheets

Specification includes a Sequence Listing.

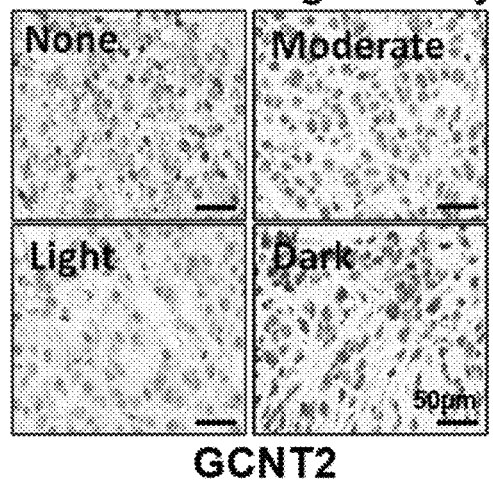
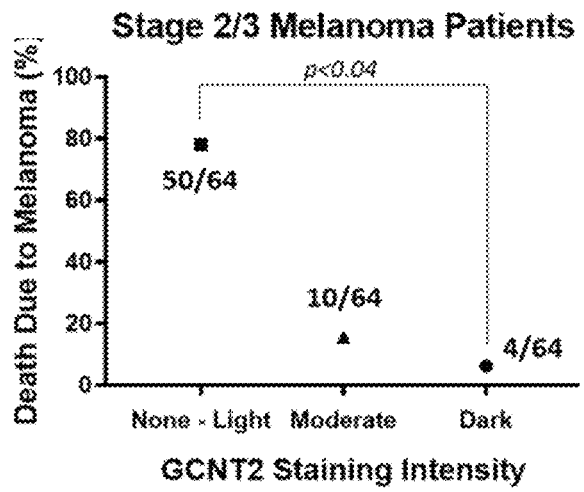
FIG. 1A
FIG. 1B
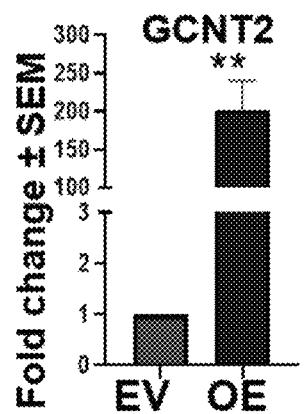
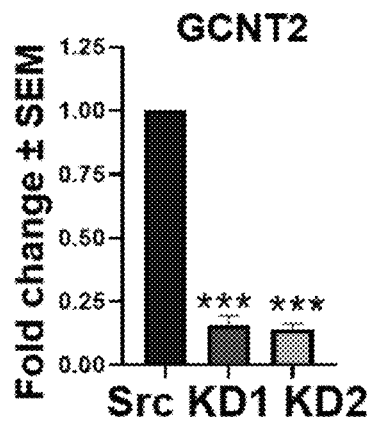
FIG. 1C
FIG. 1D

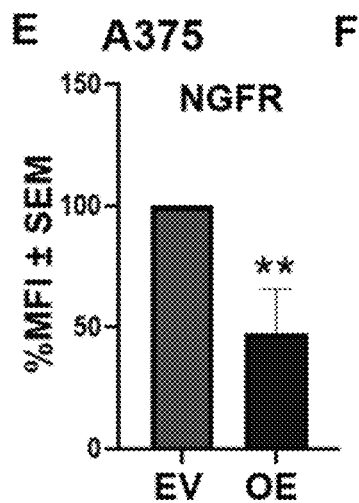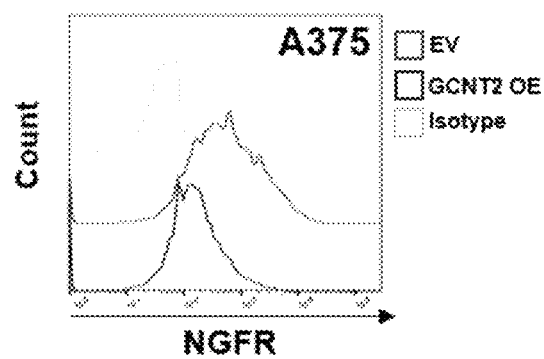
FIG. 1E  FIG. 1F
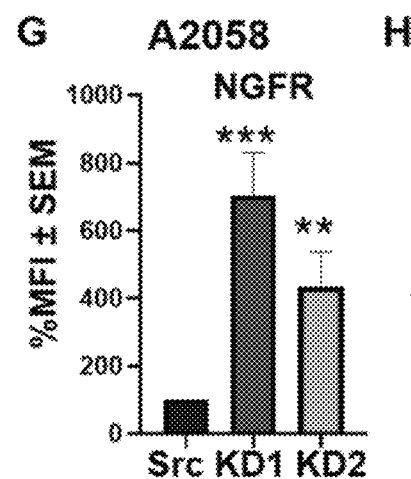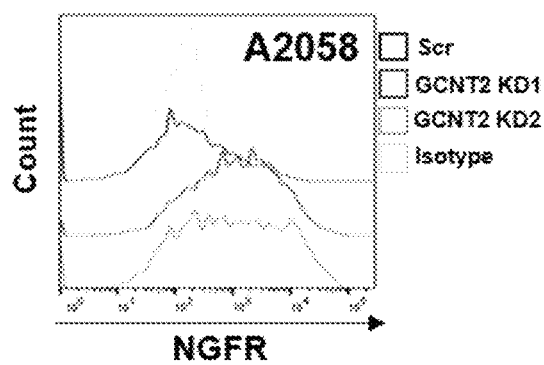
FIG. 1G  FIG. 1H

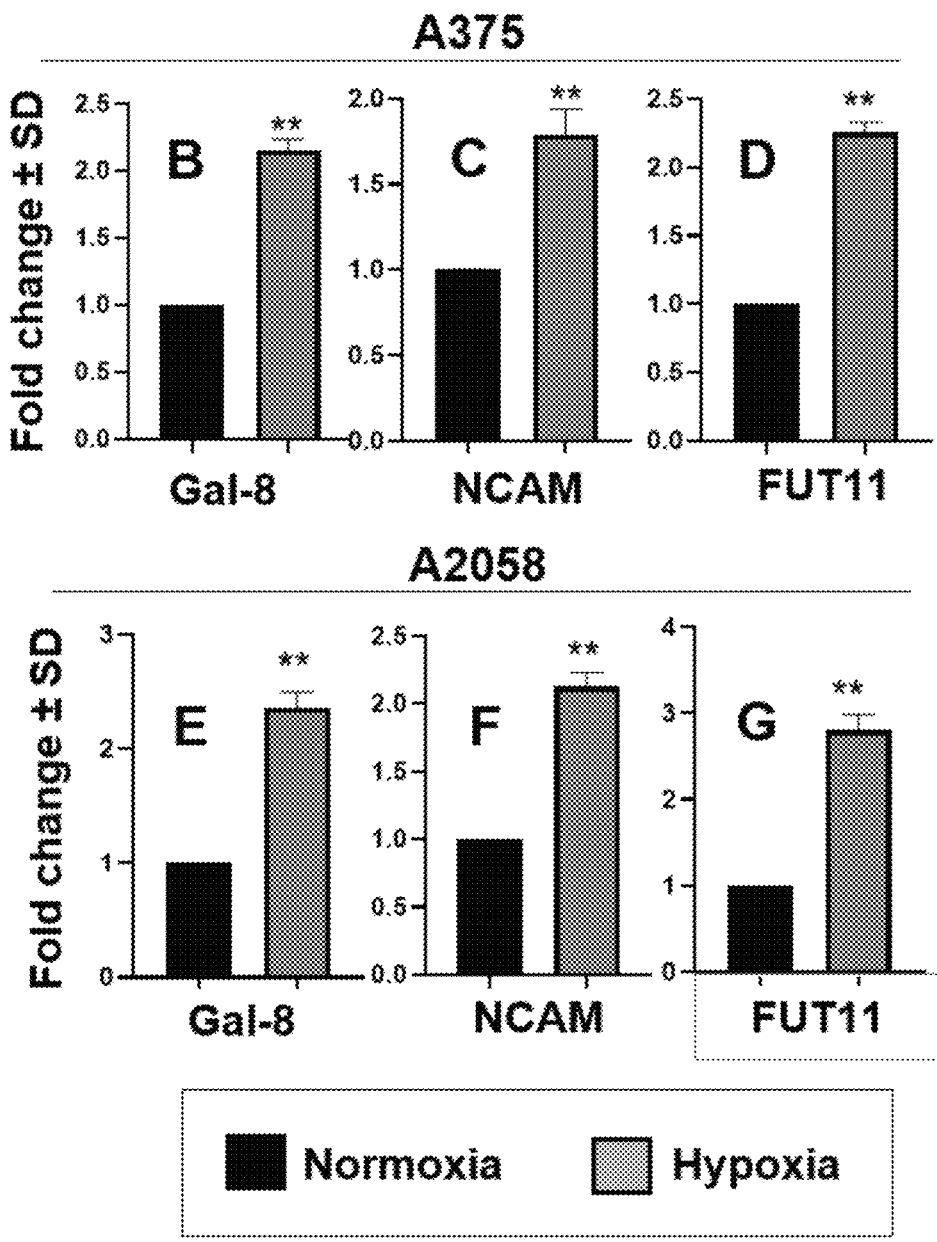

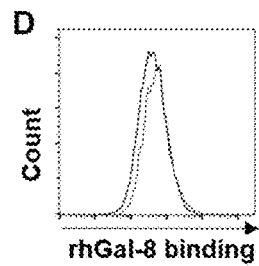
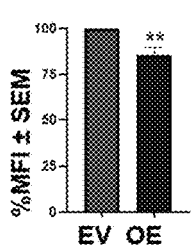
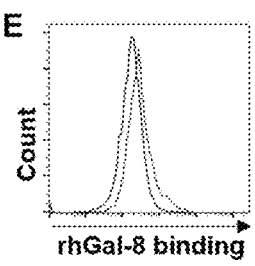
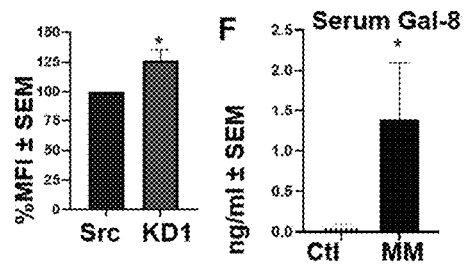
FIG. 6D  FIG. 6E  FIG. 6F
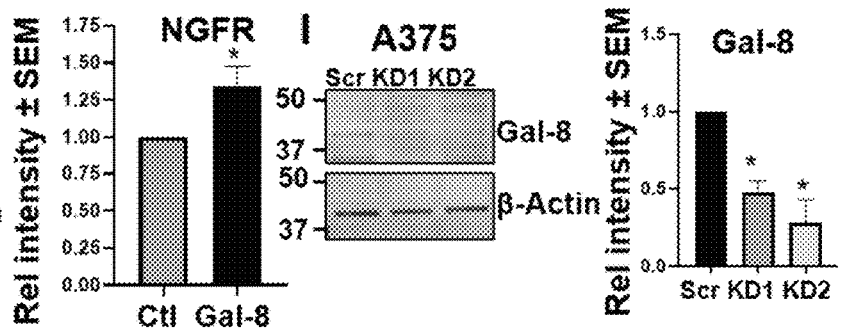
FIG. 6G  FIG. 6I
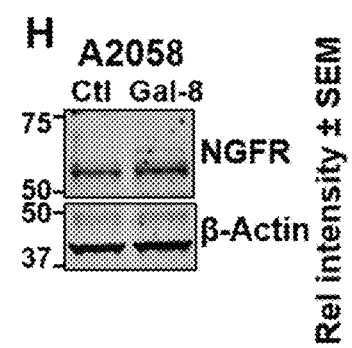
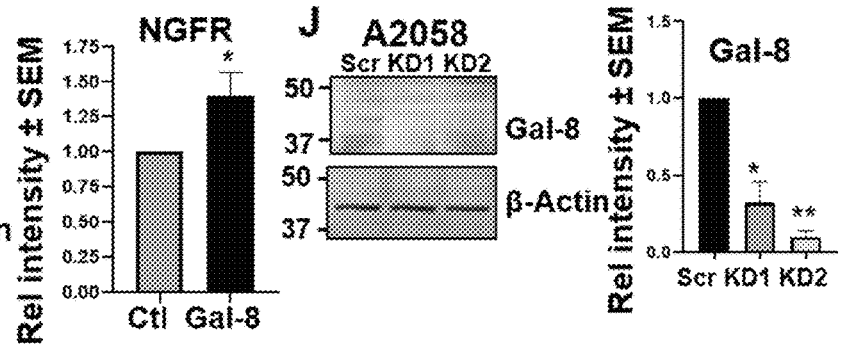
FIG. 6H  FIG. 6J

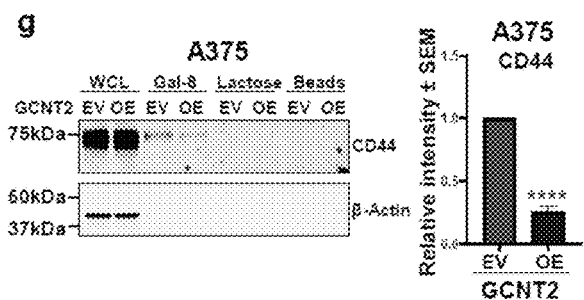
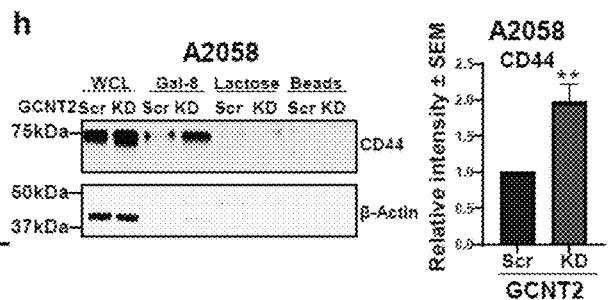
FIG. 7G
FIG. 7H
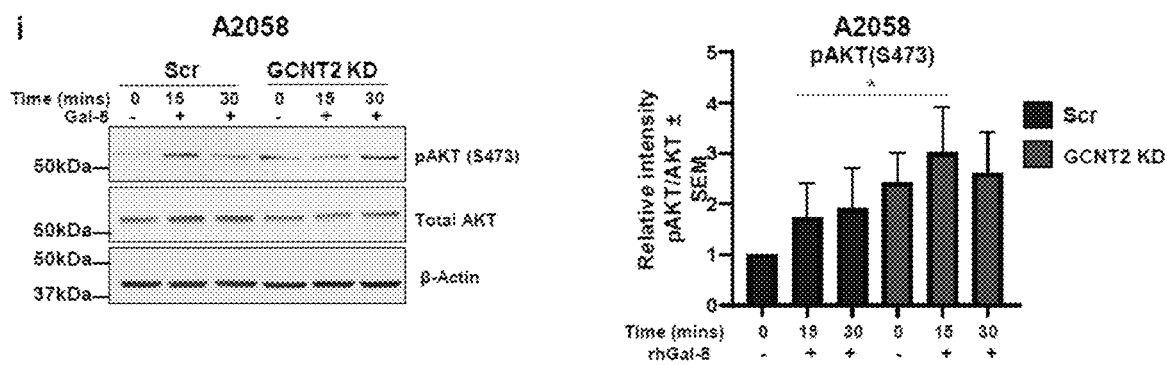
FIG. 7I

GLYCOME FACTORS DRIVING MELANOMA PROGRESSION

CROSS-REFERENCE TO RELATED APPLICATION

This application claims the benefit of U.S. Provisional Application Ser. No. 63/303,325 filed Jan. 26, 2022, which is hereby incorporated by reference herein in its entirety.

GOVERNMENT SUPPORT

This invention was made with government support under CA225644 awarded by The National Institutes of Health. The government has certain rights in the invention.

SEQUENCE LISTING

The Sequence Listing for this application is labeled "SeqList-18Jan23.xml," which was created on Jan. 18, 2023, and is 13,643 bytes. The Sequence Listing is incorporated herein by reference in its entirety.

BACKGROUND

While a diagnosis of metastatic melanoma (MM) at distant sites portends a grim prognosis, recent advances in immune checkpoint inhibition (ICI) therapy have led to promising and more durable responses. However, the 5-year survival rate is still only ~37%. Many MMs have adapted to retain their malignant behavior and evade these therapies. Thus, there is a growing need for predictive biomarkers of therapeutic response and the potential synergistic effects of other anti-melanoma therapeutics.

While various genetic alterations and related neoantigen evolution have dominated research investigations, glycosylation alterations associated with melanoma progression have received little attention. Glycosylation, one of the most common post-translational modifications, entails the addition of sugar chains, known as glycans, to proteins to modulate their function. Essentially all cell surface proteins contain N- and/or O-glycans built on asparagine or serine/threonine residues, respectively; so protein glycosylations are likely closely related to MM activity. While glycans enforce biomolecular function, their roles as binding moieties to glycan-binding proteins, or lectins, in cancer progression pathways is not fully understood.

β-galactoside-binding lectins, or galectins, are S-type lectins that have both microenvironmental and intracellular functions in normal immune, stromal, and parenchymal tissues and in cancer. There are 15 known galectins in humans. Intracellular function of galectins ranges from pre-mRNA splicing, and pro- and anti-apoptosis via protein-protein interactions and regulation of autophagy. They lack a canonical signal secretion sequence and are routed to the extracellular surface in non-classical secretion pathways. In the extracellular milieu, galectin (Gal)-1, -3 and -9, are known to bind cell surface glycans and alter cellular signaling activities that control proliferation, death, migration, and other effector functions depending on a given cell type. Identified as a tandem-repeat lectin with 2 carbohydrate-recognition domains (CRD), Gal-8 has 3 isoforms, Gal-8S/M/L, of which Gal-8M is the most common. Gal-8 plays a key role in lymphatic and vascular angiogenesis, which is implicated in the systemic dissemination of tumor cells. Cancer-associated galectin-dependent activities are governed by the galectin expression level and/or the glycan phenotype on the cancer cell surface.

Dysregulated protein glycosylations on tumors are shown to enhance malignant behavior, metastasis, and/or drug resistance. These tumor-associated glycans are governed by dysregulated levels of glycosyltransferases, namely MGAT5, MGAT3, ST6GalNAc-2, FUT8, and ST6Gal-I. While these glycosylation pathways have been shown to modulate tumor progression, much of the MM glycome remains ill-defined. Loss of I-branching β-1,6 N-acetylglucosaminyltransferase 2 (GCNT2) and blood group I-antigen (I-branched glycan) are functionally related to melanoma progression. Originally identified as the enzyme that converts fetal i-linear poly-N-acetyllactosaminyl (poly-LacNAc) to I-branched glycans in adults, GCNT2 and its I-branched poly-LacNAc products on MM cells are lost. Loss of GCNT2 corresponds with increased MM aggressiveness, pro-survival signaling, and MM growth in vivo.

Multiple investigations have attributed the persistence of tumor-initiating cells (TICs) to widespread metastasis and disease relapse, including MM. TICs help confer immune evasion, self-renewal potential and resistance to therapy, including ICI therapy. One of the primary microenvironmental conditions responsible for TIC generation is hypoxia. Hypoxia is an intratumoral low oxygen condition linked to the augmentation of several malignancy-associated pathways. While research on hypoxia's influence in metastasis has mainly focused on the genomic and proteomic consequences of hypoxia-inducible factor 1α (HIF1α) induction, few investigations delve into how hypoxia impacts the cancer glycome. There is a lack of perspective on the role of hypoxia driving MM signature glycome. MMs, in fact, are characterized by severe hypoxia with a tissue oxygen tension of only 1.5%. Hence, exploring hypoxia-driven MM TIC generation in concert with the MM glycome signature is critical for understanding MM progression and therapy development. Further, there is a vital need for predictive biomarkers of therapeutic response and novel therapeutic targets to augment current treatment strategies.

BRIEF SUMMARY

The present invention provides methods and composition for diagnosis, prognosis, prevention and/or treatment of cancers such as melanomas. The subject invention provides biomarkers and methods for assessing the severity of a cancer/tumor and for monitoring the progressing of a cancer/tumor. The biomarkers include glycosylation-rerated genes and molecules affected by the glycosylation-rerated genes. The compositions according to the subject invention regulate malignancy-associated pathways and alter melanoma signaling, growth, and survival.

In accordance with the subject invention, GCNT2 expression was evaluated to establish a correlation with the clinical outcome of MM patients and whether and how hypoxia modulated the MM glycome and related downstream pathways. Immunohistochemical GCNT2 data on patient melanomas from early to late-stage disease indicated that loss of GCNT2 correlated with reduced patient survival. Using GCNT2 (high) and (low) MM cell variants, cells grown under hypoxia lowered GCNT2 and related I-branch poly-LacNAc expression, increased TIC development and tumor-initiating potential, and globally altered the melanoma glycome.

Importantly, MM-associated TIC marker, nerve growth factor receptor (NGFR)/CD271 inversely correlated with GCNT2 expression. Furthermore, hypoxia upregulated β-galactoside-binding lectin, galectin (Gal)-8 that bound preferentially to MM cells with depressed GCNT2/I-branching. Gal-8 incubation with MM cells elevated NGFR/CD271, whereas knockdown of Gal-8 dampened NGFR/CD271 expression, even under hypoxia. These results implicate Gal-8 as a putative modulator of NGFR expression. Additionally, compared with control sera, Gal-8 levels in sera from melanoma patients were significantly elevated.

In accordance with the subject invention, low GCNT2 levels correlate with poor patient survival and enhanced TIC characteristics in MM. Altering Gal-8 levels and binding to i-linear poly-LacNAc on MM cells directly correspond with NGFR expression.

This invention revealed the importance of hypoxia in governing the MM glycome signature by enforcing i-linear poly-LacNAc and Gal-8 expression and promoting TIC formation and uncovered a novel glycome-dependent mechanism regulating pro-MM TIC factor, NGFR. In accordance with the subject invention, i-linear poly-LacNAcs and Gal-8 can be used as putative biomarkers and therapeutic targets of MM.

In one embodiment, the subject invention provides a method for treating melanoma, preferably, metastatic melanoma, in a subject, comprising administering to the subject an inhibitor of Gal-8 expression (e.g., anti-Gal-8 antibodies or Gal-8 binding antagonists) and/or function (e.g., siRNAs or shRNAs targeting Gal-8).

In one embodiment, the subject invention provides a method for slowing the growth of melanoma cells, the method comprising contacting the melanoma cells with an inhibitor of Gal-8 expression (e.g., anti-Gal-8 antibodies or Gal-8 binding antagonists) and/or function (e.g., siRNAs or shRNAs targeting Gal-8).

In certain embodiments, the melanoma cells have a reduced expression level of GCNT2 prior to contacting the inhibitor of Gal-8. In certain embodiments, the melanoma cells are metastatic melanoma cells under hypoxia. In specific embodiments, the melanoma cells are resistant to one or more immune checkpoint inhibitors (ICIs).

In one embodiment, the subject invention provides a method for improving survival of a metastatic melanoma patient, the method comprising administering to the metastatic melanoma patient an inhibitor of Gal-8 expression (e.g., anti-Gal-8 antibodies or Gal-8 binding antagonists) and/or function (e.g., siRNAs or shRNAs targeting Gal-8). In a specific embodiment, the shRNA targeting Gal-8 is encoded by a sequence comprising SEQ ID NO: 5 or 6.

In a specific embodiment, the melanoma is resistant to immune checkpoint inhibitor (ICI) therapies.

BRIEF DESCRIPTION OF DRAWINGS

FIGS. 1A-1J. Loss of GCNT2 in patient melanoma tissue corresponds with increased patient mortality and increased expression of TIC markers in MM cells. IHC analysis of GCNT2 expression in patient melanomas (1A). GCNT2 expression score on melanoma (n=64) (Range 0-3: 0—No staining, 1—Light staining, 2—Moderate staining, and 3—Dark/strong staining) plotted against patient mortality outcome (1B). RT-qPCR analysis of GCNT2 in GCNT2 OE and KD A375 (1C) and A2058 (1D) cells. Flow cytometry of NGFR on GCNT2 EV and OE A375 cells (1E and 1F) and on GCNT2 Scr and KD A2058 cells (1G and 1H). In vivo limiting dilution assay of A375 EV/OE cells (1I) and A2058 Src/KD (1J) using cell numbers ranging from $10^5$ to $10^3$. For every experiment, at least 4 biological replicates were performed. (* $p<0.001$  $p<0.01$ * $p<0.05$.)

FIGS. 5A-5K. Hypoxia induces global alterations in glycosylation and glycome-associated genes. RNA sequencing analysis of glycosylation and glycome-associated genes was depicted in a transcriptomic heatmap of A375, A2058 and SkMel5 cells cultured under normoxia and hypoxia (5A). RT-qPCR analysis of Gal-8, NCAM and FUT11 in A375 (5B, 5C, and 5D) and A2058 (5E, 5F, and 5G) cells grown under normoxia, and hypoxia was conducted to validate results in (A). Flow cytometric analysis of Gal-8 and NCAM protein expression on A375 (5H and 5I) and A2058 (5J and 5K) cells grown under normoxia and hypoxia. For every experiment, at least 4 biological replicates were performed. (* p<0.001 p<0.01 *p<0.05.)

FIGS. 7A-7I. Gal-8 bound i-linear poly-LacNAcs preferentially on MM cells, and the major Gal-8 ligand on MM cells was identified as CD44. Flow cytometry analysis of rhGal-8 binding on A375 GNCT2 EV/OE (7A) and A2058 GCNT2 Scr/KD (7B) cells. GST-tagged Gal-8 affinity chromatography followed by immunoblotting for CD44 on parental A375 (7C) and A2058 (7E) cells, PNGase treated and control parental A375 (7D) and A2058 (7F) cells and A375 GCNT2 EV/OE (7G) and A2058 GCNT2 Scr/KD (7H) cells. Immunoblot analysis of AKT activation post Gal-8 treatment on A2058 GCNT2 Scr/KD (7I) cells. At least 4 biological replicates were performed. (**p<0.0001, * p<0.001, **p<0.01, *p<0.05.)

BRIEF DESCRIPTION OF SEQUENCES

Figure 1I:
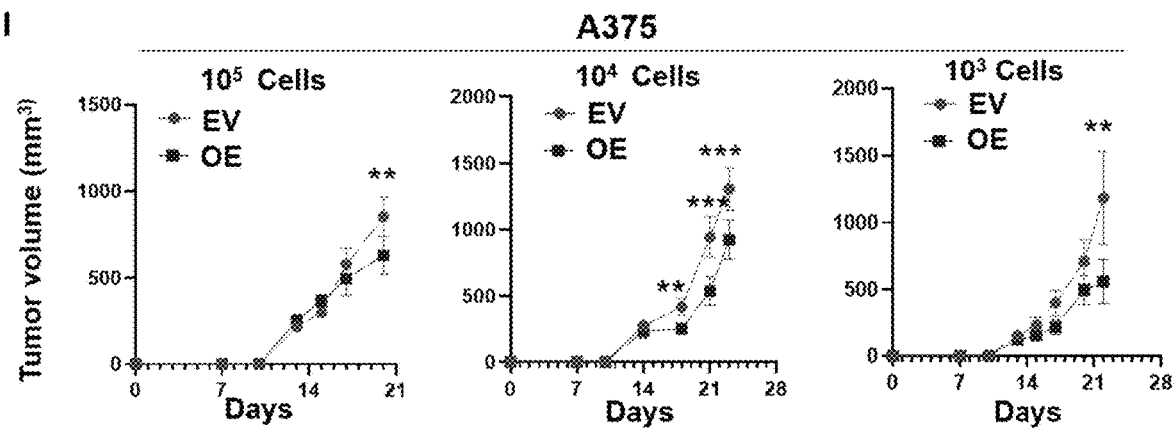

SEQ ID NO: 1 is a forward primer sequence of human GCNT2 contemplated for use according to the subject invention.

SEQ ID NO: 2 is a reverse primer sequence of human GCNT2 contemplated for use according to the subject invention.

SEQ ID NOs: 3-4 are shRNA target sequences of human GCNT2 shRNA contemplated for use according to the subject invention.

SEQ ID NOs: 5-6 are shRNA target sequences of human LGALS8 shRNA contemplated for use according to the subject invention.

SEQ ID NO: 7 is a non-target sequence of human LGALS8 scr control contemplated for use according to the subject invention.

SEQ ID NO: 8 is the nucleic acid sequence of GCNT2 contemplated for use according to the subject invention.

SEQ ID NO: 9 is the amino acid sequence of GCNT2 contemplated for use according to the subject invention.

DETAILED DESCRIPTION

The present invention provides methods and compositions for diagnosis, prognosis, prevention and/or treatment of cancers. The subject invention provides biomarkers and methods for assessing the severity of a cancer/tumor and for monitoring the progression of a cancer/tumor. The subject invention also provides compositions for treating a cancer/tumor, and for preventing or reducing the progression of a cancer/tumor.

In one embodiment, the cancers exhibit significant transcriptional changes in glycosylation-related genes. In a specific embodiment, the cancer is a skin cancer such as melanoma, preferably, metastatic melanoma (MM). Melanoma is one of the most aggressive forms of cancer, typically beginning in the skin and often metastasizing to vital organs and other tissues. Melanomas include, but are not limited to, superficial spreading melanoma (SSM), nodular melanoma (NM), Lentigo maligna, lentigo maligna melanoma (LMM), mucosal melanoma, polypoid melanoma, desmoplastic melanoma, amelanotic melanoma, soft-tissue melanoma, uveal melanoma and acral lentiginous melanoma (ALM).

The subject invention further provides methods and compositions for inhibiting the growth of primary melanomas, inhibiting metastasis, inhibiting the growth of metastases, killing circulating melanoma cells, inducing remission, extending remission, and/or inhibiting recurrence.

In one embodiment, the subject invention pertains to the identification i-linear poly-LacNAc and/or Galectin 8 (Gal-8) as being involved in the pathogenesis of melanomas, e.g., MM. The methods according to the subject invention use i-linear poly-LacNAc and/or Gal-8 as a biomarker for cancer diagnosis, progression and/or metastasis, for example: (1) the diagnosis of cancer; (2) the prognosis of cancer (e.g., monitoring cancer progression or regression from one biological state to another); (3) the susceptibility or prediction of response to treatment for a cancer; (4) the metastasis of cancer; and/or (5) the evaluation of the efficacy to a treatment for a cancer.

For the diagnosis of a cancer, the level of the specific biomarker in a subject or a sample of the subject can be compared to a baseline or control level. If the level is below or above the control level, a certain cancer is implicated. The prognosis of a cancer can be assessed by comparing the level of the specific biomarker at a first time point to the level of the biomarker at a second time point that occurs at a given interval. The prediction of response to treatment for a cancer can be determined by obtaining the level of a specific biomarker and correlating this level to a standard curve. The evaluation of the efficacy of the treatment for a cancer can be assessed by comparing the level of the specific biomarker before administration of the treatment to the level of the biomarker after the administration of the treatment.

Expression of genes of the present invention can be measured by many methods known in the art. In general, expression of a nucleic acid molecule (e.g., RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, flow cytometry, Western blot, Southern blot, Northern blot, immunohistochemistry, sequence analysis, microarray analysis, mass spectrometry analysis, detection of a reporter gene, or any other DNA/RNA hybridization platforms.

The subject invention pertains, in part, to the influence of hypoxia on global glycome alterations in MM cells, including the signature MM glycome featuring loss of GCNT2/I-branching, and whether hypoxia-dependent glycome events altered TIC development. In MM cells subjected to hypoxia, global transcriptional and N-glycomic profiling revealed several dysregulated glycome-related genes and enhanced i-linear poly-LacNAc expression. Of these alterations, including downregulation of GCNT2 and I-branched poly-LacNAcs, there was significant upregulation of Gal-8 directly corresponding to expression of a key TIC factor, nerve growth factor receptor (NGFR)/CD271, which enhances MM progression and therapy resistance. GCNT2 expression on patient melanomas was predictive of patient survival and Gal-8 levels were elevated in melanoma patient sera compared with healthy controls. Using GCNT2-enforced and -silenced MM cell variants, the results show that low GCNT2 expression increased TIC marker levels and in vivo tumor-initiating potential. Importantly, MM cell NGFR expression inversely correlated with GCNT2 expression. Gal-8 incubation with MM cells elevated NGFR, whereas Gal-8 silencing dampened NGFR expression, even under hypoxia, and reduced tumor-forming activity in vivo.

Also, Gal-8 bound preferentially to MM cells with depressed GCNT2/I-branching and high i-linear-poly-LacNAcs levels. Gal-8 affinity chromatography and proteomics analysis identified pro-metastatic and TIC marker CD44 as a major cell surface Gal-8 ligand, which was dependent on i-linear poly-LacNAc N-glycans for Gal-8-binding. Extracellular Gal-8 binding to i-linear poly-LacNAc$^{hi}$ MM cells increased AKT phosphorylation, which promotes tumor cell survival and is a downstream target of various activating cell surface receptors, including CD44. Interestingly, NGFR loss in Gal-8-silenced MM cells was not rescued by exogenous Gal-8-binding, suggesting that extracellular and intracellular Gal-8 expression may both have key roles in promoting MM cell-TIC potential. The present invention demonstrates the importance of hypoxia in governing the MM glycome to promote TIC formation and provides evidence for GCNT2/I-branching loss and elevated Gal-8 as biomarkers of MM.

In one embodiment, the subject invention provides methods for treating a cancer, e.g., MM, in a subject. In a specific embodiment, the method comprises:

(i) assessing the expression level of i-linear poly-LacNAc and/or Gal-8 in a sample obtained from the subject;

(ii) comparing the expression level of i-linear poly-LacNAc and/or Gal-8 in the sample to a reference derived from the expression level of i-linear poly-LacNAc and/or Gal-8 in samples obtained from healthy subjects;

(iii) identifying the cancer, e.g., MM, in the subject based on the increased level of i-linear poly-LacNAc and/or Gal-8 in the test sample; and (iv) administering a treatment to the subject.

In a further embodiment, the treatment is systemic and comprises administering Immune Checkpoint Inhibitors (ICIs), e.g., anti-PD1, anti-PDL1 and/or anti-CTLA4 treatments.

Immune checkpoints are known in the art and the term is well understood in the context of cancer therapy. Immune checkpoints include, but are not limited to, cytotoxic T-lymphocyte antigen 4 (CTLA-4), programmed cell death protein 1 (PD-1) and its ligand PDL-1, T-cell immunoglobulin and mucin domain-containing protein 3 (TIM-3), killer cell immunoglobulin-like receptor (KIR), lymphocyte activation gene-3 (LAG-3), V-domain immunoglobulin suppressor of T cell activation (VISTA), and B and T lymphocyte attenuator (BTLA). Inhibitors of immune checkpoints inhibit their normal immunosuppressive function, for example, by down regulating the expression of checkpoint molecules or by binding thereto and blocking normal receptor/ligand interactions. As a result, inhibitors of immune checkpoints enhance the immune response to an antigen, in particular, from a tumor cell.

Inhibitors of immune checkpoints are known in the art and preferred inhibitors include anti-immune checkpoint antibodies, such as anti-CTLA-4 antibodies (e.g., ipilimumab and tremelimumab), anti-PD-1 antibodies (e.g., nivolumab, lambrolozumab, pidilizumab and RG7446 (Roche)) and anti-PDL-1 antibodies (e.g., BMS-936559 (Bristol-Myers Squibb), MPDL3280A (Genentech), MSB0010718C (EMD-Serono) and MED14736 (AstraZeneca)).

With knowledge of an immune checkpoint target, a skilled artisan is able to develop an inhibitor thereof. Inhibitors may be selected from proteins, peptides, peptidomimetics, peptoids, antibodies, antibody fragments, small inorganic molecules, small non-nucleic acid organic molecules or nucleic acids such as anti-sense nucleic acids, small interfering RNA (siRNA) molecules or oligonucleotides. The inhibitor may for example be a modified version of the natural ligand (e.g., for CTLA-4, CD80 (B7-1) and CD86 (B7-2)), such as a truncated version of one of the ligands. They may be naturally occurring, recombinant or synthetic.

In one embodiment, the subject invention provides a method of identifying a cancer, e.g., MM, in a subject, the method comprising:

(a) determining the level of one or more biomarkers (e.g., i-linear poly-LacNAc and/or Gal-8) in:
  i) a test sample obtained from the subject, and
  ii) optionally, a control sample;

(b) optionally, obtaining at least one reference value corresponding to the level of one or more biomarkers (e.g., i-linear poly-LacNAc and/or Gal-8); and (c) identifying the cancer, e.g., MM, in the subject based on the increased level of one or more biomarkers (e.g., i-linear poly-LacNAc and/or Gal-8) in the test sample and optionally, administering a therapy to the subject to treat and/or manage the cancer, e.g., MM.

In one embodiment, the control sample is obtained from: i) an individual belonging to the same species as the subject and not having, for example, MM, or ii) the subject at a prior time known to be free from MM.

In one embodiment, the subject invention provides methods for treating a cancer, e.g., melanoma, preferably, MM, involving the inhibition of Gal-8 expression and/or function. The method comprises administering to the subject a pharmaceutically effective amount of an inhibitor of Gal-8 expression (e.g., gene silencing, such as siRNAs and shRNAs targeting Gal-8) and/or function (e.g., anti-Gal-8 antibodies or Gal-8 binding antagonists). Methods to inhibit Gal-8 function or expression would reduce melanoma metastasis progression and/or enhance therapeutic response to conventional immunotherapies used to treat metastatic melanoma.

In specific embodiments, the shRNA targeting Gal-8 is placed in a construct, e.g., a viral plasmid, wherein the construct comprises a DNA sequence that is transcribed into an shRNA targeting Gal-8, the DNA sequence for the shRNA targeting Gal-8 comprising the sequence of SEQ ID NO: 5 or 6.

In specific embodiments, the shRNA targeting GCNT2 is placed in a construct, e.g., a viral plasmid, wherein the construct comprises a DNA sequence that is transcribed into an shRNA targeting GCNT2, the DNA sequence for the shRNA targeting GCNT2 comprising the sequence of SEQ ID NO: 3 or 4.

In certain embodiments, the shRNA comprises a sequence fully complementary to a sequence in a target gene. In some embodiments, the shRNA targeting Gal-8 comprises a sequence fully complementary to a target sequence of Gal-8 and the shRNA targeting GCNT2 comprises a sequence fully complementary to a target sequence of GCNT2.

In a specific embodiment, the shRNA targeting Gal-8 comprises a sequence fully complementary to SEQ ID NO: 5 or 6. In a specific embodiment, the shRNA targeting GCNT2 comprises a sequence fully complementary to SEQ ID NO: 3 or 4.

In certain embodiments, the step of administering to the subject a pharmaceutically effective amount of an shRNA targeting a gene, e.g., Gal-8, may comprise administering an expression construct comprising a sequence encoding an shRNA targeting the gene, e.g., Gal-8, wherein administration of the expression construct can attenuate target gene expression.

In certain embodiments, the method for treating cancer, e.g., melanoma, preferably, MM, further comprises administering to the subject a pharmaceutically effective amount of 1) a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 2) an amino acid sequence of GCNT2 protein, as well as biologically-active fragments, and variants thereof, or an amino acid sequence sharing at least 50%, 55%, 60%, 65%, 70%, 75%, 80%, 85%, 90%, 95%, 96%, 97%, 98% or 99% identity with GCNT2, 3) a vector comprising a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 4) a cell that overexpresses a nucleic acid sequence of GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, and/or 5) a cell that overexpresses an amino acid sequence of GCNT2 protein, as well as biologically-active fragments, and variants thereof, or an amino acid sequence sharing at least 50%, 55%, 60%, 65%, 70%, 75%, 80%, 85%, 90%, 95%, 96%, 97%, 98% or 99% identity with GCNT2.

In one embodiment, the nucleic acid sequence of GCNT2 comprises, or consists of, a sequence of Accession No. NM_145649 (SEQ ID NO: 8), or a nucleic acid sequence sharing at least 50%, 55%, 60%, 65%, 70%, 75%, 80%, 85%, 90%, 95%, 96%, 97%, 98% or 99% identity with Accession No. NM 145649.

In one embodiment, the amino acid sequence of GCNT2 comprises, or consists of, a sequence of Accession No. NP_663624 (SEQ ID NO: 9) or an amino acid sequence sharing at least 50%, 55%, 60%, 65%, 70%, 75%, 80%, 85%, 90%, 95%, 96%, 97%, 98% or 99% identity with Accession No. NM 663624.

In one embodiment, the subject invention provides methods for treating a cancer, e.g., melanoma, preferably, MM, which involve the reduction of i-linear poly-LacNAc level in MM cells, and/or the reduction of the interaction between i-linear poly-LacNAc and Gal-8.

In one embodiment, the subject invention provides methods for treating a cancer, e.g., melanoma, preferably, MM, which involve the reduction/inhibition of CD44 on MM cells, and/or the reduction/inhibition of the interaction between CD44 and Gal-8.

In one embodiment, the subject invention provides methods for increasing or improving survival of a MM patient, which involve the inhibition of Gal-8 expression and/or function. The method comprises administering to the subject a pharmaceutically effective amount of an inhibitor of Gal-8 expression (e.g., gene silencing such as siRNAs and shRNAs targeting Gal-8) and/or function (e.g., anti-Gal-8 antibodies or Gal-8 binding antagonists).

In one embodiment, the subject invention provides methods for increasing or improving survival of a MM patient, which involve the reduction of i-linear poly-LacNAc level in MM cells, and/or the reduction of the interaction between i-linear poly-LacNAc and Gal-8.

In one embodiment, the subject invention provides methods for reducing the expression of tumor-initiating cell markers, e.g., KLF4, and/or NGFR/CD271, in MM cells, which involve the overexpression of GCNT2, the method comprising administering to the subject a pharmaceutically effective amount of 1) a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 2) an amino acid sequence of GCNT2 protein, as well as biologically-active fragments, and variants thereof, or an amino acid sequence sharing at least 50%, 55%, 60%, 65%, 70%, 75%, 80%, 85%, 90%, 95%, 96%, 97%, 98% or 99% identity with GCNT2, 3) a vector comprising a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 4) a cell that overexpresses a nucleic acid sequence of GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, and/or 5) a cell that overexpresses an amino acid sequence of GCNT2 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with GCNT2.

In one embodiment, the subject invention provides methods for reducing the expression of tumor-initiating cell markers, e.g., KLF4, and/or NGFR/CD271, in MM cells, the method comprising contacting the MM cells with 1) a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 2) an amino acid sequence of GCNT2 protein, as well as biologically-active fragments, and variants thereof, or an amino acid sequence sharing at least 50%, 55%, 60%, 65%, 70%, 75%, 80%, 85%, 90%, 95%, 96%, 97%, 98% or 99% identity with GCNT2, and/or 3) a vector comprising a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2; or a composition comprising 1), 2), and/or 3) above.

Contacting the MM cells with the above 1), 2), and/or 3) or compositions results in, for example, the transfection or transduction of the GCNT2 gene into the melanoma cells or the direct delivery of the protein, which leads to overexpression of GCNT2 in these cells. There are various transfection methods, including physical treatment (e.g., electroporation microinjection, cell squeezing, impalefection, hydrostatic pressure, continuous infusion, sonication, nanoparticles, and magnetofection), chemical materials (e.g., lipofection, and polyplexes) or biological particles (e.g., retrovirus, lentivirus, adenovirus, adeno-associated virus, and herpes simplex virus) that are used as carriers.

As used herein, "variants" of a protein refer to sequences that have one or more amino acid substitutions, deletions, additions, or insertions. In preferred embodiments, these substitutions, deletions, additions or insertions do not materially adversely affect the protein activity. Variants that retain one or more biological activities are within the scope of the present invention.

"Fragments" and its variants are also within the scope of proteins of the subject invention, so long as the fragment retains one or more biological properties. Preferably, the fragment is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the full length protein, e.g., GCNT2.

In one embodiment, the subject invention provides methods for reducing the expression of tumor-initiating cell markers, e.g., KLF4, and/or NGFR/CD271, in MM cells, which involves the inhibition of Gal-8 expression and/or function. The method comprises administering to the subject a pharmaceutically effective amount of an inhibitor of Gal-8 expression (e.g., gene silencing such as siRNAs and shRNAs targeting Gal-8) and/or function (e.g., anti-Gal-8 antibodies or Gal-8 binding antagonists). The method may comprise administering to the subject a pharmaceutical composition comprising an inhibitor of Gal-8 expression (e.g., gene silencing such as siRNAs and shRNAs targeting Gal-8) and/or function (e.g., anti-Gal-8 antibodies or Gal-8 binding antagonists). The pharmaceutical composition may also comprise a pharmaceutically acceptable carrier.

"Pharmaceutically acceptable carrier" refers to a diluent, adjuvant or excipient with which the antigen disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith. Examples of carriers suitable for use in the pharmaceutical compositions are known in the art and such embodiments are within the purview of the invention.

In one embodiment, the method for reducing the expression of tumor-initiating cell markers, e.g., KLF4, and/or NGFR/CD271, in MM cells comprises contacting the MM cells with an inhibitor of Gal-8 expression (e.g., gene silencing such as siRNAs and shRNAs targeting Gal-8) and/or function (e.g., anti-Gal-8 antibodies or Gal-8 binding antagonists).

In certain embodiments, the step of contacting the MM cells with an inhibitor of Gal-8 may comprise introducing an expression construct comprising a sequence encoding an shRNA targeting Gal-8 into the MM cells (e.g., in vitro or in vivo), wherein the shRNA is expressed in an amount sufficient to attenuate Gal-8 expression and the shRNA is stably expressed in the MM cells.

In specific embodiments, the expression construct comprises a sequence encoding an shRNA targeting Gal-8, wherein the sequence encoding an shRNA targeting Gal-8 comprises the sequence of SEQ ID NO: 5 or 6.

In certain embodiments, the shRNA comprises a sequence fully complementary or substantially complementary (e.g., at least 80%, 85%, 90%, 95% or 100% complementary) to a sequence in a target gene. In some embodiments, the shRNA targeting Gal-8 comprises a sequence fully complementary or substantially complementary (e.g., at least 80%, 85%, 90%, 95% or 100% complementary) to a target sequence of Gal-8. In a specific embodiment, the shRNA targeting Gal-8 comprises a sequence fully complementary or substantially complementary (e.g., at least 80%, 85%, 90%, 95% or 100% complementary) to SEQ ID NO: 5 or 6.

As used herein, the term "fully complementary" with regard to a sequence refers to a complement of the sequence by Watson-Crick base pairing, whereby guanine (G) pairs with cytosine (C), and adenine (A) pairs with either uracil (U) or thymine (T). A sequence may be fully complementary to the entire length of another sequence, or it may be fully complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "substantially complementary" refers to sequences of nucleotides where a majority (e.g., at least about 80%, 85%, 90%, 95%, 96%, 97%, 98%, or 99%) or all of the bases in the sequence are complementary, or one or more (e.g., no more than 20%, 15%, 10%, 5%, 4%, 3%, 2%, or 1%) bases are non-complementary, or mismatched. A complementary sequence can be a reverse complement of the sequence allowing for Watson-Crick base pairing, wobble base pairing, or both, whereby G pairs with either C or U, and A pairs with either U or T. A sequence may be complementary to the entire length of another sequence or it may be complementary to a specified portion or length of another sequence. One skilled in the art will recognize that the U may be present in RNA, and that T may be present in DNA. Therefore, a U within an RNA sequence may pair with A or G in either an RNA sequence or a DNA sequence, while an A within either of an RNA or DNA sequence may pair with a U in a RNA sequence or T in a DNA sequence. Two sequences that are substantially complementary may hybridize to each other, e.g., under low stringency, medium stringency, high stringency, or very high stringency conditions.

As used herein, the term "construct," "expressing construct" or "expression construct" is a generic term that includes nucleic acid preparations designed to achieve an effect of interest. An expressing construct comprises an RNAi molecule that can be cleaved in vivo to form an siRNA or a mature shRNA. For example, an RNAi construct is an expression vector capable of giving rise to an siRNA or a mature shRNA in vivo.

The term "vector" refers to a vehicle for introducing a nucleic acid into a cell, which includes, but is not limited to, plasmid, phagemid, virus, bacterium, and vehicle derived from viral or bacterial sources. A "plasmid" is a circular, double-stranded DNA molecule. A useful type of vector for use in the present invention is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome.

In certain embodiments, the vector is a viral vector. Exemplary viral vectors include retroviral, including lentiviral, adenoviral, baculoviral and avian viral vectors. The use of viral vector-based RNAi delivery not only allows for stable single-copy genomic integrations but also avoids the non-sequence specific response via cell-surface toll-like receptor 3 (TLR3), which has raised many concerns for the specificity of siRNA mediated effects.

In some embodiments, the shRNA of the invention can be introduced into the cell directly, or can be complexed with cationic lipids, packaged within liposomes, or otherwise delivered to the cell. In certain embodiments, the shRNA can be a synthetic shRNA, including shRNAs incorporating modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications. In some embodiments, an shRNA of the invention contains modified nucleotides that increase the stability or half-life of the shRNA molecule in vivo and/or in vitro.

In one embodiment, the subject invention provides methods for reducing/slowing down the growth/potential of tumor-initiating cells in a subject, the method comprising administering to the subject a pharmaceutically effective amount of 1) a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 2) an amino acid sequence of GCNT2 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with GCNT2, 3) a vector comprising a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 4) a cell that overexpresses a nucleic acid sequence of GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, and/or 5) a cell that overexpresses an amino acid sequence of GCNT2 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with GCNT2.

In one embodiment, the method of treating/preventing/reducing the progression of MM may further comprises administering to the subject one or more therapeutic agents. The therapeutic agent may comprise a chemotherapeutic agent, immunotherapeutic agent, gene therapy or radio therapeutic agent.

The administration routes include, but are not limited to, the local, oral, ophthalmic, nasal, topical, intratumoural, transdermal, intra-articular, parenteral (e.g., intravenous, intraperitoneal, intradermal, subcutaneous or intramuscular), intracranial, intracerebral, intraspinal, intravaginal, intrauterine, or rectal route. Additionally, the composition or therapeutic agents may be administered directly into the tumor of MM.

A further embodiment of the invention provides a method for monitoring the effect of a treatment for a cancer, such as MM, in a subject. A method for monitoring the effect of a treatment for a cancer, such as MM, in a subject may comprise:

(a) determining the level of one or more biomarkers (e.g., i-linear poly-LacNAc and/or Gal-8) in:
  i) a pre-treatment test sample obtained from the subject before the treatment,
  ii) a post-treatment test sample obtained from the subject after the treatment, and
  ii) optionally, a control sample;
(b) optionally obtaining at least one reference values corresponding to levels of one or more biomarkers (e.g., i-linear poly-LacNAc and/or Gal-8); and
(c) identifying the treatment for the cancer, e.g., MM, in the subject as effective based on a reduced levels of one or more biomarkers (e.g., i-linear poly-LacNAc and/or Gal-8) in the post-treatment test sample compared to the levels of one or more biomarkers (e.g., i-linear poly-LacNAc and/or Gal-8) in the pre-treatment test sample and optionally, continuing the treatment in the subject, or
(d) identifying the treatment for the cancer, e.g., MM, in the subject as ineffective if the levels of one or more biomarkers (e.g., i-linear poly-LacNAc and/or Gal-8) in the post-treatment test sample remains the same or increases compared to the levels of one or more biomarkers (e.g., i-linear poly-LacNAc and/or Gal-8) in the pre-treatment test sample and optionally, modifying the treatment in the subject.

In one embodiment, the subject invention provides a method for diagnosing and/or assessing the progression of MM in a subject, the method comprising:

(i) assessing the expression level of one or more biomarkers (e.g., i-linear poly-LacNAc and/or Gal-8) in a sample obtained from the subject;
(ii) comparing the expression level of one or more biomarkers (e.g., i-linear poly-LacNAc and/or Gal-8) in the sample to a reference derived from the expression level of one or more biomarkers (e.g., i-linear poly-LacNAc and/or Gal-8) in samples obtained from healthy subjects; and
(iii) determining the progression of MM in the subject based on whether the expression level of one or more biomarkers (e.g., i-linear poly-LacNAc and/or Gal-8) in the subject is up-regulated or down-regulated.

In further embodiments, the biomarker is Gal-8 and a down-regulation in the expression level of i-linear poly-LacNAc and/or Gal-8 in the sample is indicative of an improvement in the subject's condition.

In one embodiment, the subject invention provides a method for stratifying a tumor stage (e.g., of MM) in a subject, the method comprising:
(i) assessing the expression level of one or more biomarkers (e.g., i-linear poly-LacNAc and/or Gal-8) in a tumor sample obtained from the subject;
(ii) comparing the expression level of one or more biomarkers (e.g., i-linear poly-LacNAc and/or Gal-8) in the tumor sample to a reference derived from the expression level of one or more biomarkers (e.g., i-linear poly-LacNAc and/or Gal-8) in healthy samples obtained from healthy subjects; and
(iii) determining the tumor stage in the subject based on whether the expression level of one or more biomarkers (e.g., i-linear poly-LacNAc and/or Gal-8) in the subject is up-regulated or down-regulated.

In one embodiment, the subject invention provides a method for predicting an outcome of an anti-cancer therapy, in a subject, the method comprising:
(i) assessing the expression level of i-linear poly-LacNAc and/or Gal-8 in a sample (e.g., tumor specimen) obtained from the subject;
(ii) comparing the expression level of i-linear poly-LacNAc and/or Gal-8 in the sample to a reference derived from the expression level of i-linear poly-LacNAc and/or Gal-8 in samples obtained from healthy subjects; and
(iii) determining/predicting the outcome of the anti-cancer therapy by assessing whether the level of i-linear poly-LacNAc and/or Gal-8 in the subject is up-regulated or down-regulated, wherein a down-regulation in the expression of i-linear poly-LacNAc and/or Gal-8 indicates that the cancer, e.g., MM, will be responsive and/or sensitive to the anti-cancer therapy.

In one embodiment, the subject invention provides a method for assessing the response of a melanoma subject to an anti-melanoma therapy, the method comprising:
assessing an expression level of Gal-8 in a sample obtained from the melanoma subject before and after the anti-melanoma therapy;
comparing the expression level of Gal-8 in the sample before and after the anti-melanoma therapy; and
determining the melanoma subject being responsive to the anti-melanoma therapy by a decreased expression level of Gal-8 in the sample, or determining the melanoma subject being non-responsive to the anti-melanoma therapy if the expression level of Gal-8 remains the same or increases.

The term "sample" as used herein refers to any physical sample that includes a cell or a cell extract from a cell, a tissue, a biofluid or an organ including a biopsy sample. The sample can be from a biological source such as a subject, or a portion thereof, or can be from a cell culture. Samples from a biological source can be from a normal or an abnormal organism, such as an organism known to be suffering from a condition or a disease state, or any portion thereof. Samples can also be from any fluid, e.g., blood and serum, tissue or organ including normal and abnormal (diseased) fluid, tissue or organ. Samples from a subject can be used, processed or cultured such that cells from the sample can be sustained in vitro as a primary or continuous cell culture or cell line.

In a specific embodiment, the sample is a skin sample, for example, skin cells, skin extract, and/or skin tissue. Preferably, the skin sample may comprise melanocytes. The term "subject" or "patient," as used herein, describes an organism, including mammals such as primates, to which diagnosis, prevention, assessment, and/or treatment according to the present invention can be provided. Mammalian species that can benefit from the disclosed methods of treatment include, but are not limited to, apes, chimpanzees, orangutans, humans, monkeys; domesticated animals such as dogs, cats; live-stocks such as horses, cattle, pigs, sheep, goats, and chickens; and other animals such as mice, rats, guinea pigs, and hamsters.

In a specific embodiment, the subject may have hypoxia. In a specific embodiment, the subject may not have hypoxia. In a specific embodiment, the MM cells are under hypoxia. In a specific embodiment, the MM cells are not under hypoxia.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

In a further embodiment, the melanoma or MM may be a drug-resistant melanoma or MM. In a preferred embodiment, the melanoma is an ICI therapy-resistant melanoma.

In one embodiment, the subject in need of the treatment for melanoma, preferably, ICI therapy-resistant melanoma, has been treated by ICI or IC therapy.

In one embodiment, the subject invention provides a method for treating an IC therapy-resistant melanoma in a subject, the method comprising administering to the subject an inhibitor of Gal-8 expression (e.g., gene silencing such as siRNAs and shRNAs targeting Gal-8) and/or function (e.g., anti-Gal-8 antibodies or Gal-8 binding antagonists) or a composition comprising an inhibitor of Gal-8 expression (e.g., gene silencing such as siRNAs and shRNAs targeting Gal-8) and/or function (e.g., anti-Gal-8 antibodies or Gal-8 binding antagonists).

In some embodiments, the method further comprises administering to the subject a pharmaceutical composition comprising 1) a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2, 2) an amino acid sequence of GCNT2 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with GCNT2, and/or 3) a vector comprising a nucleic acid sequence that encodes GCNT2 or a nucleic acid sequence sharing at least 50%, 55%, 60%, 65%, 70%, 75%, 80%, 85%, 90%, 95%, 96%, 97%, 98% or 99% identity with the nucleic acid sequence that encodes GCNT2.

In one embodiment, the subject invention further provides a method for increasing/enhancing/improving the sensitivity of a subject having melanoma to an IC therapy, the method comprising administering to the subject an inhibitor of Gal-8 expression (e.g., gene silencing such as siRNAs and shRNAs targeting Gal-8) and/or function (e.g., anti-Gal-8 antibodies or Gal-8 binding antagonists) or a pharmaceutical composition comprising an inhibitor of Gal-8 expression (e.g., gene silencing such as siRNAs and shRNAs targeting Gal-8) and/or function (e.g., anti-Gal-8 antibodies or Gal-8 binding antagonists).

In a further embodiment, the pharmaceutical composition may be administered prior to the administration of the IC therapy, simultaneously with the IC therapy, or after the administration of the IC therapy.

In a preferred embodiment, the IC therapy is an anti-PD-1 therapy.

In one embodiment, the subject invention provides a method for increasing/enhancing/improving the sensitivity of melanoma cells to an ICI, the method comprising contacting the melanoma cells with an inhibitor of Gal-8 expression (e.g., gene silencing such as siRNAs and shRNAs targeting Gal-8) and/or function (e.g., anti-Gal-8 antibodies or Gal-8 binding antagonists) or a pharmaceutical composition comprising an inhibitor of Gal-8 expression (e.g., gene silencing such as siRNAs and shRNAs targeting Gal-8) and/or function (e.g., anti-Gal-8 antibodies or Gal-8 binding antagonists). In a specific embodiment, the shRNA targeting Gal-8 is encoded by a sequence comprising SEQ ID NO: 5 or 6.

In one embodiment, melanoma may be a stage 0, I, II, III or IV melanoma. Stage 0 melanoma is a very early-stage disease known as melanoma in situ. The tumor is limited to the epidermis with no invasion of surrounding tissues, lymph nodes, or distant sites. Stage 0 melanoma is considered to be very low risk for disease recurrence or spread to lymph nodes or distant sites.

Stage I melanoma is characterized by tumor thickness, presence and number of mitoses, and ulceration status. Stage I melanomas are considered to be low-risk for recurrence and metastasis. Sentinel lymph node biopsy is recommended for Stage I tumors thicker than 1.0 mm and for any ulcerated tumors of any thickness. Surgery is a common treatment for Stage I melanoma.

Stage II melanomas also are localized tumors characterized by tumor thickness and ulceration status. Stage II melanoma is considered to be intermediate-risk for local recurrence or distant metastasis. In addition to biopsy and surgery as described for Stage I, Stage II treatment may include adjuvant therapy, which is a treatment given in addition to a primary cancer treatment, following surgery. Treatments may include interferons therapies (e.g., interferon alfa-2a, and/or alfa-2b), and vaccines therapy.

Stage III melanomas are tumors that have spread to regional lymph nodes, or have developed in transit metastasis or satellites. Stage III disease is considered to be intermediate-to high-risk for local recurrence or distant metastasis. In addition to surgery and adjuvant therapy as described above, Stage III melanoma treatment often includes therapeutic lymph node dissection (TLND) to remove regional lymph nodes from the area where cancerous lymph nodes were found. The goal of the surgery is to prevent further spread of the disease through the lymphatic system.

Stage IV melanomas often are associated with metastasis beyond the regional lymph nodes to distant sites in the body. Common sites of metastasis are vital organs (lungs, abdominal organs, brain, and bone) and soft tissues (skin, subcutaneous tissues, and distant lymph nodes). Stage IV melanoma may be characterized by the location of the distant metastases; the number and size of tumors; and the serum lactate dehydrogenase (LDH) level. Elevated LDH levels usually indicate that the tumor has spread to internal organs. Treatments may include surgery to remove cancerous tumors or lymph nodes that have metastasized to other areas of the body, systemic therapies and radiation therapy.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Methods
Cells

Human A375, A2058 and SK-MEL-5 MM cell lines were obtained from ATCC and grown in DMEM media with 10% FBS (Atlanta) and 1% Antibiotic-Anti-mitotic (Gibco). GCNT2 overexpressing (OE) and silenced (KD) MM cells were generated by lentiviral transduction. For Gal-8 KD cell lines commercial lentiviral particles with shRNA directed against Gal-8 and scrambled control (Scr) were purchased (GeneCopoeia). A375 and 2058 cells were transduced and selected in 1 mg/ml Hygromycin (Corning) containing media. Reagent details and oligonucleotide details are available in Tables 1 and 2.

TABLE 1

Antibodies and reagents
Antibodies/Reagents

| S. No | Name | Source | Identifier | Concentrations |
|---|---|---|---|---|
| 1 | Rabbit polyclonal anti-GCNT2 | Sigma-Aldrich | Cat# HPA026776 | 1:500 (IHC) |
| 2 | Leica Bond Polymer Detection Kit | Leica | Cat# DS9800 | N/A |
| 3 | OSK-14 (antiDI) human IgM | Dr. Yoshihiko Tani Japanese Red Cross Kinki Block Blood Center | N/A | 1:50-1:100 (Batch specific) (Flow cytometry) |
| 4 | OSK-28 (antiDI) human IgM | Dr. Yoshihiko Tani Japanese Red Cross Kinki Block Blood Center | N/A | 1:20-1:50 (Batch specific) (Flow cytometry) |
| 5 | IRDye ® 800CW Goat anti-Rabbit IgG (H + L) | LI-COR Biosciences | Cat# 926-32211 | 1:10000 (Western) |
| 6 | IRDye ® 800CW Goat anti-Mouse IgG (H + L) | LI-COR Biosciences | Cat# 926-32210 | 1:10000 (Western) |
| 7 | IRDye ® 680RD Goat anti-Mouse IgG (H + L) | LI-COR Biosciences | Cat# 926-68070 | 1:10000 (Western) |
| 8 | IRDye ® 680LT Donkey anti-Rabbit IgG (H + L) | LI-COR Biosciences | Cat# 926-68023 | 1:10000 (Western) |
| 9 | HIF-1α (D2U3T) Rabbit mAb | Cell Signaling | Cat# 14179S | 1:1000 (Western) |
| 10 | Phospho-Akt (Ser473) (D9E) XP ® Rabbit mAb #4060 | Cell Signaling | Cat# 4060S | 1:1000 (Western) |
| 11 | Akt (pan) (40D4) Mouse mAb | Cell Signaling | Cat# 2920S | 1:1000 (Western) |
| 12 | Rabbit Beta actin (D6A8) | Cell Signaling | Cat# 8457S | 1:1000 (Western) |
| 13 | Anti-beta Actin, Clone: mAbcam 8226 | Abcam ™ | Cat# ab8226 | 1:1000 (Western) |
| 14 | Recombinant Anti-p75 NGF Receptor antibody [EP1039Y] | Abcam ™ | Cat# ab52987 | 1:1000 (Western) |
| 15 | APC anti-human CD271 (NGFR) Antibody | Biolegend | Cat# 345107 | 1 µg/ml (Flow cytometry) |
| 16 | APC Mouse IgG1, κ Isotype Ctrl Antibody | Biolegend | Cat# 400120 | 1 µg/ml (Flow cytometry) |
| 17 | PE anti-human CD56 (NCAM) Antibody | Biolegend | Cat# 362508 | 1 µg/ml (Flow cytometry) |
| 18 | PE Mouse IgG1, κ Isotype Ctrl Anitbody | Biolegend | Cat# 400114 | 1 µg/ml (Flow cytometry) |
| 19 | Human Galectin-8 Antibody, Goat Polyclonal, R&D Systems ™ | R&D Biosystems | Cat#AF1305 | 1 µg/ml (Flow cytometry) |
| 20 | Human Galectin-8 Recombinant Protein | R&D Systems ™ | Cat# 1305GA050 | 10 µg/ml-40 µg/ml |
| 21 | Donkey Anti-Goat IgG H&L (Alexa Fluor ® 488) | Abcam ™ | Cat# ab150129 | 1:2000 (Flow cytometry) |
| 22 | Foxp3/Transcription Factor Staining Buffer Set | eBioscience ™ | Cat# 50-112-8857 | N/A |
| 23 | GCNT2 TaqMan ® primer | Thermo Scientific | AssayID: Hs00377334_m1 | N/A |
| 24 | KLF4 TaqMan ® primer | Thermo Scientific | AssayID: Hs00358836_m1 | N/A |
| 25 | NGFR TaqMan ® primer | Thermo Scientific | AssayID: Hs00609976_m1 | N/A |
| 26 | MITF TaqMan ® primer | Thermo Scientific | AssayID: Hs01117294_m1 | N/A |
| 27 | 18S TaqMan ® primer | Thermo Scientific | AssayID: Hs01117294_m1 | N/A |
| 28 | LGALS8 TaqMan ® primer | Thermo Scientific | Hs01057135_m1 | N/A |
| 31 | TaqMan ® Fast Advanced Master Mix | Thermo Scientific | Cat# 4444557 | N/A |

TABLE 1-continued

Antibodies and reagents
Antibodies/Reagents

| S. No | Name | Source | Identifier | Concentrations |
|---|---|---|---|---|
| 32 | SuperScript ™ VILO ™ cDNA Synthesis Kit | Invitrogen ™ | Cat# 11-754-050 | N/A |
| 33 | RIPA Lysis and Extraction Buffer | Thermo Scientific | Cat# 89900 | N/A |
| 34 | Halt ™ Protease and Phosphatase Inhibitor Single-Use Cocktail (100X) | Thermo Scientific | Cat#78440 | N/A |
| 35 | BCA protein assay kit | Thermo Scientific | Cat# PI23227 | N/A |
| 36 | Laemmli SDS sample buffer | Alfa Aesar | Cat# AAJ61337AC | 1X |
| 37 | Immobilon PVDF | Millipore | Cat# IPFL00010 | N/A |
| 38 | Criterion 4-12% Bis-Tris Precast Gels-12 wells + 2 | BioRad | Cat# 3450123 | N/A |
| 39 | Intercept ® (TBS) blocking buffer | LI-COR Biosciences | Cat# NC1660550 | N/A |
| 40 | anti-human IgM-APC | Biolegend | Cat# 314510 | 1:400 (Flow cytometry) |
| 41 | LIVE/DEAD ™ Fixable Aqua Dead Cell Stain Kit, for 600 nm excitation | Fisher | Cat# 50-112-1525 | 1:1000 (Flow cytometry) |
| 42 | Accutase-Enzyme Cell Detachment Medium | Fisher | Cat# 50-112-9055 | N/A |
| 43 | Neuraminidase | Roche | Cat# 10269611001 | 0.125 U/ml |
| 44 | RNeasy Plus Mini Kit (250) | QIAGEN | Cat# 74136 | N/A |
| 45 | Sep-Pak C18 6 cc Vac Cartridge, 500 mg Sorbent per Cartridge, 55-105 µm, 300/pk | Waters Corporation | Cat# SKU186006325 | N/A |
| 46 | N-Glycosidase F | MilliporeSigma-Roche | Cat# 11365169001 | |
| 47 | AdvanceBio Sialidase S | Agilent | Cat# GK80021 | |
| 48 | Human Galectin-8 ELISA Kit | SigmaMillipore | Cat# RABI050-1KT | N/A |
| 49 | Trypsin Singles, Proteomics Grade | Sigma Aldrich | Cat# T7575-1KT | 1:20 (enzyme:protein) |
| 50 | Pierce ™ C18 Tips, 100 µL bed | Thermo Scientific | Cat# PI87784 | N/A |
| 51 | New England Biolabs PNGase F (Glycerol-free)-15000 units | New England Biolabs | Cat# 50-811-832 | 1000-2500 U |
| 52 | Sino Biological Human Galectin-8/LGALS8 Protein (GST Tag) | Sino Biological | Cat# 50-161-4565 | 10 µg/ml (affinity chromatography) |
| 53 | Pierce ™ Glutathione Magnetic Agarose Beads | Thermo Scientific | Cat# PI78601 | N/A |
| 54 | CD44 (156-3C11) Mouse mAb | Cell Signaling | Cat# 3570S | 1:2000 (Western) |

TABLE 2

Oligonucleotide details
Oligonucleotide details

| | Gene | Forward Sequence | Reverse Sequence | Comments |
|---|---|---|---|---|
| 1 | Human GCNT2 | CGACAGATCTGCCACCATGAACTTTTGGAGGTACTGCTTT (SEQ ID NO: 1) | TGTCAAGCTTTCAAAAATACCAGCTGGGTTGTA (SEQ ID NO: 2) | Cloning primers |
| 2 | Human GCNT2 shRNA #1 | GCTAACAAGTTTGAGCTTAAT (SEQ ID NO: 3) | — | shRNA target sequence |
| 3 | Human GCNT2 shRNA #2 | GCTCACCTCTATATTAGTTTA (SEQ ID NO: 4) | — | shRNA target sequence |
| 4 | Human LGALS8 shRNA #1 | CCTACAGAATATCATCTATAA (SEQ ID NO: 5) | — | shRNA target sequence |

TABLE 2-continued

Oligonucleotide details

| | Gene | Forward Sequence | Reverse Sequence | Comments |
|---|---|---|---|---|
| 5 | Human LGALS8 shRNA #2 | GCTCGGACTTACAAAGTACCC (SEQ ID NO: 6) | — | shRNA target sequence |
| 6 | Human LGALS8 scr ctrl | GCTTCGCGCCGTAGTCTTA (SEQ ID NO: 7) | — | Non-target sequence |

Murine Model

NOD-SCID IL-2Rγ-deficient (NSG) mice were used for in vivo tumorigenicity experiments. Age-matched mice of at least 6-weeks were used for experiments. Both male and female mice were equally used for the studies to account for any potential gender-related variability. All experiments were conducted as per FIU IACUC protocol. For limiting dilution analysis, mice were inoculated with A375 EV and GCNT2 OE cell variants and A2058 Src and KD variants subcutaneously from $1\times10^3$ to $1\times10^5$ into the flank of NSG mice. Tumor volume was calculated using the formula: [tumor volume $(mm^3)$=(length×(width)$^2$×0.5]. Tumor growth was assessed every 2-4 days by calipers.

Immunohistochemistry of GCNT2

Archival FFPE-human normal skin, nevi or melanoma tissue microarray (TMA) sections were kindly provided by Dr. Richard Scolyer (Melanoma Institute of Australia). Sections were deparaffinized in xylene; dehydrated with 100%, 95% and 75% ethanol and deionized water; placed in antigen retrieval solution; and boiled at 100° C. for 20 mins. Sections were then stained with 1:500 dilution of GCNT2 primary antibody (Sigma-Aldrich) for 30 mins at 37° C. Leica Bond Polymer Detection Kit (Leica) was used for GCNT2 antibody detection. The polymer-HRP secondary antibody was incubated for 15 mins at room temperature. Hematoxylin was used as counterstain and images were acquired using Nikon eclipse Ti microscope and Nikon FDX-35 digital camera. TMA "grade" scoring was performed as follows. Individual cores of GCNT2-stained TMAs were excluded if they were absent of skin/melanoma tissue or tissue quality deemed unsuitable for review. Melanoma cells and random fields in nevi/melanoma were identified, confirmed, and graded by a pathologist in blinded manner. Greater than 100 cells/specimen were analyzed and semi-quantitatively graded as 0 (no stained cells); 1 (1-25% cells positive); 2 (25-50% cells positive); 3 (50-75% cells positive); or 4 (75-100% cells positive). Similarly, for TMA "intensity" scoring, random fields in nevi/melanoma were analyzed, where over 100 cells/specimen were assessed and semi-quantitatively graded as 0 (No staining); 1 (Faint staining); 2 (Moderate staining) and 3 (Dark staining). Matched clinical data was then assigned to stained samples—Alive No Recurrence, Alive with Melanoma, and Dead with Melanoma. Statistical significance was analyzed via Cochran-Armitage Trend Test (p value<0.05).

ELISA of Gal-8 in Melanoma Patient Serum

Melanoma patient samples were obtained from the Biospecimen Repository Facility at Miami Cancer Institute Baptist Health-South Florida and used for Gal-8 expression analysis by ELISA. Peripheral blood samples were collected from patients with melanoma at the following stages of disease: 0 (n=1), I (n=5), II (n=1), III (n=2), IV (n=4). Peripheral blood collected in non-EDTA coated tubes were allowed to coagulate at room temperature for 1 hour. Post incubation, samples were centrifuged at 300 g for 5 min at 4° C. for serum collection. Gal-8 levels were measured in patient sera using commercially available Gal-8 ELISA Kit (Sigma) per manufactures protocol. Briefly, serum dilution of 1:1 and 1:2 was performed using assay buffer. Standards were prepared according to manufacturer's protocol. Samples and standards were loaded in anti-Gal-8 antibody coated plates and incubated overnight with gentle shaking followed by detection antibody incubation. Next, wells were incubated in TMB (3,3',5,5'-Tetramethylbenzidine) substrate for 30 mins followed by addition of ELISA stop solution and read at 450 nm.

Glycome Gene Expression Analysis

RNA was isolated for sequencing from A375, A2058 and SkMel5 cells grown under chronic hypoxia (1% oxygen) and normoxia conditions and distributed to the Genomics Core Facility at University of Miami Miller School of Medicine for RNAseq analysis. A375, A2058 and SkMel5 cells were grown under hypoxia (1% oxygen) until cells were able to proliferate with no visible signs of cell death. On the day of RNA isolation cells were washed in PBS and RNA isolation performed using RNeasy® plus mini kit (Qiagen) per manufacturers protocol. RNA sequencing was performed in the John P. Hussman Institute for Human Genomics, Center for Genome Technology Sequencing Core. Extracted total RNA was quantified via Qubit fluorometric assay (ThermoFisher) and qualified on the 2100 Bioanalyzer (Agilent). For RNA samples with RNA integrity scores (RIN)>6, 600 ng of total RNA was used as input for the NuGEN Universal Plus mRNA-Seq kit (Tecan Genomics) per the manufacturer's instructions to create poly-A selected RNA and globin depleted sequencing libraries. Following quantification of libraries via qPCR they were combined into equimolar pools and sequenced to more than 30 million raw single end 100 bp reads on the Illumina NovaSeq 6000. Resulting FASTQ files were processed with a bioinformatics pipeline including quality control, alignment to the GRCh38 human reference genome with STAR aligner v2.5.2a2, and gene quantification performed with the Gene Counts STAR function against the GENCODE v35 annotation gene set. Count data were input into edgeR software for differential expression analysis. Counts were normalized using the trimmed mean of M-values (TMM) method to account for compositional difference between the libraries. Differential expression analysis between groups was performed for paired samples adjusting for differences between individuals using an additive linear model with individual as the blocking factor. Specifically, analysis was focused on glycome-associated genes consisting of glycosyltransferases, glycoproteins, glycan-binding proteins, and other proteins necessary for the process of glycosylation, such as chaperones and nucleotide-sugar transporters. For this, we used the generalized linear model likelihood ratio test (glmLRT) implemented in edgeR. Protein coding genes with a nominal p-value (FDR)<0.05 and the average log counts per million across the samples of at least 0 were considered differentially expressed. Raw FASTQ and gene count matrix are available in the GEO GSE188986.

RT-qPCR Analysis

RNA samples from MM cells grown under normoxia or hypoxia were used to assess gene expression of TIC markers and candidate glycome factors identified in RNAseq analysis. A375 and A2058 cell lines were cultured for 24 h in normoxic and hypoxic conditions. Cell media was aspirated, and RNA was isolated using RNeasy Plus kit (mini) (Qiagen) per manufacturer protocol. Isolated RNA was converted to cDNA using SuperScript™ VILO™ cDNA synthesis kit (Invitrogen). Real-time quantitative PCR was then performed with TaqMan™ fast advanced master mix (Applied Biosystems) and TaqMan primers to amplify genes (GCNT2, KLF4, NGFR, MITF, and internal control 18S). Assays included Taqman master mix per manufacturer's protocol. Alterations in Gal-8, NCAM, and FUT11 were also assessed utilizing RT-qPCR as detailed above (LGALS8, NCAM1, FUT11, and 18S internal control).

Immunoblotting

Protein expression was assessed in lysates from MM cells grown under normoxia or hypoxia by Western blot analysis. Cells were lysed in Pierce™ RIPA buffer (Thermo Scientific) with protease and phosphatase inhibitor cocktail (Thermo Scientific). After a 30 min incubation on ice, cell lysates were centrifuged for 10 mins at 10,000 RPM in 4° C. Protein concentrations were calculated using Pierce™ BCA protein assay kit (Thermo Scientific) per manufacturer protocol, and equal protein amounts from each sample were prepared with Laemmli SDS sample buffer (Alfa Aesar). Samples were boiled for 5 mins and subsequently loaded on a 4-12% gradient SDS PAGE gel (BioRad) for electrophoresis. Separated proteins were transferred to polyvinylidene fluoride (PVDF) membranes (Millipore), blocked for 1 h at room temperature with Intercept® (TBS) blocking buffer (LI-COR), and incubated overnight at 4° C. with primary antibodies. Membranes were later washed and incubated with IRDye® anti-rabbit secondary antibody (LI-COR) for 1 h at room temperature. A LI-COR imager (LI-COR Biosciences, Lincoln, NE) was used to analyze blots.

Anti-HIF-1α ant-body (Cell Signaling) was used to confirm for hypoxia induction in lysates of A375 and A2058 cells. A375 and A2058 cells were also incubated with Gal-8 (20 µg/ml) and levels of NGFR (Abeam) were assessed by immunoblotting via the above protocol. β-actin (Abcam) was used as control. A375 and A2058 cells with Gal-8 KD were similarly grown under hypoxia and NGFR (Abcam) levels were assessed by immunoblotting.

A2058 cells with GCNT2 KD and control Scr cells were first serum starved overnight and incubated with Gal-8 (10 µg/ml) for 15 minutes and 30 minutes in serum free media. Cells were harvested for immunoblotting for AKT pS473 and total AKT (Cell Signaling)

Flow Cytometry

To analyze surface and intracellular expression of TIC markers and glycome structures, flow cytometry was performed using validated antibodies and methods as we routinely describe. Cells were harvested using Accutase (Fisher), washed with PBS and resuspended in anti-human CD271 (NGFR) (Biolegend) or NCAM (Biolegend) and Aqua Live/Dead stain for 30 minutes on ice. Single-color, isotype, and unstained controls were also prepared for validation. Cells were washed and subsequently resuspended in 2000 of PBS for analysis. For assessing i-linear glycan expression on cell surface, A375 and A2058 cells were harvested using Accutase, washed in PBS and subsequently treated with 125 mU/ml neuraminidase (sialidase) (Roche) for 2 h at 37° C. Cells were then stained for 45 minutes on ice with primary OSK28 antibody followed by secondary anti-human IgM-APC (Biolegend) and Aqua Live/Dead (Fisher). To analyze total Gal-8 levels, cells were lifted and stained with Aqua Live/Dead stain followed by fixation and permeabilization (kit) and stained with Gal-8 primary ab for 45 minutes. Cells were then washed and incubated with secondary rabbit IgG ab (AF647) for 30 mins, washed and analyzed by flow cytometry. For assessing external rhGal-8 binding cells were lifted with Accutase and incubated with rhGal-8 (R&D) for 30 mins, 10 ug/ml. Cells were then washed and stained with anti-Gal-8 ab as described and analyzed by flow cytometry. Flow cytometry was performed with BD FACSCelesta™ (BD Biosciences).

Gal-8 Affinity Chromatography

A375, A2058, A375 EV, A375 GCNT2 OE, A2058 Scr, and A2058 GCNT2 KD cells were used for Gal-8 affinity chromatography assay. Glutathione S-transferase (GST)—tagged Gal-8 (SinoBiologicals, Beijing, China) was used at 10 µg/ml concentration with reduced glutathione magnetic beads (Pierce) to isolate Gal-8 ligands per manufacturers protocol. Briefly, cells were plated 24 hrs prior to collection, with at least 10 million cells plated per cell type. Cells were first lifted using 1 mM EDTA (Invitrogen), washed in PBS and lysed using IP lysis buffer (Pierce). Lysates were quantified using BCA and 1 mg of protein was incubated with 10 µg/ml of Gal-8-GST and Glutathione magnetic beads at room temperature for 2 hours. After 2 washed in wash buffer (125 mM Tris-HCl, 150 mM NaCl, 1 mM DTT, 1 mM EDTA, pH7.4), elution buffer (50 mM glutathione, reduced (Product No. 78259) in Equilibration/Wash pH 7.4-pH 9 resulted in higher yield) was used to collect Gal-8 ligands and analyzed by mass-spectrometry and immunoblotting. Anti-CD44 antibody (Cell Signaling) was used to confirm CD44 as a Gal-8 ligand using immunoblotting as described above. Lactose (200 mM) was used as control for the affinity chromatography. For assessing the role of N-glycans in CD44's interaction with Gal-8, peptide N-glycanase F (PNGase F) (New England Biolabs) was used under non-denaturing conditions to treat eluates prior to Gal-8 affinity chromatography as per manufacturer's protocol. N-glycosylated CD44 was then confirmed as a ligand by immunoblotting.

Proteolysis and NanoLC-MS/MS Analyses.

Following Gal-8 affinity chromatography, proteins in the eluate were reduced in 5 mM DTT in 50 mM ammonium bicarbonate for 30 mins at 37° C. and alkylated with iodoacetamide (IAA) for 1 hour at room temperature in the dark. IAA was quenched by adding DTT to a final concentration of 20 mM. Next, trypsin (Proteomics Grade) was added to the sample a ratio of 1:20 (enzyme: protein), and proteins were incubated at 37 C for 12 hours. Samples were subsequently dried under vacuum and resuspended in 100 µL 1% acetonitrile and 0.1% formic acid in water and desalted using a Pierce C18 tip (Thermo Fisher Scientific™) and dried again. Nano liquid chromatography (nLC) tandem mass spectrometry analyses were performed on an Orbitrap Eclipse Tribrid Mass Spectrometer with an online EASY nLC 1200 system (Thermo Fisher Scientific™). An Acclaim PepMap 100 (75 µm, 2 cm) trapping column and a PepMap RSLC C18 analytical column (2 µm, 100 Å, 75 µm×15 cm) were employed for chromatographic separation. The following gradient was utilized for peptide separation: starting conditions 2% B, 2-6% B from 0-5 mins, 6-35% B from 5-75 mins, 35-60% B from 75-80 mins, 60-95% B for 30 sec, and 95% B for 9.5 min (solvents A and B consisted of 1% acetonitrile/99% water+0.1% formic acid and 80% acetonitrile/20% water+0.1% formic acid, respectively). All MS analyses were performed in positive mode and spectra were acquired using the Orbitrap. For proteomic analyses, MS1 scans were acquired using the following parameters: RF lens 30%; resolution 120,000; m/z range 375-2000; cycle time 3 sec; 50 msec injection time; AGC target 4×105; 1 μscan. For MS2 scans, peptides with charge states 2-6 were selected; min. intensity 2×104; and dynamic exclusion of 1 min. An isolation window of 1.2 was used. Higher-energy collisional dissociation (HCD) at 30% collision energy, and a maximum injection time of 45 msec, and first mass at m/z 130 were used. MS spectra were recorded as profile spectra, and MS2 as centroided spectra. Peptides and proteins were assigned using Proteome Discoverer (Thermo Scientific™) and all searches were performed against the Homo sapiens UniProt Reviewed (Swiss-Prot) protein database and Sequest search algorithm, with trypsin selected as the protease, up to 2 missed cleavages considered, and carbamidomethylation (C) set as a fixed modification. Search results were filtered to a 1% false discovery rate (FDR).

Statistical Analysis

Prism 8.0 software (GraphPad) was used for statistical analysis. For tests involving two groups, unpaired two-tailed Student's t-test was used. For patient samples, appropriate tests were chosen for assumptions of normality. Throughout, error bars depict Standard Error of Mean (SEM). For analysis of 2 groups with repeated measures, 2-way ANOVA was used followed by Sidak's multiple comparison analysis (in vivo assay). P value of <0.05 was considered significant.

Example 1—Loss of GCNT2 Correlates with Reduced Patient Survival in MM Patients and Promotes Expression of TIC Marker in MM Cells To assess consequences of GCNT2 expression in MM patients and disease outcome, 64 samples from MM patients that died from melanoma were stained for GCNT2 by immunohistochemistry. Stained slides were grouped into low, medium, and high depending on the GCNT2 staining score (0-3: 0—No staining, 1—Light staining, 2—Moderate staining, and 3—Dark/strong staining). Patients with GCNT2 expression from 0-1 staining level presented with significantly decreased survival compared to patients with high GCNT2 expression ($p<0.04$) (FIGS. 1A and 1B).

To explore the pathobiological consequences of GCNT2 loss in MM, human MM A375 (low GCNT2 expression) and A2058 (moderate GCNT2 expression) cells engineered to express or silence GCNT2 were utilized. Corresponding overexpressed (OE) or knockdown (KD) GCNT2 variants in A375 and A2058 cells, including their empty vector (EV) and Scrambled control (Scr) variants, respectively, were generated by lentiviral transduction; and GCNT2 expression was validated by RT-qPCR (FIGS. 1C and 1D). The expression of a common molecular feature of TICs, NGFR/CD271 was first analyzed. GCNT2 OE exhibited significantly decreased ($p<0.01$), (FIGS. 1E and 1F), while GCNT2 KD1 and KD2 resulted in increased NGFR expression ($p<0.01$) (FIGS. 1G and 1H).

Figure 1J:
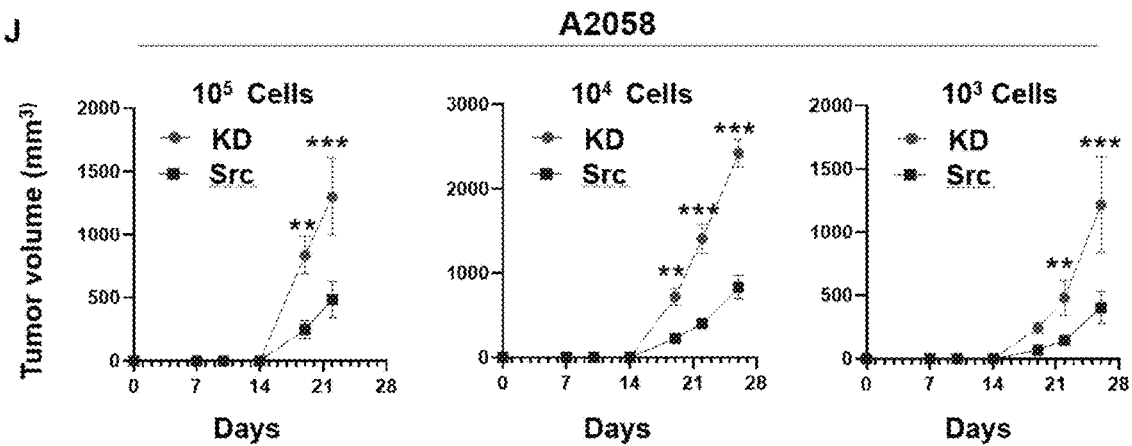

To investigate GCNT2's role in TIC generation, in vivo limiting dilution assays were performed in NOD-SCID IL-2Rγ-deficient (NSG) mice using GCNT2-engineered MM cells. A375 GCNT2 OE and A2058 GCNT2 KD cell lines were injected subcutaneously in the flank with cell concentrations ranging from $10^3$ to $10^5$ cells per mouse along with their respective controls (EV and Scr). Lower GCNT2 expression led to increased growth potential even at $10^3$, while increased GCNT2 expression hindered tumor growth even when $10^5$ cells were injected ($p<0.01$) (FIGS. 1I and 1J). Together, these results suggest that GCNT2 expression can regulate TIC potential in MM cells.

Figure 2A:
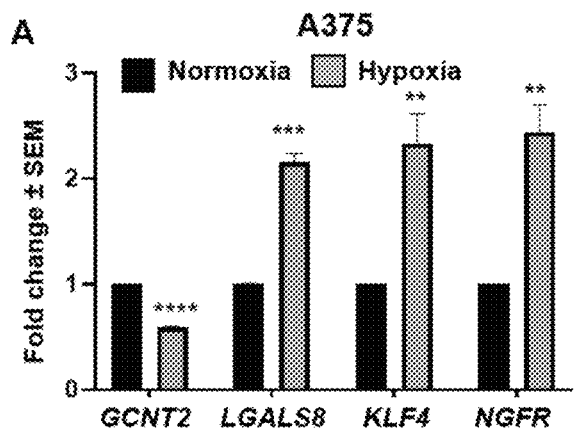
FIGS. 2A-2U. Hypoxia reduces GCNT2 expression and leads to increased surface i-linear poly-LacNAcs. RT-qPCR analysis of GCNT2 and Gal-8, KLF4, and NGFR in A375 (2A) and A2058 (2C) under normoxia and hypoxia (1% oxygen). Hypoxia was confirmed by immunoblotting HIF1α expression in A375 and A2058 cells (2B and 2D). Flow cytometric analysis of Gal-8 expression on A375 (2E) and A2058 (2F) cells grown under normoxia or hypoxia. Flow cytometric analysis of surface i-linear poly-LacNAc expression was performed on A375 (2G) and A2058 (2H) grown under normoxia and hypoxia by staining with OSK-28 antibody. For every experiment, at least 4 biological replicates were performed. (*$p<0.001$ $p<0.01$ *$p<0.05$). Partial MALDI-TOF MS spectra of permethylated N-glycans of A375 (2I) and A2058 (2J) under normal oxygen conditions. MALDI-TOF/TOF MS/MS spectra of the molecular ion at m/z 6384 from A375 (2K) and A2058 (2L) grown under normal oxygen conditions and derived from 2I and 2J respectively; or grown under hypoxic conditions (2M and 2N, respectively). The highlighted areas were inserted to assist clarity. Partial MALDI-TOF MS spectra of permethylated N-glycans of A375 (2O) and A2058 (2P) after Sial-S(α2,3NeuAcs) digestion and under normal oxygen conditions. MALDI-TOF/TOF MS/MS spectra of the molecular ion at m/z 6287 from A375 (2Q) and A2058 (2R) grown under normal oxygen conditions and derived from 2O and 2P respectively; or grown under hypoxic conditions (2S and 2T, respectively). The highlighted area was inserted to assist clarity. Circled numbers correspond to the number of LacNAc repeat losses from the $[M+Na]^+$ molecular ion. Horizontal dashed lines with an arrowhead correspond to the loss of the corresponding structure from the molecular ion (2K). All fragment ions are sodium adducts. (2U) MALDI-TOF/TOF MS/MS of hypothetical ions detected at m/z x. The main fragment ion that differentiates the i-linear poly-LacNAcs N-glycan structures from the I-branched poly-LacNAcs is the fragment ion that corresponds to a loss of two LacNAc repeats, either undecorated or with a NeuAc residue on the non-reducing side (peak b). When the relative abundance of b is compared with the relative abundance of the fragment ion that corresponds to three LacNAc repeats (peak c), a relative characterization of whether the poly-LacNAcs are either on i-linear or I-branched format can be deduced based on the ratio b to c. When this ratio (b/c) is >1 the poly-LacNAcs are principally in a i-linear format (Upper panel), while when this ratio is <1, then the poly-LacNAcs are or I-branched format (Lower panel). Intermediate values indicate intermediate states.
Figure 2B:
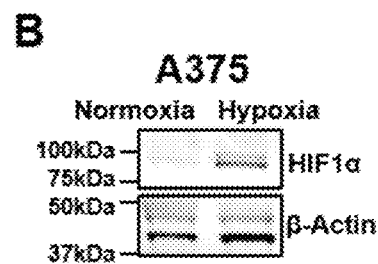
Figure 2C:
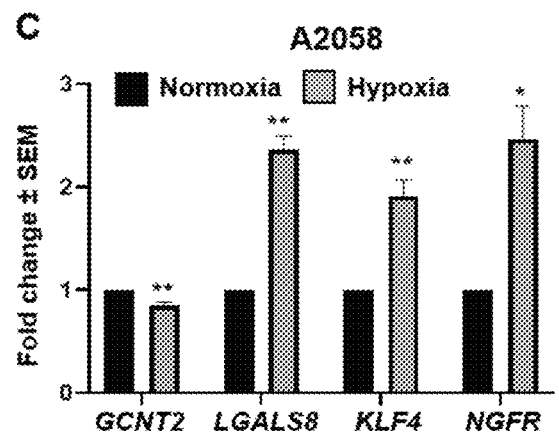
Figure 2D:
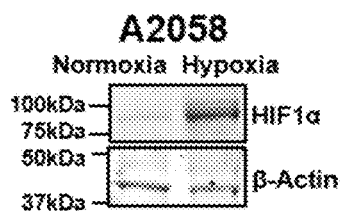
Figure 2E:
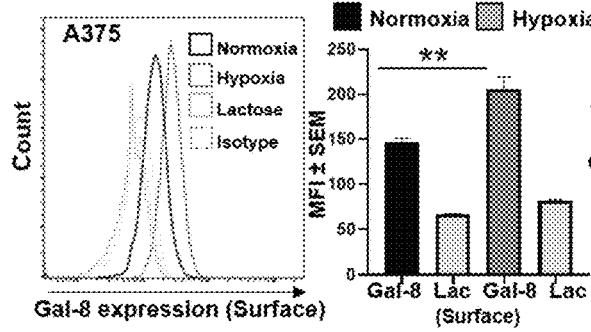
Figure 2F:
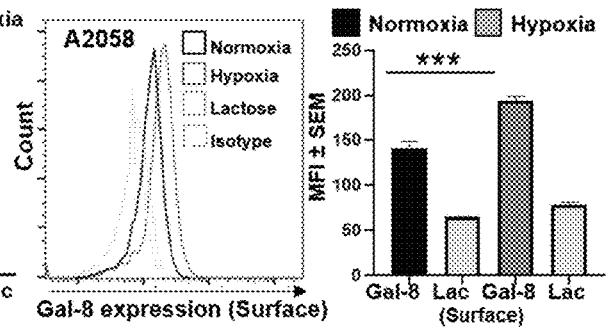
Figure 2G:
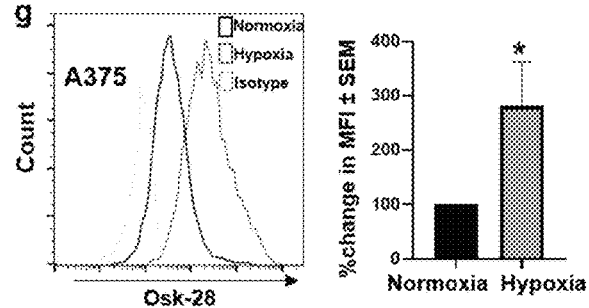
Figure 2H:
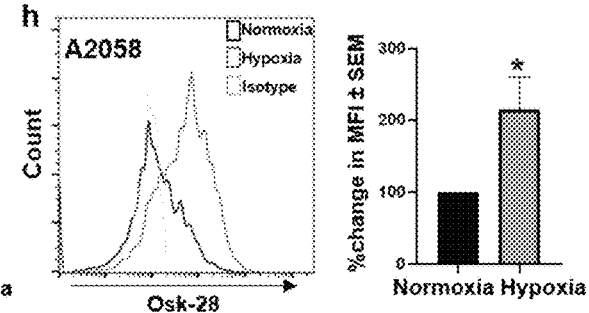

Example 2—Hypoxia Reduces GCNT2 Expression, Enhances TIC Markers and Globally Alters MM Glycobiology Tumor microenvironmental hypoxia is a major factor contributing to the establishment of TICs. MM is a highly hypoxic tumor-type with intratumoral oxygen tension of only 1.5%. To study the role of hypoxia on the MM glycome signature, human MM cells were subjected to acute (24 hrs) and chronic (>48 hours) hypoxia to assess alterations in glycosylation-related genes and their role in TIC marker expression. In addition to significant Gal-8 upregulation, acute hypoxia lowered GCNT2 expression in A375 and A2058 MM cells ($p<0.001$) along with significant elevations in known TIC markers, KLF4 and NGFR by PT-qPCR ($p<0.01$) (FIGS. 2A and 2C). Hypoxia induction was confirmed by elevated HIF1α expression by Western blot analysis (FIGS. 2B and 2D). Significant elevations in surface expression of Gal-8 and MM glycome i-linear poly-LacNAcs were also evidenced by flow cytometry with anti-i-linear poly-LacNAc moAb Osk28 of MM cells grown under hypoxia ($p<0.01$) (FIGS. 2E, 2F, 2G and 2H).

To further assess glyco-structural elevations in i-linear poly-LacNAcs under hypoxia, N-glycans from MM cells cultured under normoxic or hypoxic conditions were analyzed by matrix-assisted laser desorption ionization-time of flight mass spectrometry (MALDI-TOF MS). Human MM A375, A2058 and SK-MEL-5 cells grown under normoxia or hypoxia consisted of high mannose (data not shown) and complex N-glycan structures with extensive poly-LacNAc repeating units (reaching up to 11 total LacNAc units; m/z 8093) terminated mainly in N-acetylneuraminic acid (NeuAc) residues and minor antennal fucosylation (FIG. 3).

Figure 2I:
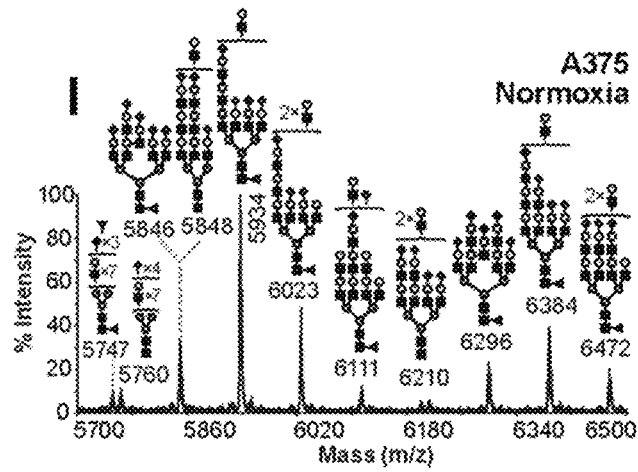
Figure 2J:
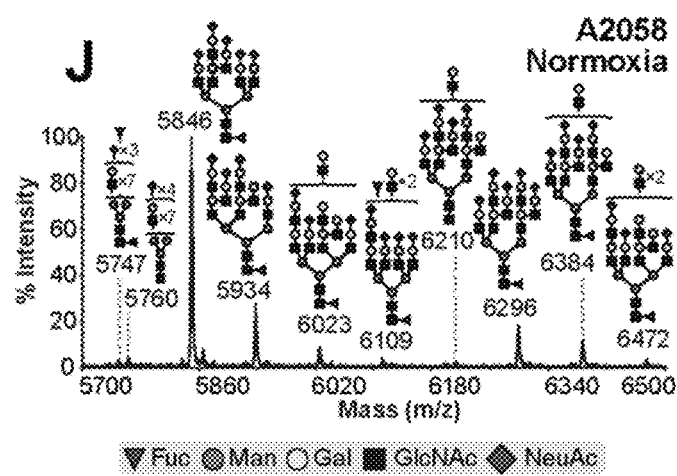

Partial annotated MALDI-TOF MS spectra of high mass N-glycans from A375 and A2058 cells under normoxia, however, revealed that A375 cells contained mainly i-linear poly-LacNAcs (FIG. 2I), whereas A2058 cells displayed principally I-branched poly-LacNAcs (FIG. 2J). These assignments were based on N-glycan molecular ion MALDI-TOF/TOF MS/MS, which helps differentiate i-linear poly-LacNAcs from I-branched poly-LacNAcs.

Figure 2K:
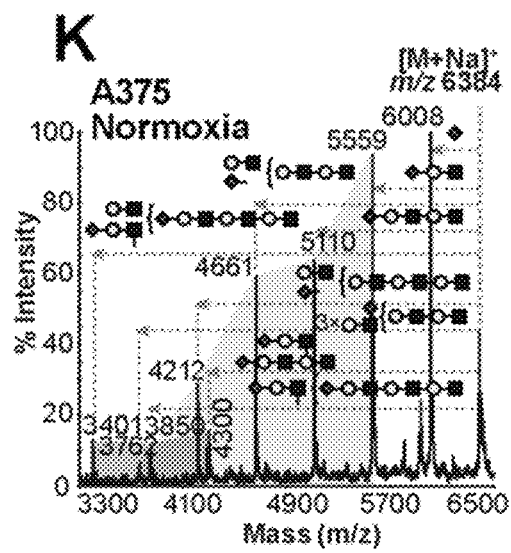
Figure 2L:
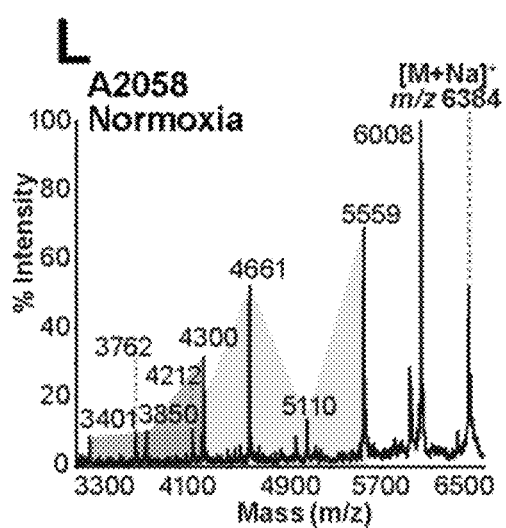
Figure 2M:
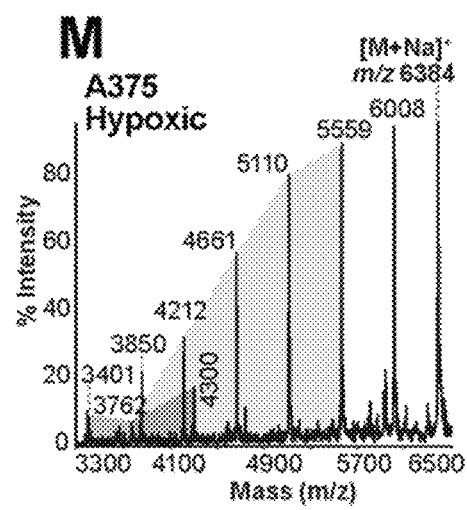
Figure 2N:
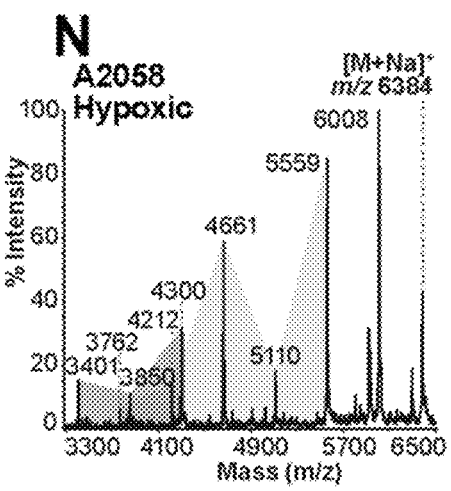
Figure 2O:
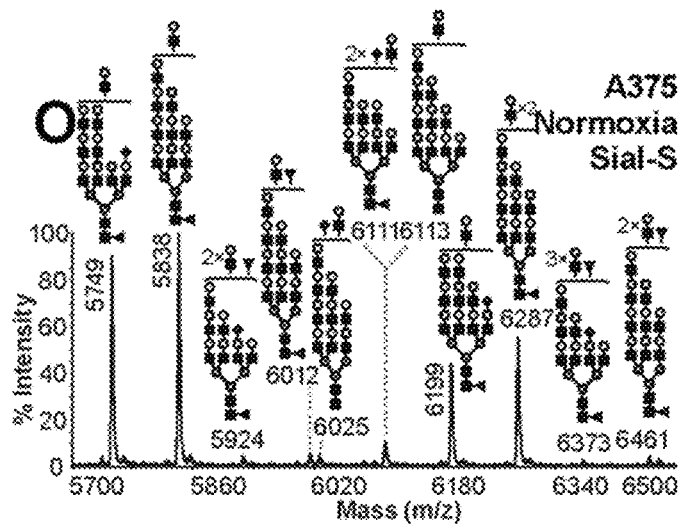
Figure 2P:
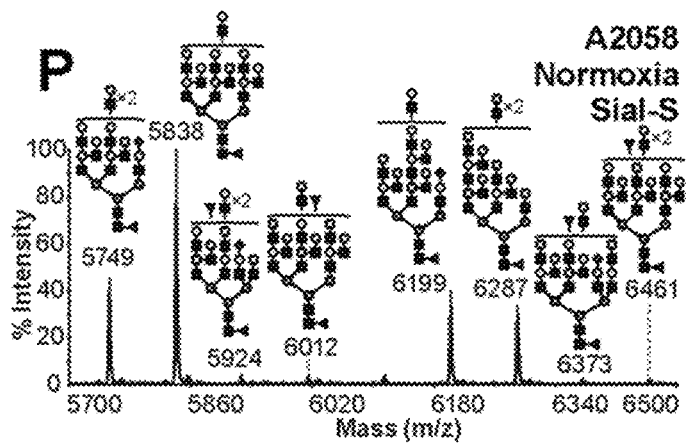
Figures 2Q, 2S:
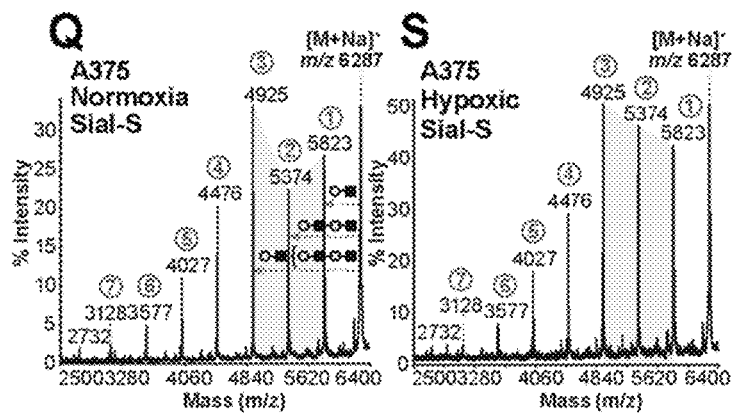
Figures 2R, 2T:
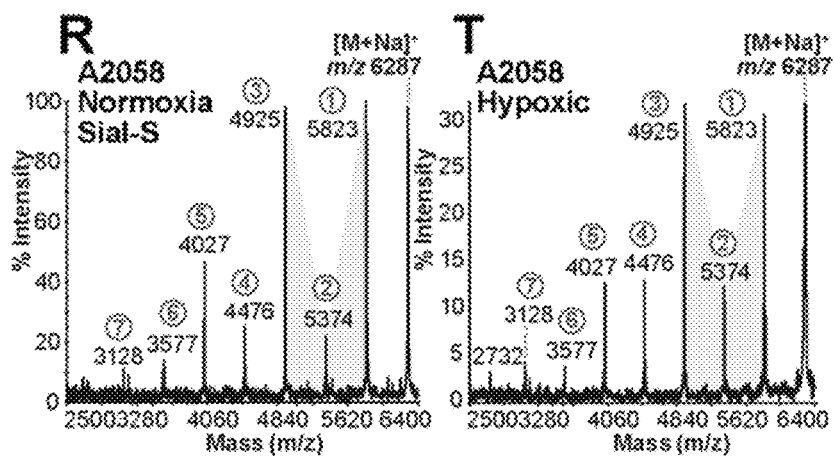
Figure 2U:
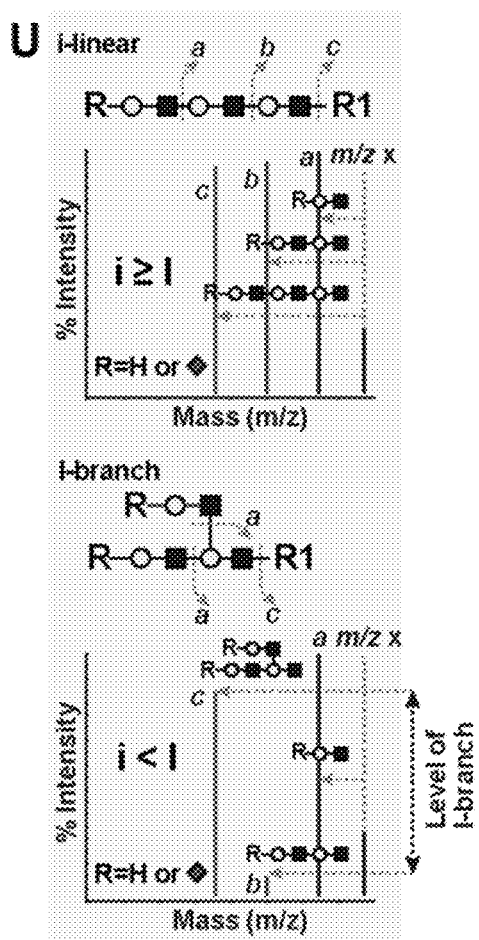
Figure 3A:
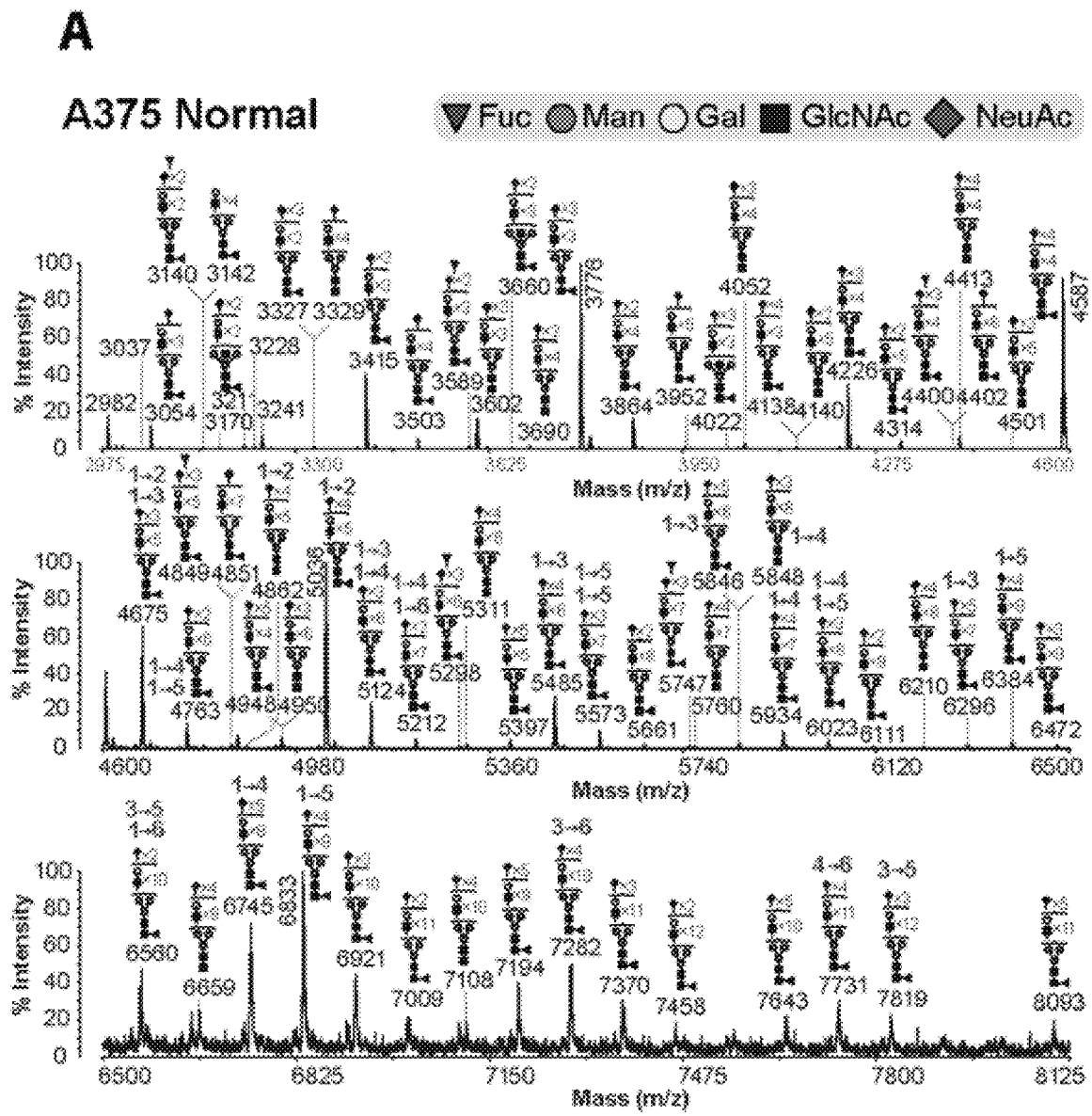
FIGS. 3A-3F. MALDI-TOF MS spectra of permethylated N-glycans of A375 (3A), A2058 (3B) and SK-MEL-5 (3C) grown under normal oxygen or hypoxic conditions (3D, 3E and 3F, respectively). MALDI-TOF/TOF MS/MS analysis was undertaken to evaluate the number of poly-LacNAcs. Results are presented above the annotated spectrum (3A) or the m/z value (in others) with light gray and gray numbers. Light gray values correspond to the minimum (before the arrow) and maximum (after the arrowhead) number on LacNAc repeats detected for the corresponding molecular ion, while gray values correspond to sialylated LacNAc repeats. For example, MALDI-TOF/TOF MS/MS analysis showed that in (3A) the molecular ion at m/z 6560 corresponded to mixture of structural isomers that contained undecorated poly-LacNAcs ranging from 3 to 5 of LacNAc units (light gray), and sialylated poly-LacNAcs, ranging from 1 to 6 LacNAc units (gray). (3A) Structures outside a bracket have not been unequivocally defined. "M" and "m" designations indicate major and minor abundances, respectively. All molecular ions are [M+Na]$^+$. Profiles of N-glycans are from the 50% MeCN fraction from a C$_{18}$ Sep-Pak.
Figure 3B:
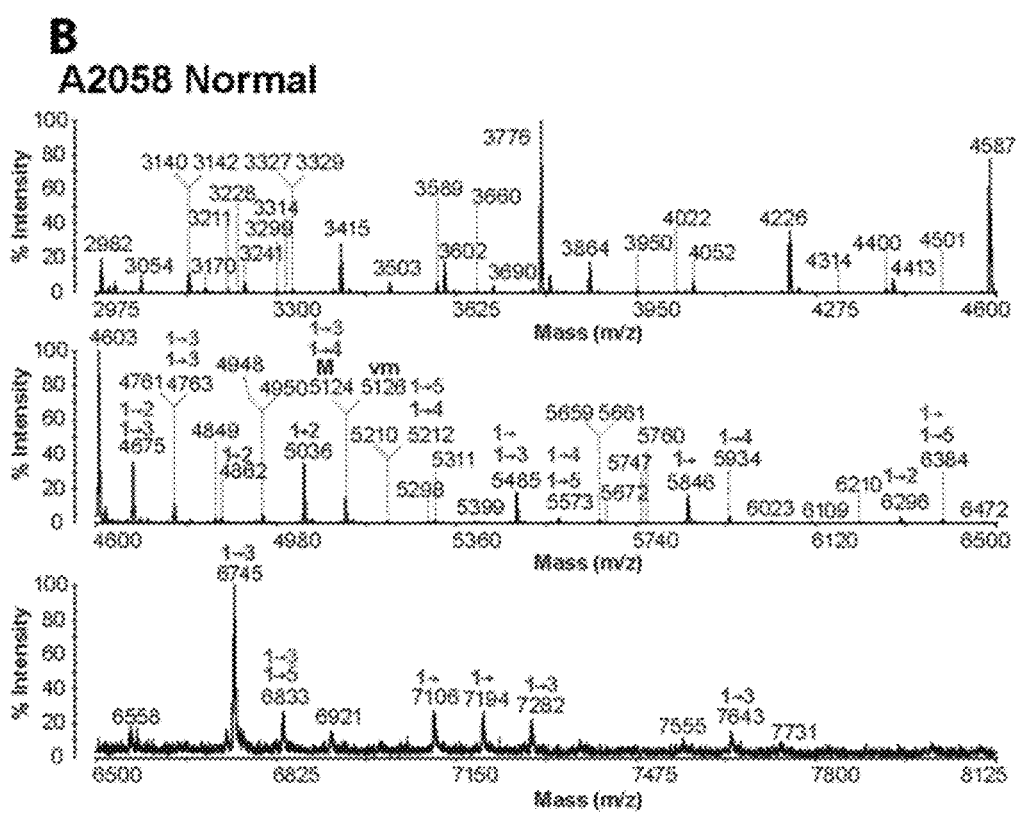
Figure 3C:
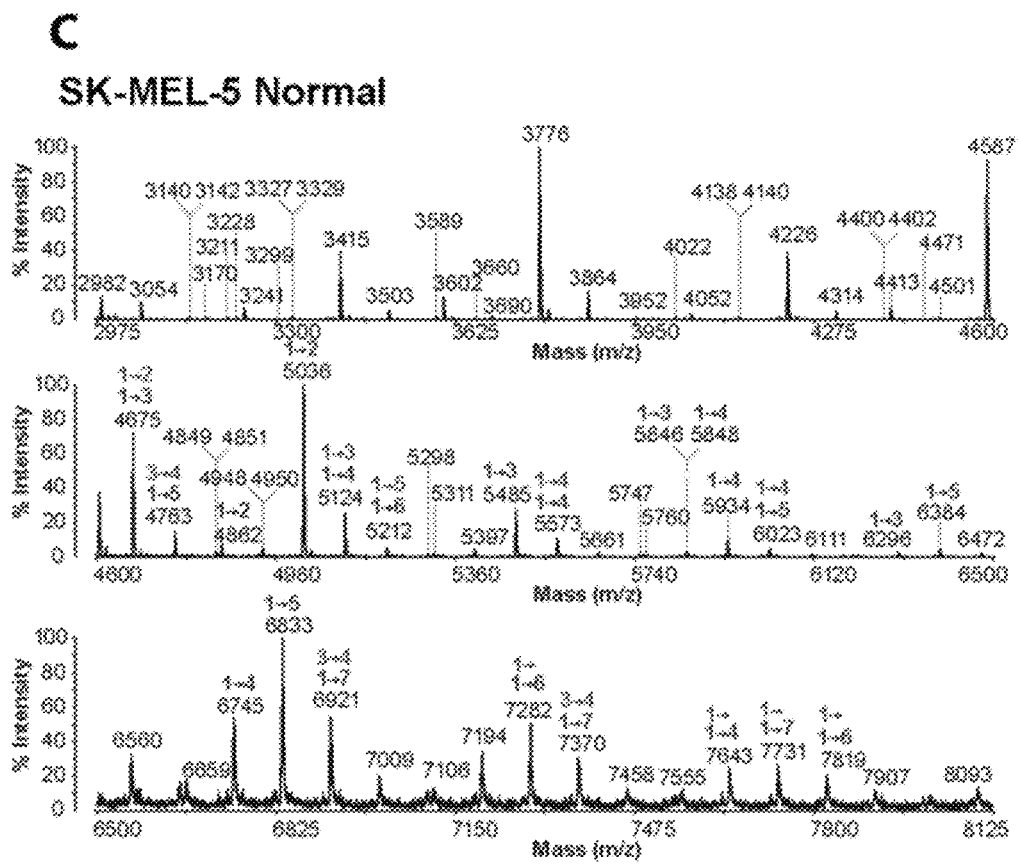
Figure 3D:
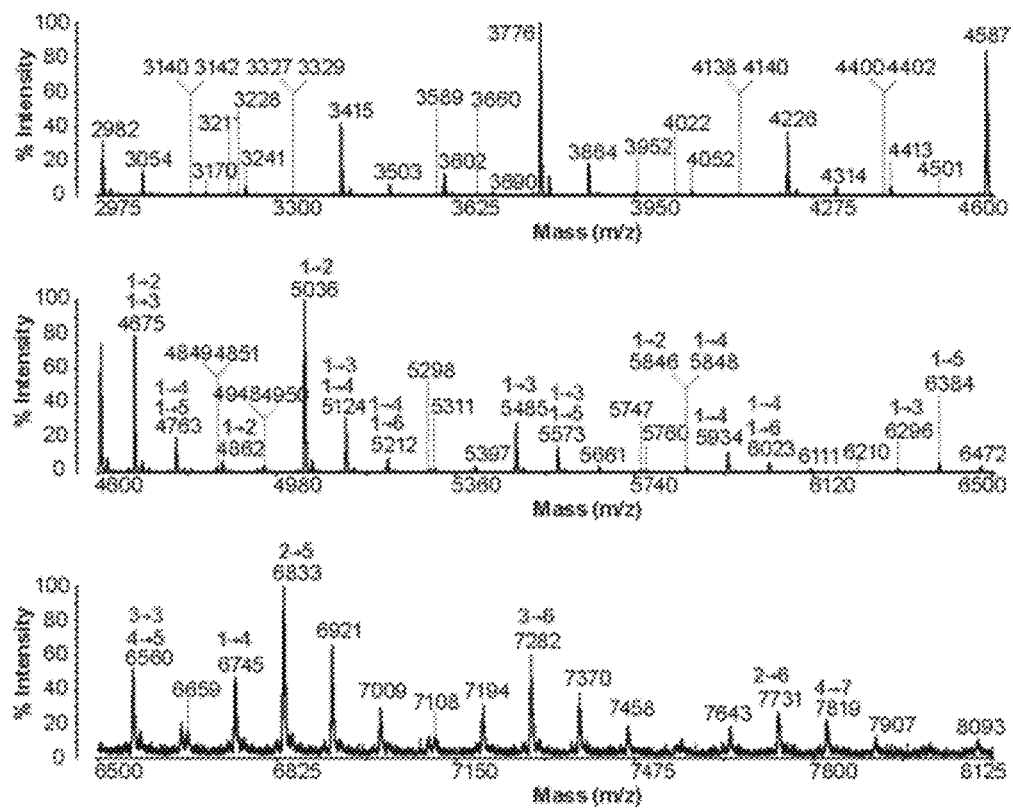
Figure 3E:
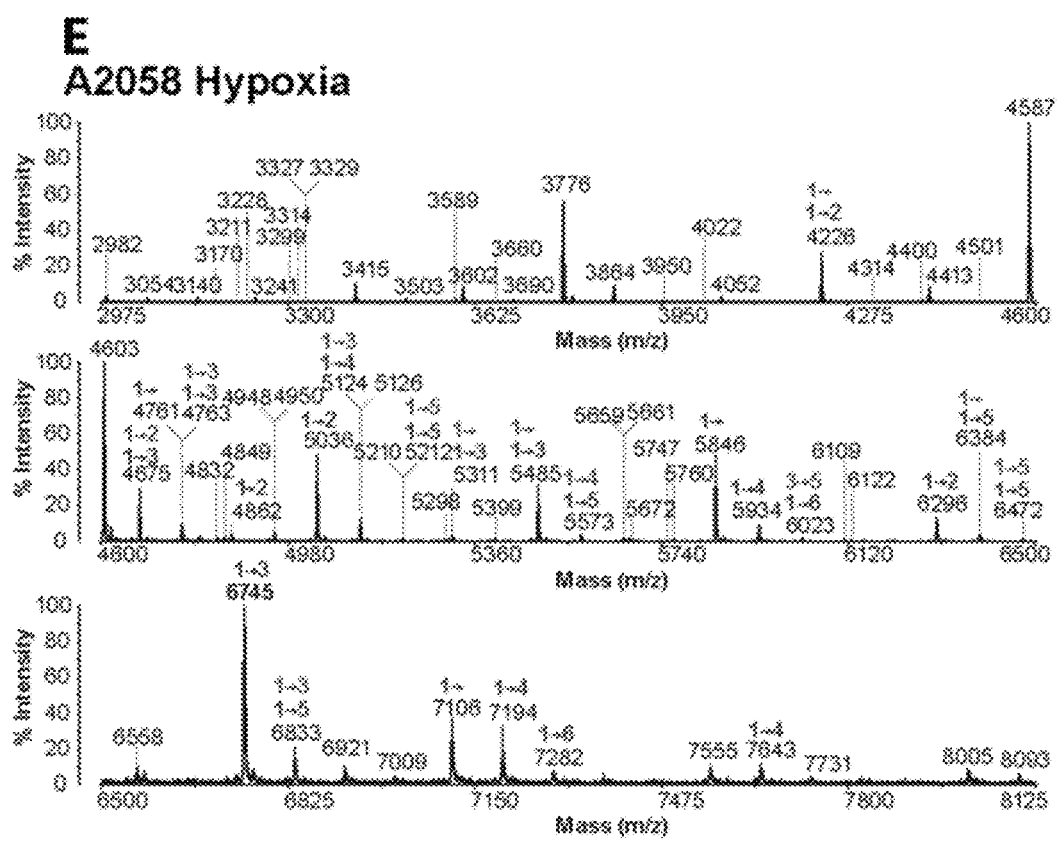
Figure 3F:
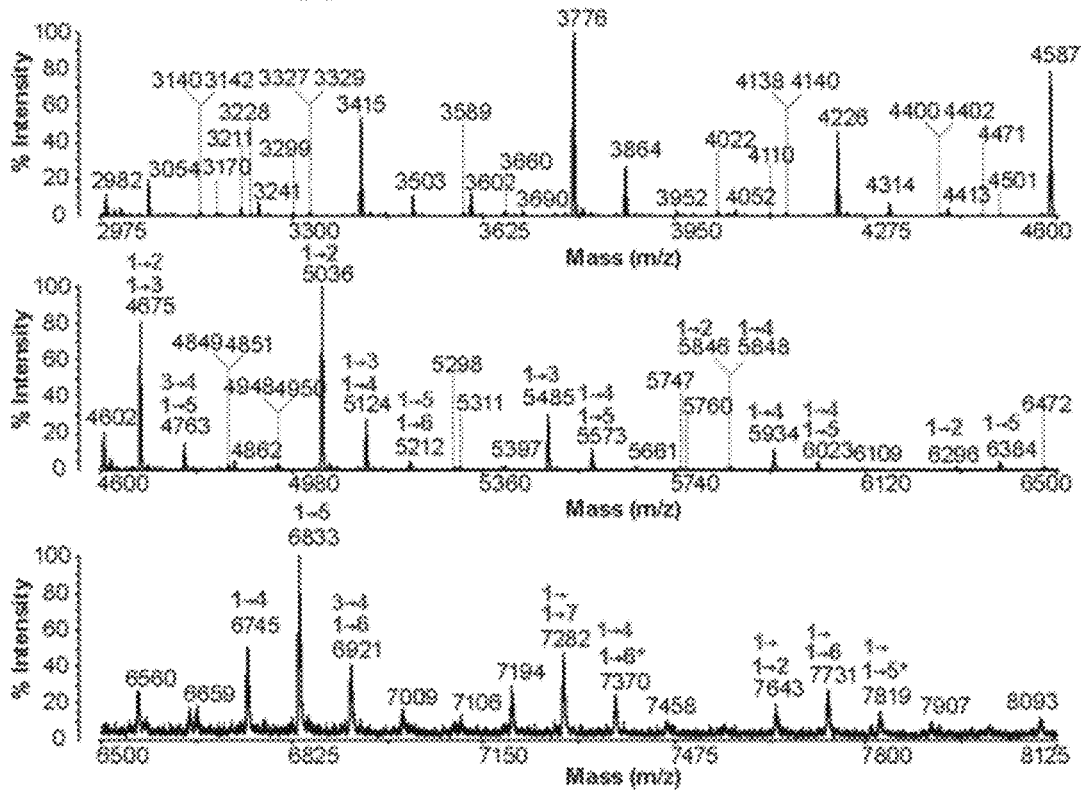
Figure 4A:
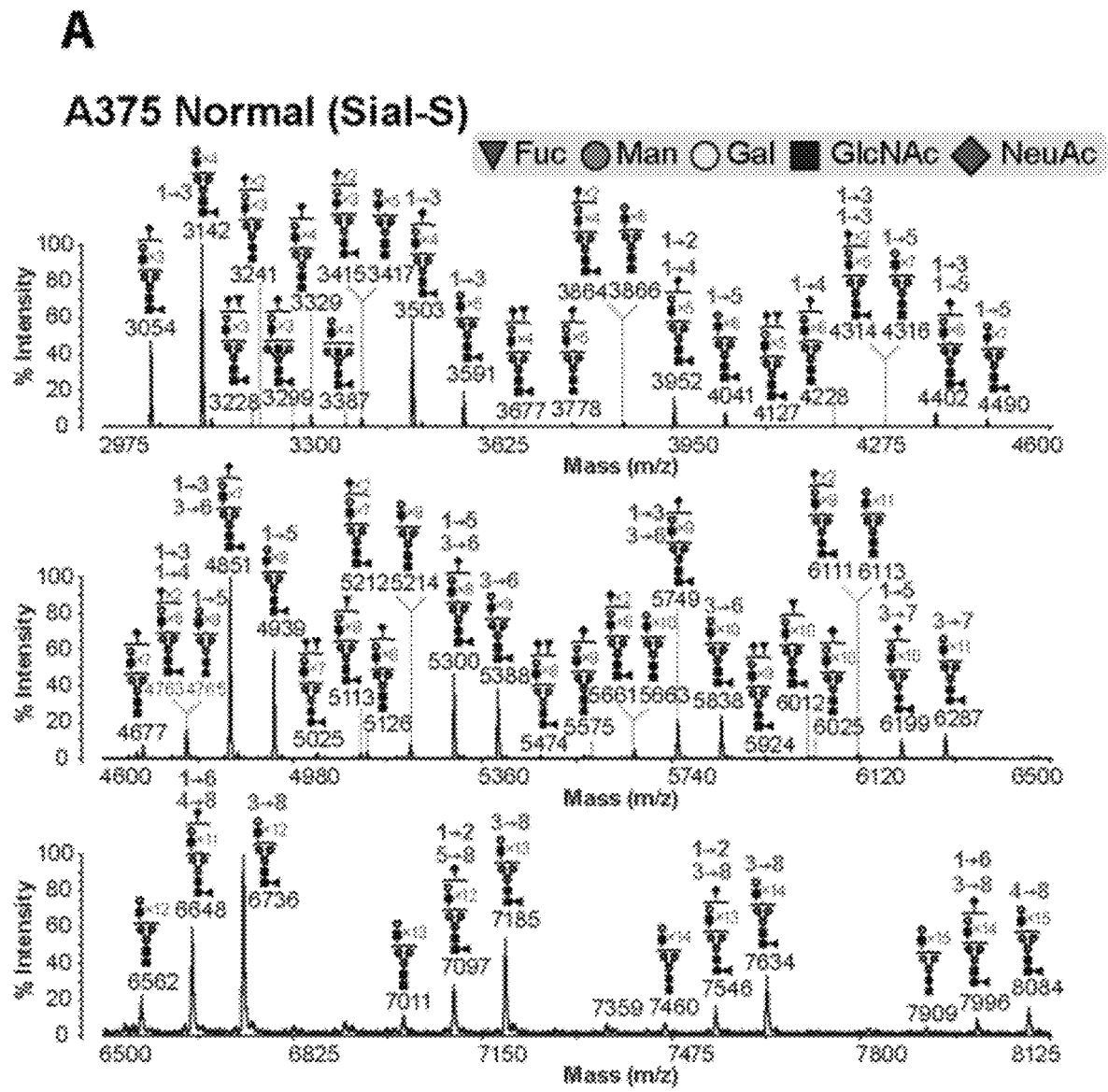
FIGS. 4A-4F. MALDI-TOF MS spectra of permethylated N-glycans, after α2,3 sialidase digestion, of A375 (4A), A2058 (4B) and SK-MEL-5 (4C) grown under normal oxygen conditions; or grown under hypoxic conditions (4D, 4E and 4F respectively). The light gray and gray values follow the same coding as in FIGS. 3A-3F.
Figure 4B:
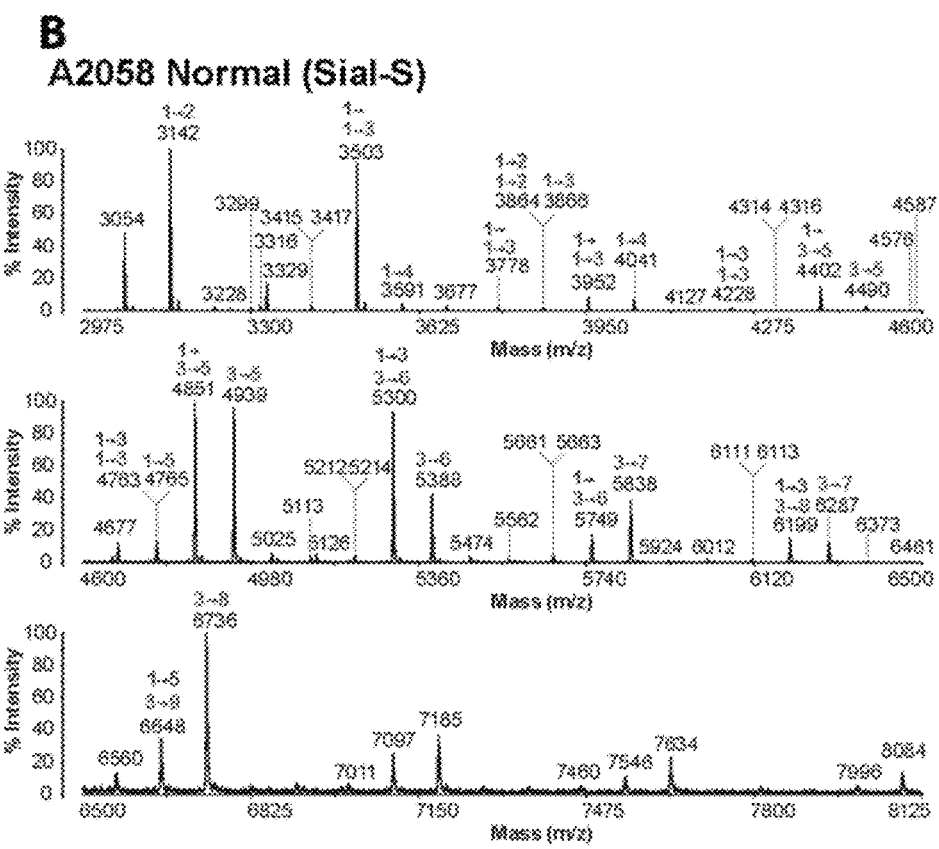
Figure 4C:
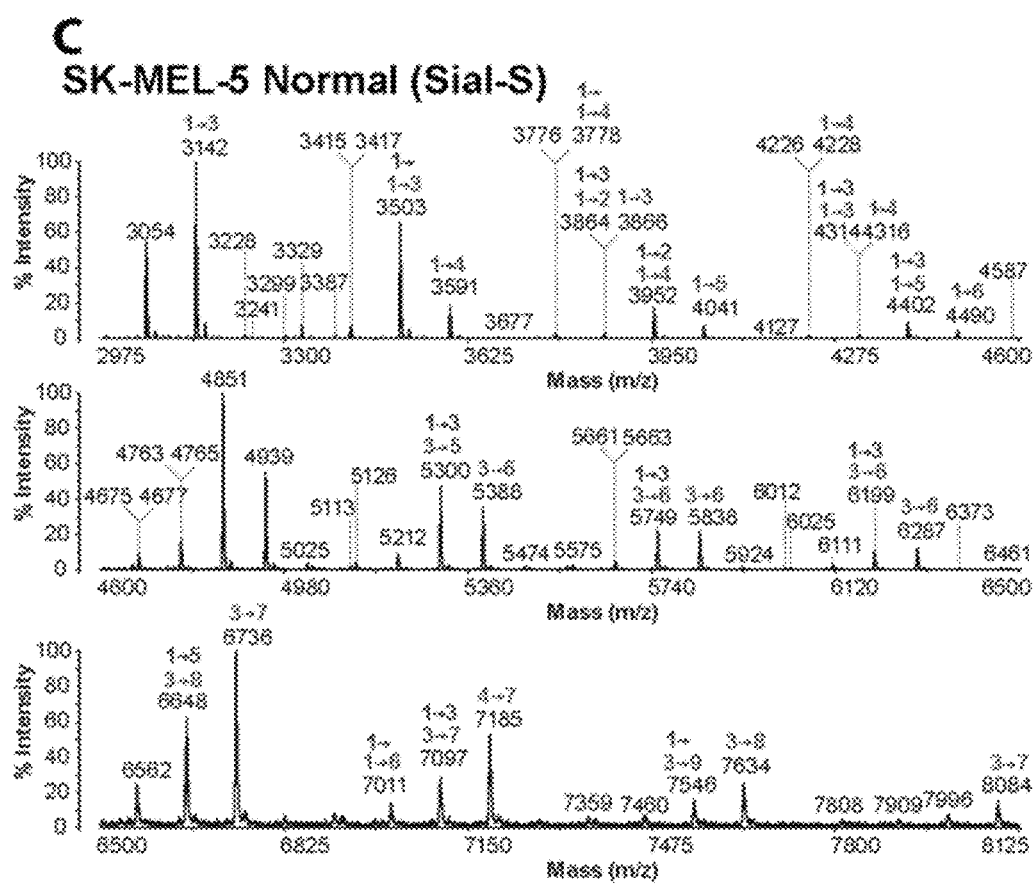
Figure 4D:
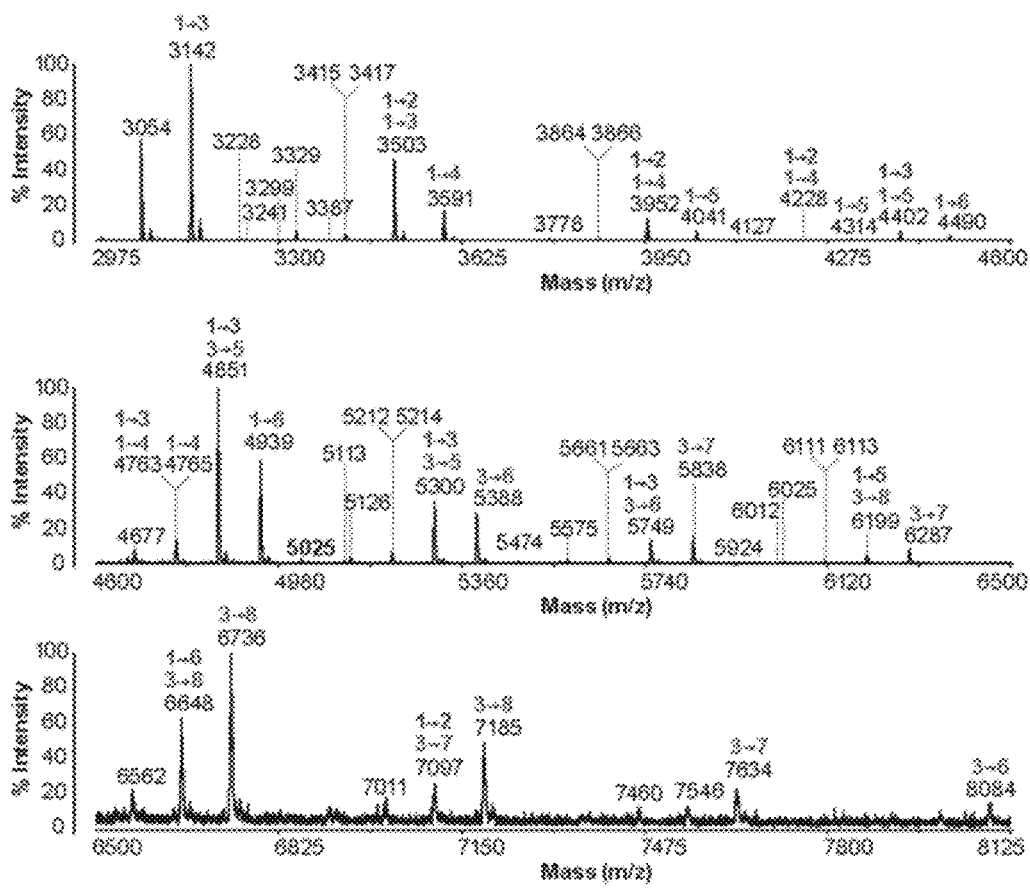
Figure 4E:
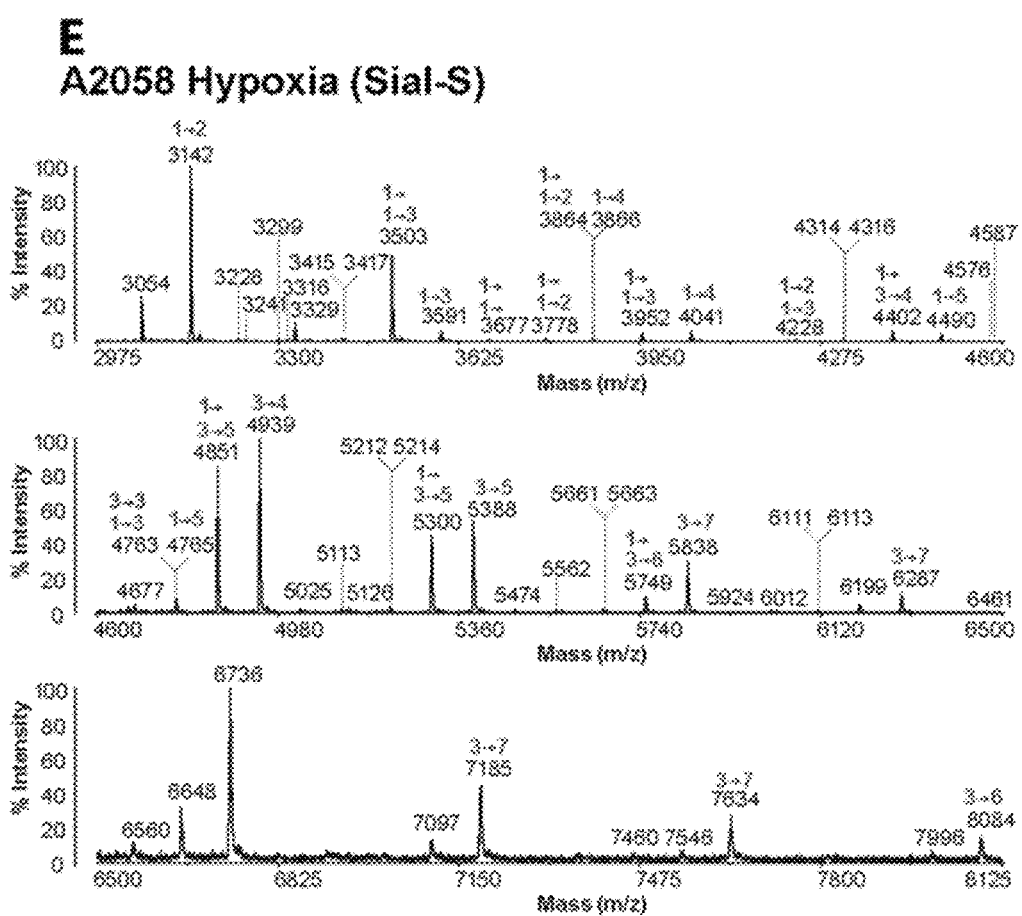
Figure 4F:
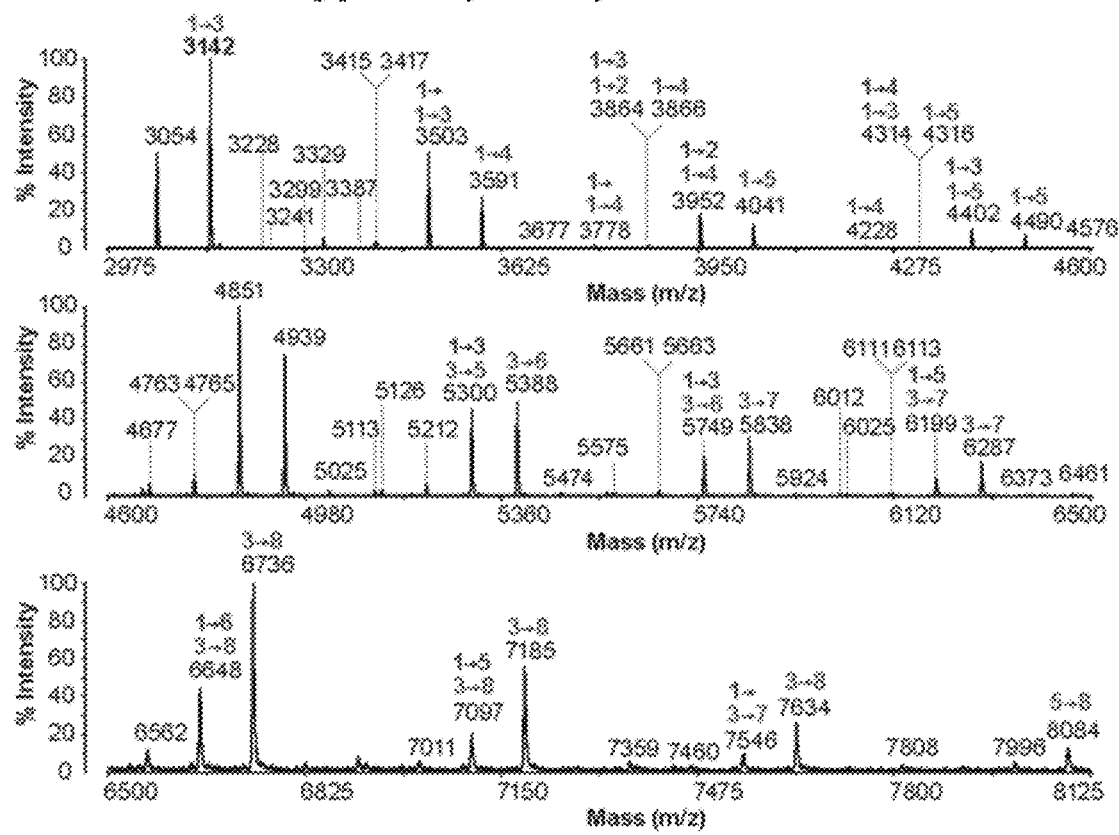

The ratio of relative abundance of fragment ions corresponding to loss of 2 and 3 LacNAc repeats was characteristic of i-linear or I-branched poly-LacNAcs (FIG. 2U, Peaks b and c, respectively). A ratio of b/c >1 corresponded mainly to i-linear poly-LacNAcs, while a ratio <1 corresponded to I-branched poly-LacNAcs. This relationship is based on the assumption that fragmentation of i-linear poly-LacNAcs, and therefore the relative abundance of either (2) or (3) LacNAc units, is relatively proportionate (FIG. 2U, Peaks b and c, upper panel); whereas fragmentation of I-branched poly-LacNAcs did not result in fragments containing (2) LacNAcs and the relative abundance of the b fragment was much less than fragment c (FIG. 2U, Peaks b and c, lower panel).

Using this interpretative model, representative N-glycans of A375 and A2058 cells grown under normoxia or hypoxia were contrasted. The molecular ion at m/z 6384 from A375 cells exhibited a relative abundance of fragmented ions corresponding to loss of (2) LacNAc repeats at m/z 5110 that was higher than those ions corresponding to (3) LacNAc repeats (m/z 4661), which was indicative of mainly i-linear poly-LacNAcs (FIG. 2K). On the contrary, the same molecular ion from A2058 cells displayed a relative abundance of fragment ion at m/z 5110 that was substantially lower than the relative abundance of ions at m/z 4661, suggesting that the ion at m/z 6384 consisted mainly of I-branched poly-LacNAcs (FIG. 2L).

Under hypoxia, while LacNAc repeats in poly-LacNAcs per N-glycan antenna was not markedly changed (FIG. 3), there was a noted increase in the ratio of i-linear to I-branched poly-LacNAcs at m/z 6384 of A375 cells (FIG. 2M). That is, the ratio of relative abundance of fragment ions at m/z 5110 to 4661 was elevated compared with cells grown under normoxia. Similarly, on A2058 cells grown under hypoxia, the ratio of relative abundance of fragment ions at m/z 5110 to 4661 was elevated compared with levels on cells grown under normoxia (FIGS. 2L and 2N). These flattening of the "V" patterns indicative of increased i-linear poly-LacNAcs were also observed for other N-glycan species and were additionally observed on N-glycan spectra from human MM SK-MEL-5 cells (data not shown). Altogether, these results suggested that hypoxia helps orchestrate signature i-linear poly-LacNAc structures on MM cells.

To determine whether hypoxia influenced sialylation on N-glycans, MALDI-TOF MS and MALDI-TOF/TOF MS/MS were conducted on N-glycans digested with α2,3 sialidase-S (Sial-S) from A375 and A2058 cells cultured under normoxia and hypoxia. Cumulative data indicated that there were no major differences in the abundance of α2,3-NeuAc residues and that the majority of the NeuAc residues at the termini of poly-LacNAcs were α2,3-linked NeuAcs (FIG. 4). Partial annotated high mass N-glycan spectra after Sial-S digestion from A375 and A2058 cells did not demonstrate any alteration in the abundance of i-linear poly-LacNAcs or I-branched poly-LacNAcs, respectively (FIGS. 2O and 2P). Furthermore, compared with Sial-S-treated N-glycan at m/z 6287 from cells grown in normoxia (FIGS. 2Q and 2R), Sial-S-treated N-glycans from cells grown under hypoxia also exhibited increases in relative abundance of i-linear LacNAcs (FIGS. 2S and 2T). These data suggested that α2,3 sialylation of N-glycans was not affected by hypoxia and did not neutralize hypoxia-dependent induction of i-linear poly-LacNAcs.

Figure 5A:
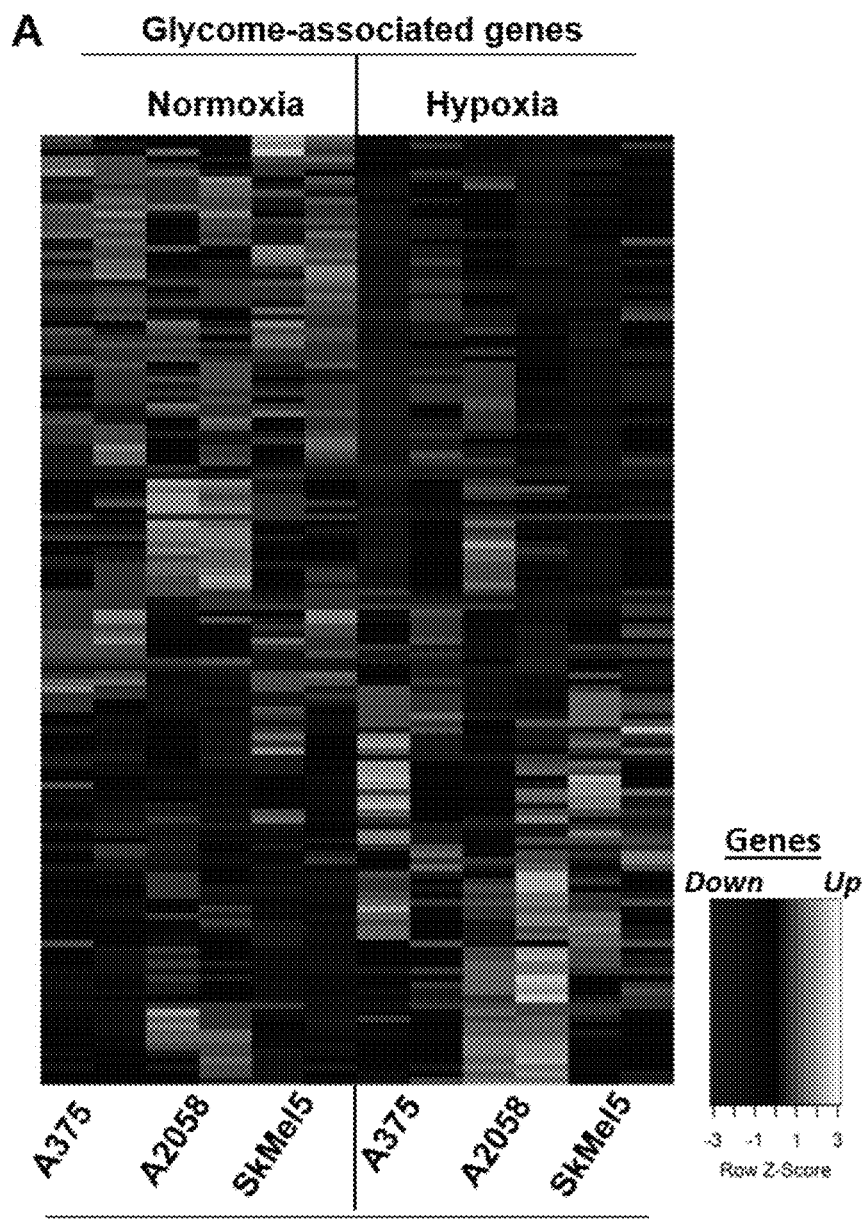
Figure 5H:
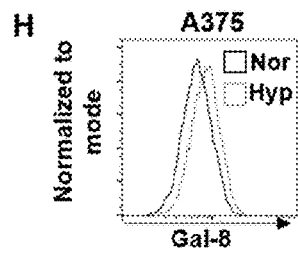
Figure 5I:
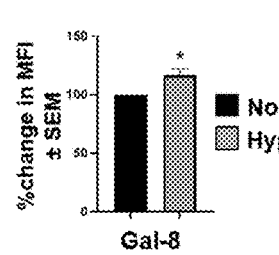
Figure 5I:
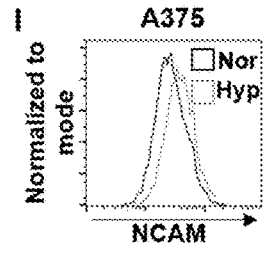
Figure 5J:
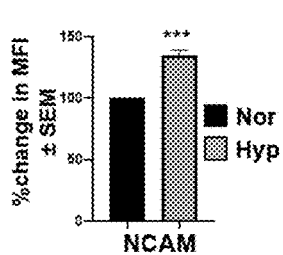
Figure 5J:
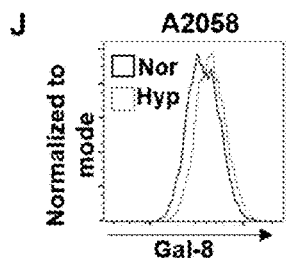
Figure 5K:
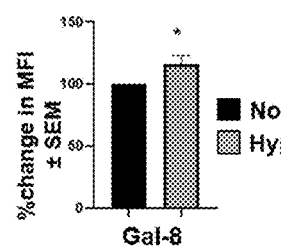
Figure 5K:
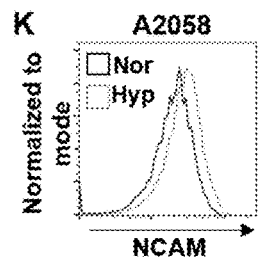

To assess other MM glycome gene alterations, including glycan-binding lectins and glycan synthesis and degradation pathways induced under hypoxic conditions, human A375, A2058, and SkMel-5 MM cells were cultured under normoxia or hypoxia and analyzed by RNA-sequencing (FIG. 5A). Upregulated and downregulated glycome genes shared among all (3) cell lines were observed.

Among cancer-associated galectins, galectin (Gal)-8 was the most upregulated galectin under hypoxia. Elevation in Gal-8 expression was confirmed by RT-qPCR (p<0.01) and flow cytometry (p<0.05) (FIGS. 5B, 5E, 5H and 5J). Among other key deregulated glycoproteins, NCAM, which is implicated in tumor formation, was increased as confirmed by RT-qPCR and flow cytometry (p<0.01) (FIGS. 5C, 5F, 5I and 5K). Alpha1,3 fucosyltransferase 11 (FUT11) was upregulated in MM cells (p<0.01) (FIGS. 5D and 5G). FUT11 is associated with cancer progression and is expressed upon HIF1α induction under hypoxia. Similarly, while Gal-1 and Gal-3 are well described pro-tumorigenic factors in melanoma progression, Gal-8 has never been associated with MM. However, in other tumor models, Gal-8 has been shown to promote growth and participate in tumor microenvironmental immune escape and metastasis formation, both characteristic of TICs.

Figure 6A:
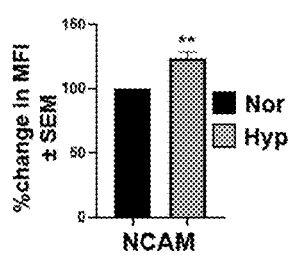
FIGS. 6A-6N. Gal-8 levels are upregulated in MM patient sera and alters signaling in MM cell lines. Flow cytometric analysis of i-linear poly-LacNAc (6A), Gal-8 binding activity (6B), and endogenous Gal-8 (6C) levels on/in MM A375 and A2058 cells was performed using OSK-28 antibody, rhGal-8, and anti-Gal-8 antibody. Flow cytometry analysis of rhGal-8-binding was performed on A375 EV and GCNT2 OE cells (6D) and on A2058 Src and GCNT2 KD cells (6E). ELISA of Gal-8 was performed on sera from normal healthy volunteers (n=5) and MM patients (n=13) (6F). Western blotting was performed on NGFR expression post 24 hours of Gal-8 treatment (20 μg/ml) of A375 (6G) and A2058 (6H) cells. A375 Scr and Gal-8 KD cells (6I and 6K) and A2058 Scr and Gal-8 KD (6J and 6L) cells were cultured under normoxia, and hypoxia. Immunoblot analysis of NGFR expression in A375 Scr and Gal-8 KD cells (6M) and A2058 Scr and Gal-8 KD (6N) cells cultured under normoxia or hypoxia for 24 hr. In vivo tumor formation assessment using A375 Gal-8 KD/Scr cells (6O). Western blot analysis of NGFR expression in A375 Gal-8 KD/Scr cells after 24 hr Gal-8 incubation (20 μg/ml) with or without Gal-8 inhibitor 100 mM lactose (6P). For each experiment, at least 4 biological replicates were performed. (*p<0.001 p<0.01 *p<0.05.)
Figure 6A:
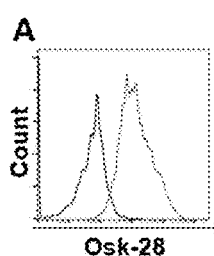
Figure 6B:
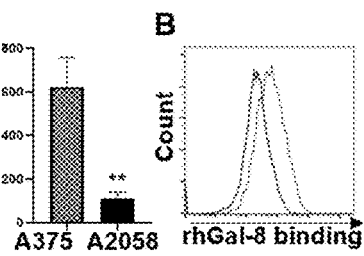
Figure 6C:
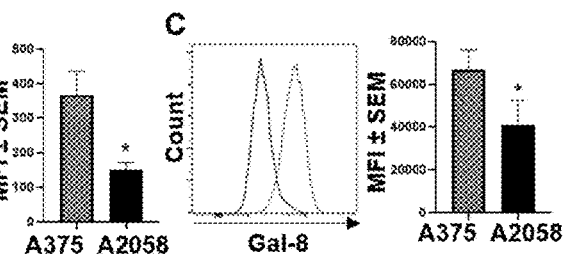
Figure 6K:
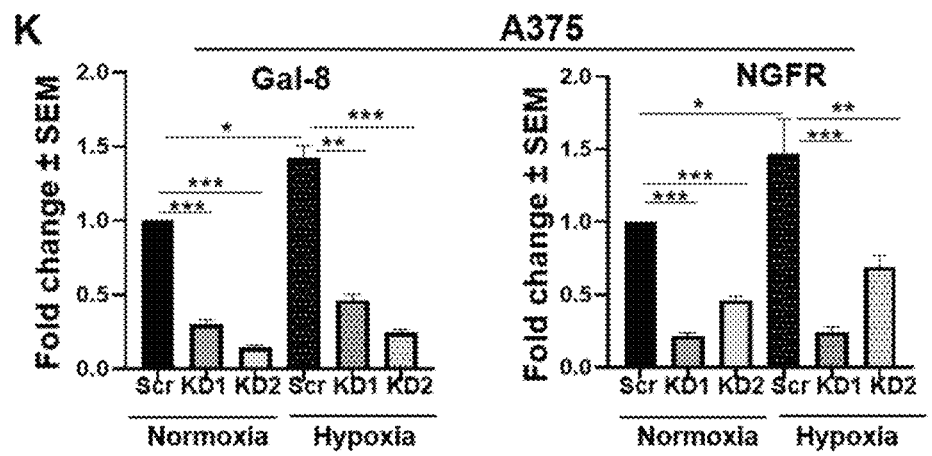
Figure 6L:
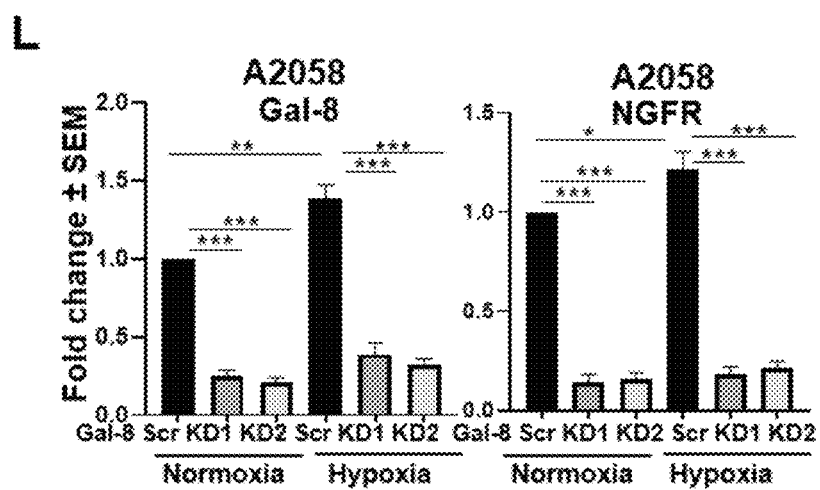
Figure 6M:
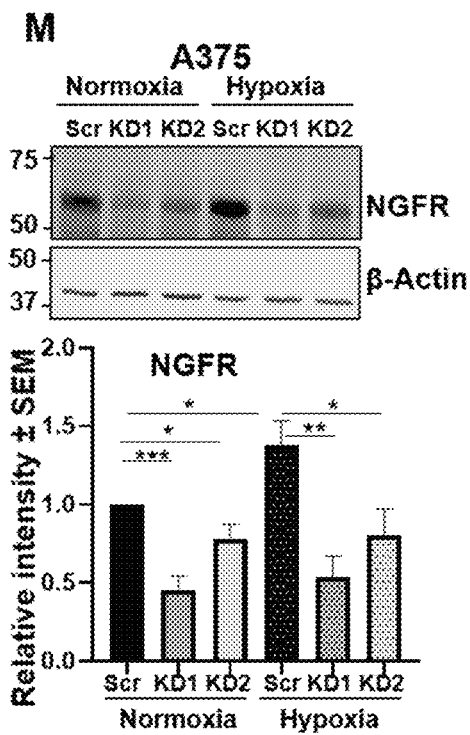
Figure 6N:
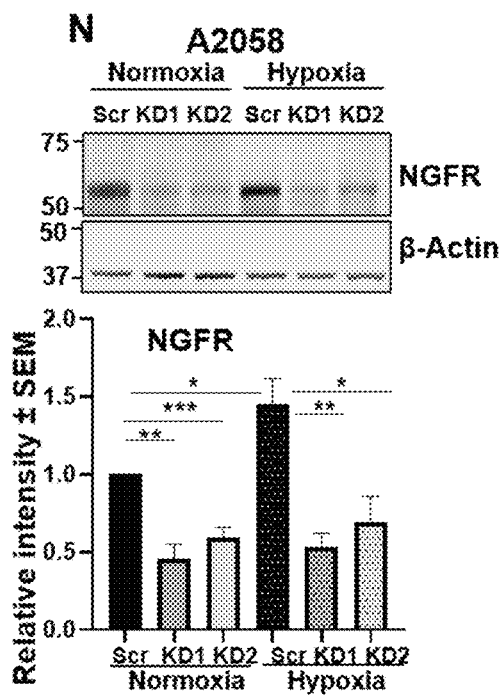

Example 3—Galectin (Gal)-8 Modulates NGFR Expression in MM Cells and is Elevated in MM Patient Serum With concomitant hypoxia-induced loss of GCNT2 and increase in Gal-8 expression, we assessed whether Gal-8 binding to i-linear poly-LacNAcs was favored over binding to I-branched poly-LacNAcs. Among MM A375 and A2058 cells, A375 expressed significantly more i-linear poly-LacNAcs compared with A2058 cells (p<0.01) (FIG. 6A) and binding of recombinant human Gal-8 (rhGal-8) to A375 cells was significantly higher than binding to A2058 cells (p<0.05) (FIG. 6B). Furthermore, intracellular staining of endogenous Gal-8 expression illustrated increased Gal-8 expression in A375 cells that had higher i-linear poly-LacNAc expression (p<0.05) (FIG. 6C).

To investigate whether i-linear poly-LacNAcs encouraged Gal-8 interactions, rhGal-8 was incubated with A375 GCNT2 OE and EV cells as well as A2058 GCNT2 KD and Scr cells. MM cells with low GCNT2 and high i-linear poly-LacNAcs bound Gal-8 to a greater degree compared with binding to cells with high GCNT2 expression (p<0.01 and p<0.05) (FIGS. 6D and 6E). To elucidate the clinical significance of Gal-8 in MM, patient serum samples (n=13) were analyzed for Gal-8 levels compared with nominal controls by ELISA. There was a significant increase in Gal-8 levels in patient sera (p<0.05) (FIG. 6F).

To explore the relationship of elevated Gal-8 levels and MM TIC generation, A375 and A2058 MM cell lines were incubated with rhGal-8, and NGFR expression was analyzed by immunoblotting. There was a significant elevation in NGFR in Gal-8-treated cells (FIGS. 6G and 6H).

Figure 6O:
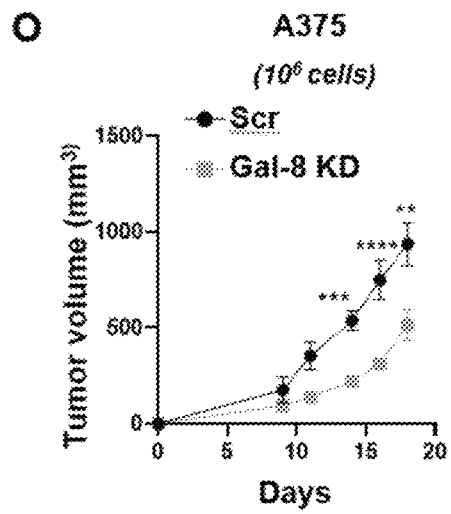
Figure 6P:
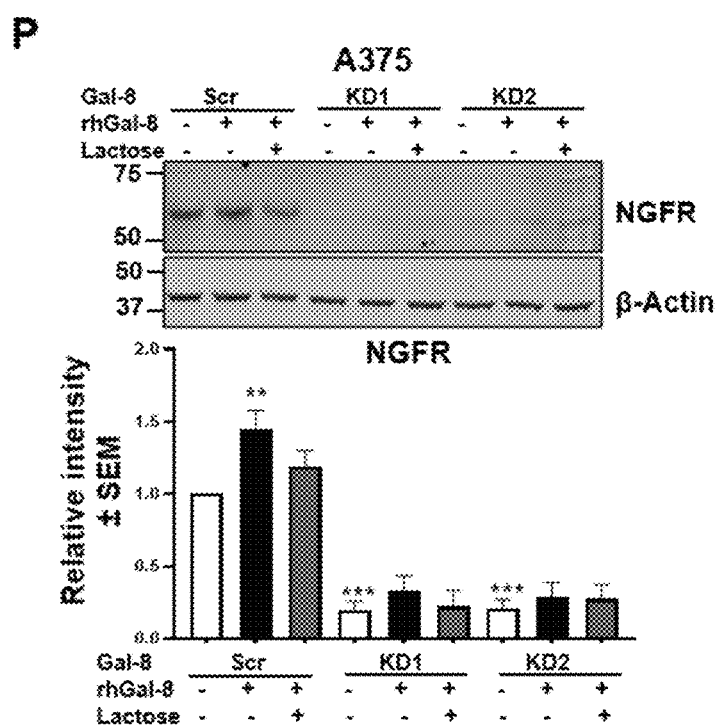

Furthermore, to determine whether intrinsic Gal-8 could alter NGFR expression, A375 and A2058 cells silenced for Gal-8 expression (KD) by shRNA technology were analyzed by RT-qPCR. Compared with shRNA control cells (Scr), silencing of Gal-8 in Gal-8 KD cells was confirmed by RT-qPCR (FIGS. 6I and 6J). A375 and A2058 Scr and Gal-8 KD cells were cultured under normoxia and hypoxia and then assessed for NGFR induction. Under hypoxia, while NGFR was elevated in Scr control cells as assayed by RT-qPCR (FIGS. 6I and 6J) and Western blotting (FIGS. 6K, 6L, 6M and 6N), Gal-8 KD cells were unable to upregulate NGFR. These data implicate both hypoxia-dependent and -independent roles of Gal-8 in NGFR regulation. In accordance with downregulation of NGFR by silencing Gal-8, Gal-8 KD cells formed tumors at a significantly less rate than Scr cells in vivo (FIG. 6O) (p<0.01). Further, while exogenous Gal-8 significantly upregulated NGFR in Scr cells, incubating Gal-8 with Gal-8 KD MM cells was not able to rescue NGFR expression (FIG. 6P), indicating a dual role of Gal-8 as an extracellular (outside-in) and intracellular modulator of NGFR expression. In pan-galectin inhibitor lactose controls, incomplete diminution is often observed in signaling assessments. Hence, while it is an appropriate control for short-term lectin binding assays, lactose may not be the most ideal galectin neutralizer in signaling analyses. Altogether, the data present a novel mechanistic role of Gal-8 in regulating MM TIC marker, NGFR.

Figures 7A, 7B:
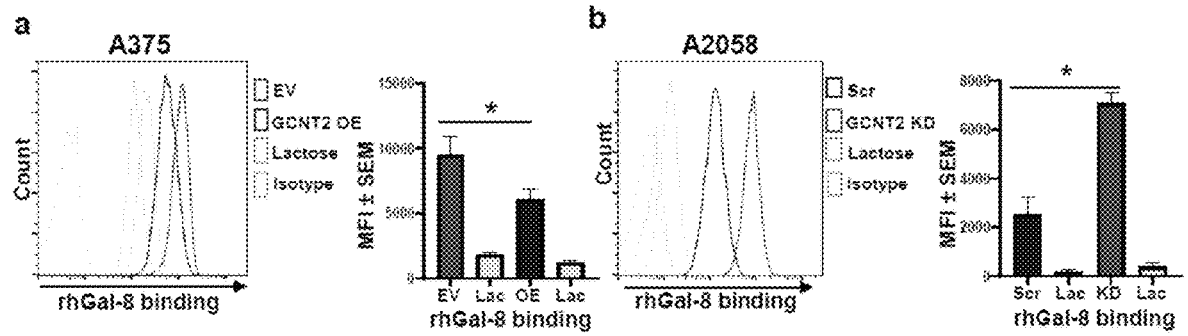

Example 4—Galectin (Gal)-8 Preferentially Bound i-Linear Poly-LacNAcs on MM Cells and the MM Cell Surface Receptor CD44, and Removal of CD44—N Glycans Ablated Gal-8 Binding To assess whether Gal-8 binding to i-linear poly-LacNAcs was favored over binding to I-branched poly-LacNAcs on MM cells, Gal-8 was incubated with A375 GCNT2 OE and EV cells as well as A2058 GCNT2 KD and Scr cells. MM cells with low GCNT2 and high i-linear poly-LacNAcs bound Gal-8 at a significantly greater degree than to cells with high GCNT2 expression and low i-linear poly-LacNAcs (p<0.05 and p<0.05) (FIGS. 7A and 7B). Lactose solution was incubated with Gal-8 as negative control for galectin binding.

To identify specific glycoprotein ligands of Gal-8 on MM cell surfaces, Gal-8 affinity chromatography followed by mass spectrometry of eluates was performed using both A375 and A2058 MM cell lines (Tables 3 and 4).

TABLE 3

Top 10 Gal-8 ligands eluted with rhGal-8 from human A375 MM cell lysates

| UniProt Accession | Description | Exp. q-value | Coverage [%] | # Peptides | # PSMs | # Unique Peptides | Score |
|---|---|---|---|---|---|---|---|
| Q6UVK1 | Chondroitin sulfate proteoglycan 4 OS = Homo sapiens OX = 9606 GN = CSPG4 PE = 1 SV = 2 | 0.00E+00 | 16 | 28 | 39 | 28 | 105.9 |
| Q6YHK3 | CD109 antigen OS = Homo sapiens OX = 9606 GN = CD109 PE = 1 SV = 2 | 0.00E+00 | 13 | 17 | 24 | 17 | 65.76 |
| P15144 | Aminopeptidase N OS = Homo sapiens OX = 9606 GN = ANPEP PE = 1 SV = 4 | 0.00E+00 | 19 | 17 | 23 | 17 | 61.81 |
| P05023 | Sodium/potassium-transporting ATPase subunit alpha-1 OS = Homo sapiens OX = 9606 GN = ATP1A1 PE = 1 SV = 1 | 0.00E+00 | 20 | 16 | 20 | 16 | 54.97 |
| Q8NFJ5 | Retinoic acid-induced protein 3 OS = Homo sapiens OX = 9606 GN = GPRC5A PE = 1 SV = 2 | 0.00E+00 | 11 | 5 | 12 | 5 | 43.7 |
| Q93050 | V-type proton ATPase 116 kDa subunit a1 OS = Homo sapiens OX = 9606 GN = ATP6V0A1 PE = 1 SV = 3 | 0.00E+00 | 14 | 9 | 15 | 9 | 42 |
| Q15365 | Poly(rC)-binding protein 1 OS = Homo sapiens OX = 9606 GN = PCBP1 PE = 1 SV = 2 | 0.00E+00 | 32 | 8 | 14 | 5 | 39.3 |
| P05556 | Integrin beta-1 OS = Homo sapiens OX = 9606 GN = ITGB1 PE = 1 SV = 2 | 0.00E+00 | 21 | 13 | 15 | 13 | 37.96 |
| P16070 | CD44 antigen OS = Homo sapiens OX = 9606 GN = CD44 PE = 1 SV = 3 | 0.00E+00 | 12 | 8 | 13 | 8 | 37.46 |
| Q15366 | Poly(rC)-binding protein 2 OS = Homo sapiens OX = 9606 GN = PCBP2 PE = 1 SV = 1 | 0.00E+00 | 21 | 6 | 12 | 3 | 32.11 |

TABLE 4

Top 10 Gal-8 ligands eluted with rhGal-8 from human A2058 MM cell lysates

| UniProt Accession | Description | Exp. q-value | Coverage [%] | # Peptides | # PSMs | # Unique Peptides | Score |
|---|---|---|---|---|---|---|---|
| P21741 | Midkine OS = Homo sapiens OX = 9606 GN = MDK PE = 1 SV = 1 | 0.00E+00 | 39 | 7 | 30 | 7 | 88.15 |
| P09429 | High mobility group protein B1 OS = Homo sapiens OX = 9606 GN = HMGB1 PE = 1 SV = 3 | 0.00E+00 | 34 | 7 | 15 | 5 | 45 |
| P37802 | Transgelin-2 OS = Homo sapiens OX = 9606 GN = TAGLN2 PE = 1 SV = 3 | 0.00E+00 | 27 | 5 | 13 | 5 | 30.49 |
| P02765 | Alpha-2-HS-glycoprotein OS = Homo sapiens OX = 9606 GN = AHSG PE = 1 SV = 2 | 0.00E+00 | 7 | 4 | 24 | 4 | 67.68 |
| Q99497 | Parkinson disease protein 7 OS = Homo sapiens OX = 9606 GN = PARK7 PE = 1 SV = 2 | 0.00E+00 | 29 | 4 | 18 | 4 | 49.41 |
| P16070 | CD44 antigen OS = Homo sapiens OX = 9606 GN = CD44 PE = 1 SV = 3 | 0.00E+00 | 7 | 4 | 9 | 4 | 24.4 |
| P09382 | Galectin-1 OS = Homo sapiens OX = 9606 GN = LGALS1 PE = 1 SV = 2 | 0.00E+00 | 27 | 3 | 17 | 3 | 49.01 |
| P51858 | Hepatoma-derived growth factor OS = Homo sapiens OX = 9606 GN = HDGF PE = 1 SV = 1 | 0.00E+00 | 12 | 3 | 11 | 3 | 27.31 |
| P27816 | Microtubule-associated protein 4 OS = Homo sapiens OX = 9606 GN = MAP4 PE = 1 SV = 3 | 8.00E−03 | 4 | 3 | 5 | 3 | 11.4 |
| Q9H910 | Jupiter microtubule associated homolog 2 OS = Homo sapiens OX = 9606 GN = JPT2 PE = 1 SV = 1 | 1.10E−02 | 22 | 3 | 4 | 3 | 9.91 |

Figures 7C, 7D:
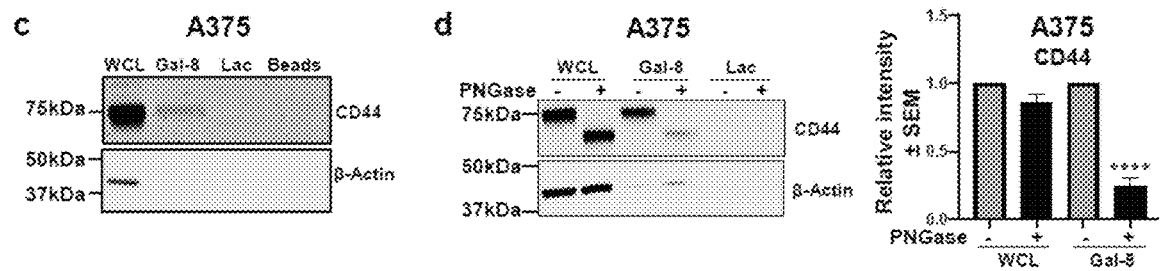
Figures 7E, 7F:
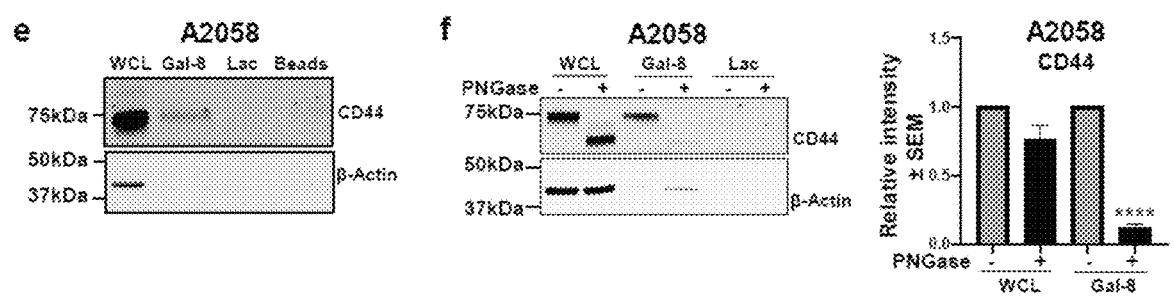

After eliminating proteins found in lactose control eluates, CD44 was the top membrane glycoprotein identified in both MM cell lines. CD44 is a metastasis-promoting factor that can potentiate disease progression in multiple tumors, including MM. CD44 was subsequently confirmed as a Gal-8 ligand in Gal-8 eluates from A375 and A2058 cell lines (FIGS. 7C and 7E). Furthermore, treatment with PNGase, which cleaves N-glycans, ablated the capacity of Gal-8 to bind CD44 (FIGS. 7D and 7F) ($p<0.0001$), implicating N-glycan-dependency in Gal-8—CD44 binding interactions.

To determine whether Gal-8—Gal-8 ligand interactions were affected by I-branched poly-LacNAc expression, A375 GCNT2 OE and A2058 GCNT2 KD cells and their respective controls were used for Gal-8 affinity chromatography. Gal-8 binding to CD44 was significantly greater on cells with low GCNT2 levels and high i-linear poly-LacNAcs than on cells with high GCNT2 levels and high I-branched poly-LacNAcs ($p<0.01$) (FIGS. 7G and 7H).

To assess whether Gal-8—Gal-8 ligand interactions triggered canonical intracellular signaling, activation of pro-survival molecule, AKT, was analyzed in MM cells with mainly i-linear poly-LacNAc expression (GCNT2 KD). AKT is a downstream effector of CD44 engagement. Gal-8 incubation with A2058 GCNT2 KD cells expressing i-linear poly-LacNAcs increased AKT activation compared with Scr control cells (FIG. 7I) ($p<0.05$). GCNT2 KD cells even had a higher basal level of AKT activation. These data indicate that Gal-8 modulated MM cell signaling, in part, via cell surface expression of i-linear poly-LacNAcs on the principal identified Gal-8 ligand, CD44.

Cell surface Gal-8 ligands include α3, α5, and β1 integrins, IL-2Rβ, TGFβ type I receptor, podoplanin, CD166, and CD44. In MM and other cancers, CD44 can potentiate metastasis. CD44 tumor-promoting activity can be transmitted from several key ligands, including hyaluronic acid (HA), E- and L-selectin (a CD44 glycoform known as "HCELL"), Gal-9, osteopontin, matrix metalloproteases, and now Gal-8 on MM cells. CD44 N- and O-glycans and their terminal sialylation play critical roles in promoting or preventing HA-binding or HCELL activity on hematopoietic cells and human colorectal cancer cells. The putative role of MM cell CD44 N-glycan—Gal-8 interactions via i-linear poly-LacNAcs posits another CD44 glycoform that can convey pro-tumorigenic activity, further broadening the importance of post-translational modifications on CD44 in cancer.

CD44 has multiple isoforms (>800) due to alternative exon splicing and related variable amounts of N-glycan, O-glycan and/or heparan sulfate structures. These glycoforms contain critical binding sites for ligand binding, hyaluronic acid (HA), E-selectin, among other lectins (i.e., galectins) and other heterotypic factors. CD44 is alternatively spliced from 10 variant (v) exons that encode extracellular domains in the stalk region proximal the extracellular head region found on all isoforms. The standard CD44 isoform (CD44s), which contains the head region and no variable regions, contains (5) potential N-glycan sites, resolves at 75-95 kDa, and is found on several cell types, including fibroblasts and hematopoietic cells. Some of the more common variant isoforms are CD44v3, CD44v6, CD44v10, CD44v3-10, CD44v6-10, CD44E (v8-10) and are found on endothelial cells, epithelial cells, activated lymphocytes, and tumor cells. Western blot data of Gal-8 affinity chromatography eluates show a ~75 kDa band from human MM cell extracts using a ubiquitous anti-CD44 moAb (Cell Signaling), so there is, at minimum, the CD44s isoform displaying N-glycans for Gal-8-binding.

To reveal CD44 isoforms, FACS stain human and mouse melanoma cell lines are performed using commercially-available moAbs to specific CD44v isoforms (Bio-Rad). Negative control blots are conducted using Gal-8 eluates obtained in presence of Gal-8 inhibitory 50 mM lactose and using 800CW or 680RD-2° Ab alone. To analyze dependency of linear or I-branched poly-LacNAcs on identified CD44 isoform for Gal-8-binding, we will similarly conduct Gal-8-purify CD44 from our validated empty vector control or GCNT2 OE human A375 MM and Scr or GCNT2 KD human A2058 MM models and blot with specific anti-CD44 variant Ab. These experiments are done >3-times and blots will be scanned using Li-Cor Odyssey imaging.

To ascertain whether other pro-metastatic N-glycan-dependent CD44 receptor/ligands, endothelial (E)-selectin, and HA, compete for or cooperate with Gal-8-binding, individual and combined incubations of parental human/mouse MM cell lines with rhGal-8 (R&D Systems), FITC-HA (Matexcel) and/or rhE-sel-Ig (R&D systems) are conducted. FACS analysis with Abs to Gal-8, FITC, and Ig is used to assess inhibited, enhanced, or unchanged Gal-8 binding. Controls are to elute any pre-bound Gal-8 by pre-treating cells with 50 mM lactose to avoid interference prior to FITC-HA or rhE-sel-Ig incubations. These data reveal whether Gal-8 partners with other MM-associated CD44 receptor/ligands.

To determine whether identified Gal-8 ligand CD44 is a major cell surface Gal-8 ligand and directly correlates with expression of MM TIC factor NGFR and the capacity to fat In tumors in vivo, human A375 and A2058 MM cells and mouse YUMM1.1 cells silenced for CD44 expression are generated. Lentiviral particles with scrambled (Scr) or interfering shRNA against CD44 (KD) (GeneCopoeia) are used. Cells are transduced and selected in 1 mg/ml Hygromycin (Corning), and CD44 levels in Scr and CD44 KD cells are validated by RT-qPCR and Western blotting.

To assess the contribution of CD44 as a Gal-8 ligand, rhGal-8 binding to Scr and CD44 KD variants is analyzed by FACS, including 50 mM lactose incubations to control for Gal-8 binding. To assess CD44's role in Gal-8-dependent NGFR expression, Scr and CD44 KD A375 and A2058 cells are incubated with rhGal-8 (20 μg/ml; R&D systems) for 16 hr, and NGFR (Ab from Abcam) is analyzed by Western blotting. Control blots include loading controls for β-actin (Abcam). Scr and CD44 KD A375 and A2058 cells incubated with Gal-8 (20 μg/ml) for 15 min and 30 min in serum free media are then assessed. Cell lysates are blotted for phospho-AKT (pS473) and control total AKT (Cell Signaling). This data help correlate with CD44 dependency for Gal-8-induced NGFR and pro-survival factor pAKT.

To assess the impact of Gal-8 on melanoma cell Gal-8 ligand CD44, cellular and mouse tools are used in in vivo TIC capacity/limiting dilution assays. WT or lgals8 (Gal-8) KO mice (bred in house) are inoculated with syngeneic Scr or CD44 KD YUMM1.1 variant melanoma cells from $1\times10^3$ to $1\times10^5$ into the flank. Tumor volumes are calculated using the formula: [tumor volume $(mm^3)$=(length×(width)$^2$×0.5] every 3 days. All experiments are done >3-times to meet statistical significance.

The N-glycans on MM cell CD44 are the key glycan constituents binding Gal-8. To interrogate the poly-LacNAcs on CD44 N-glycan antennae and ascertain using CD44 immunoprecipitated (IP) from high Gal-8-binding (EV) or low Gal-8-binding (GCNT2 OE) A375 MM cells and from low Gal-8-binding (Scr) or high Gal-8-binding (GCNT2 KD) A2058 MM cells, whether GCNT2 directly adds I-branches to CD44 subunit is determined. Using human A375/UACC62 and mouse D4M melanoma cells, including GCNT2 OE and GCNT2 KD cell variants, MALDI-TOF-TOF MS/MS N-glycomic analysis is conducted on anti-CD44 IP for poly-LacNAc analysis. Precise structure assignments can then be attained by GC-MS linkage analysis and exoglycosidase digestions. In addition, selected glycan molecular ion species can be subjected to MS/MS to produce sequence informative fragment ions.

The clinical significance of the loss of GCNT2 with melanoma patient prognosis was analyzed. The results show that reduced levels of GCNT2 in MM corresponded with significantly reduced survival. Hence, the expression level of GCNT2 could serve as a prognostic biomarker for disease progression. Other key data from our analysis of GCNT2 impact on MM cell function revealed that reductions in GCNT2/I-branching expression evokes TIC generation, whereas high levels of GCNT2 abolishes classic MM TIC phenotypes, such as NGFR/CD271 marker expression, and the capability to form tumors in in vivo limiting dilution assays. The data here suggest that elevations in i-linear poly-LacNAcs are promoted by hypoxia, lead to increases in TIC characteristics, and in part, correlate with higher disease relapse and patient mortality rates.

MM is one of the most hypoxic tumors having an intratumoral oxygen tension of only 1%. Our study here addressed the role of hypoxia in MM glycosylation signature and pathway derangement. Data illustrated here depict global glycome-gene alterations in MM cells under hypoxia. Among the numerous dysregulated glycome-related genes, Gal-8 was found to be a major hypoxia-induced MM factor. Furthermore, GCNT2 was reduced under hypoxia, along with a corresponding gain in i-linear poly-LacNAc expression and TIC marker expression. The observation of increased i-linear poly-LacNAcs using specialized MS/MS glyco-analytics provides strong structural evidence that hypoxia helps promote i-linear poly-LacNAc expression on MM cells. Altogether, these results portray a concerted action of hypoxia on the MM glycome, and, in part, Gal-8 expression in fostering MM TIC characteristics.

Gal-8 has never been linked to MM progression. In the present invention, under hypoxia, Gal-8 was the most upregulated galectin. Gal-8 binding to i-linear poly-LacNAcs was greater than binding to I-branched poly-LacNAcs. Given the profound loss of GCNT2 in MM patient samples, Gal-8 may bind these MM cells preferentially and alter cellular signaling. Exogenous rhGal-8 treatment of MM cells resulted in increased MM TIC marker, NGFR, expression. However, the unexpected observation that loss of MM cell Gal-8 prevented the upregulation of NGFR even under hypoxia, a known driver of NGFR expression, strongly indicates dependence of NGFR induction by both exogenous and melanoma cell-intrinsic Gal-8. Since NGFR has been associated with melanoma progression as well as therapy resistance, neutralization of Gal-8 represents a novel therapeutic approach to prevent disease progression.

Figure 8:
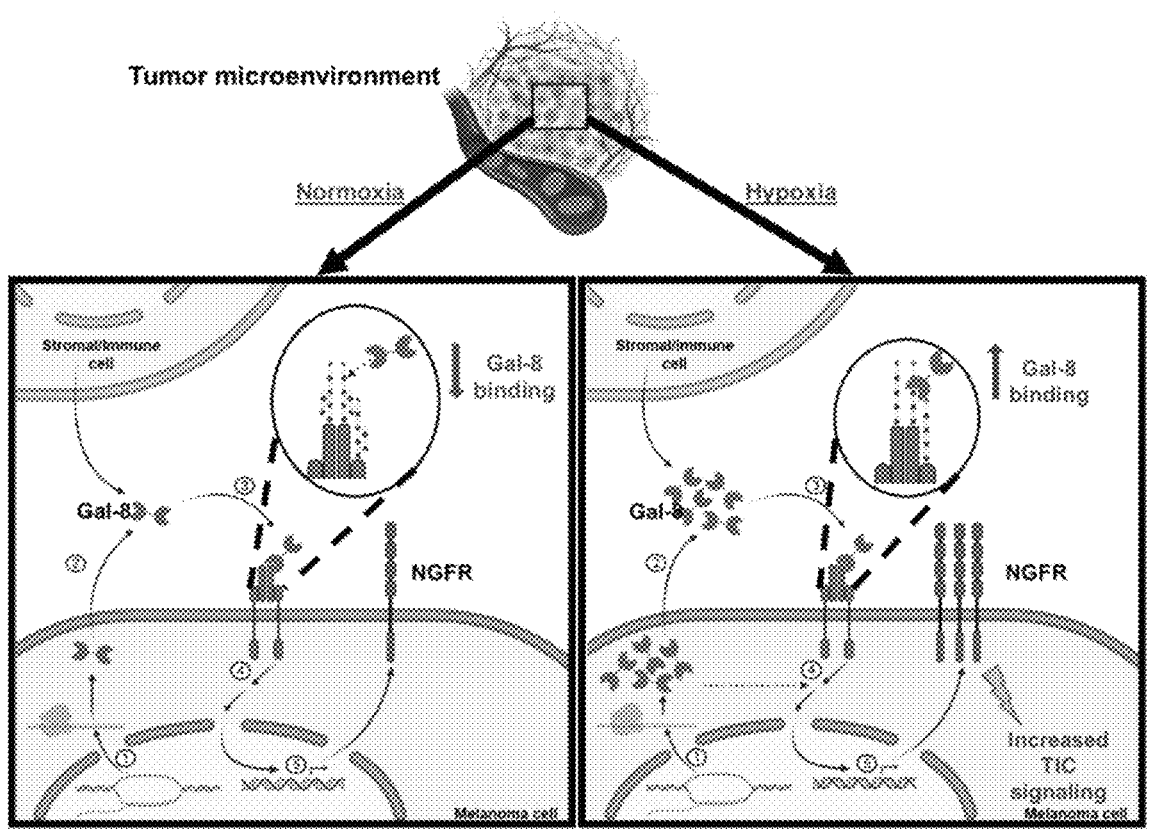
FIG. 8. Upregulated Gal-8 levels under hypoxic conditions are coupled with up-regulation of the pro-melanoma TIC marker NGFR. Gal-8 gene expression is upregulated within the melanoma cell (1) and consequently secreted into the tumor microenvironment under hypoxia (2). Extracellular Gal-8, either produced by melanoma cells or stromal/immune cells, bind preferentially to cell surface glycoproteins decorated with the predominant i-linear poly-LacNAcs under hypoxia (3). Enhanced Gal-8 binding potentially modulates related downstream signaling pathways (4), promoting expression of the MM TIC marker, NGFR (5). NGFR: nerve growth factor receptor, TIC: tumor-initiating cells.

Of particular clinical importance, significant elevations in Gal-8 from MM patient sera were noted compared with controls, suggesting that Gal-8 may be a biomarker of active melanoma. Therefore, in addition to the loss of GCNT2/I-branching in MM cells, increases in Gal-8 serum levels may also represent a direct correlate with melanoma progression. As presented in the studies herein, the mechanistic data of hypoxia-dependent enforcement of the MM signature glycome and the Gal-8-dependent upregulation of pro-MM TIC marker NGFR represent novel pathways in MM that can be exploited for therapeutic exploitation (Illustrated in the cartoon model; FIG. 8).

Example 5—the Growth- and Metastasis-Promoting Roles of Gal-8 in Melanoma

Gal-8 can drive expression of TIC factor, NGFR, and related MM TIC activity in vivo. Moreover, Gal-8 is elevated in melanoma patients compared with normal healthy volunteers and, when Gal-8 is silenced in human A375 MM cells, they form a xenograft at a significantly less rate. These data support subsequent in vivo studies examining the role of Gal-8 promoting growth and metastatic activity of melanoma cells.

Elucidating Gal-8's role provides rationale for therapeutic exploitation to complement the promise of ICI therapies and support strategic therapeutic targeting of the MM glycome. Gal-8 silenced (KD) human and murine melanoma cell lines also transduced with luciferase to allow tracking of metastases formation in distant tissue sites have been developed and validated. Plus, Gal-8 KO (B6) mice were obtained to use in syngeneic tumor growth/metastasis assessments and therapeutic anti-PD1 Ab is used in the syngeneic model to assess Gal-8's role in averting immune boosting, anti-tumor activity.

To study the MM cell-intrinsic role of Gal-8 in human MM xenograft formation and metastases formation, 6 to 8-week-old NSG mice are used as hosts for luciferase+Scr control and Gal-8 KD human MM (A375/A2058/SKMEL5) tumor growth and metastasis studies. Cell inocula are injected s.c. into flanks at $1\times10^6$ viable cells/inoculum for growth studies and i.v. at $1\times10^6$ viable cells/inoculum for experimental metastasis assays. Tumor growth rates and metastasis formation rates (likely in the lung) are monitored via bioluminescence measurements longitudinally. At necropsy (killed with >10% weight loss or s.c. tumor <2 cm³), Gal-8 WT and KD tumors are also be assessed for vascularity using IHC of CD31 (in house), which may be affected by Gal-8 loss. CD31+ vessel cells are counted by microscopy from >6 fields and analyzed for statistical significance. Tumor burden or the relative optical signal intensity from tumor tissue site is plotted over time. Kaplan-Meier curves assessing Survival and Time to Death are conducted.

To identify whether Gal-8 expression corresponds with TIC marker NGFR expression and human melanoma growth in vivo, FFPE-tumors (n=8) are prepared and stained with fluorescent-labelled antibodies against Gal-8 and NGFR (in-house). Sections are counterstained with DAPI and scored and assessed for single and dual-stained cells, which reflect TIC capacity. In all, results reveal the MM cell-intrinsic role of Gal-8 in tumor TIC capacity, growth, and metastasis and reveal whether Gal-8 augments melanoma growth and metastasis coincident with TIC capacity and vessel formation.

Example 6—Analyze Role of Gal-8 and its Linear Poly-LacNAc Ligands on Melanoma Growth and Metastasis Using Murine Gal-8+/− or GCNT2+/− Melanoma Models and Gal-8 WT/KO Mice To help distinguish the role of host vs. MM cell-intrinsic Gal-8 on melanoma growth and metastasis, a syngeneic mouse model is used. WT(B6) and Gal-8 KO (B6) mice are used as hosts for inocula of murine luciferase+Scr or Gal-8 KD melanoma YUMM1.1 cells. To examine the role of linear (Gal-8 high binding) vs. I-branched (Gal-8 low binding) poly-LacNAc in Gal-8— ligand axis, luciferase+EV/Scr control or GCNT2 OE/KD YUMM1.1 cell variants are inoculate. Since immunity and angiogenesis are also associated with Gal-8, these experiments critically address how Gal-8 may be lowering tumor growth and metastasis. Cell inocula are injected s.c. into flanks at $10^6$ viable cells/inoculum for growth studies and i.v. at $10^6$ viable cells/inoculum for experimental metastasis assays (n=3). Tumor growth and metastases rates are assayed by bioluminescence. Tumor burden or relative optical signal intensity from tumor tissue site is plotted over time. Kaplan-Meier curves of Survival and Time to Death are generated.

At necropsy, vector control, Gal-8 KD, and GCNT2 OE/KD tumors (n=>6/genotype) grown in Gal-8 WT/KO mice are assessed for vascularity using IHC of CD31 (in-house), which may be affected by Gal-8 loss. CD31+ vessels cells are counted by microscopy from >6 fields and analyzed for statistical significance.

To assess whether Gal-8 expression fosters melanoma immune evasion, vector control, Gal-8 KD, and GCNT2 OE/KD tumors (n=6/group) grown in Gal-8 WT/KO mice (n=>6/genotype) are collected and tumor-infiltrating lymphocytes (TIL) are analyzed by FACS. After tumor mincing and straining (20 µm) on ice, cells are FACS analyzed with anti-CD45, CD3, CD4, and CD8 Abs. Anti-tumor or immunosuppressive TIL phenotype is further sorted by using antibodies to immune boosting factors, IFN-γ, IL-12, IL-17 and TNF-α, and to immunoregulators, PD1, TGF-β, IL-10, indolamine 2,3 oxidase (IDO), IL-2RA and FoxP3. Overall, these assays address whether Gal-8-dependent modulation of CD4+ or CD8+ effector or exhausted/regulatory T cell subsets. These TIL assays will decipher whether Gal-8 and Gal-8-binding linear poly-LacNAc expression provide superior immune evading properties.

Example 7—Analyze In Vivo Efficacy of Anti-PD1 Ab Using Murine Gal-8+/−MM Models in Gal-8 WT/KO Mice Because ICI therapy is one of the most promising approaches to treat MM, efforts are abound to devise complementary methods or biomarker predictors of outcome to be able to synergize ICI therapeutic response and avoid clinical obstacles. To this end, syngeneic MM models are utilized to assay in vivo efficacy of therapeutic anti-PD1 Ab efficacy in the presence or absence of host or MM cell-intrinsic Gal-8. luciferase+ murine control, Gal-8 WT/KD, and GCNT2 OE/KD YUMM1.1 (B6) are implanted into the s.c. flanks of Gal-8 WT/KO (B6) mice and primary and metastatic tumor growth are assayed via bioluminescent optical imaging. Following implantation into s.c. flank, mice are treated with therapeutic InVivoMAb anti-mouse PD-1 (CD279) (Bxcell) (200 µg/mouse; IP every other day for 4-6 weeks until necropsy (2 cm$^3$). At necropsy, tumors (n=6/group) are FACS analyzed for immune cell infiltration, particularly, the ratio of CD4+ or CD8+ T cells: FOXP3+ Treg cells. These data reveal whether host and MM cell intrinsic Gal-8 can impact the anti-melanoma efficacy of anti-PD1 therapy. Importantly, these results highlight whether Gal-8 expression and/or Gal-8-binding glycans synthesized by GCNT2 can boost or compromise anti-tumor activity conferred by anti-PD1 therapy.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

---

What is claimed is:

1. A method for treating an immune checkpoint inhibitor (ICI) therapy-resistant melanoma in a subject, comprising administering to the subject an inhibitor of Gal-8 expression and/or function.

2. The method of claim 1, the administration being local, intratumoural, or intravenous administration.

3. The method of claim 1, the subject being a human.

4. The method of claim 1, the melanoma being stage II, III or IV melanoma.

5. The method of claim 1, the inhibitor being an anti-Gal-8 antibody or Gal-8 binding antagonist.

6. The method of claim 1, the inhibitor being a construct comprising a sequence encoding a siRNA or shRNA targeting Gal-8.

7. The method of claim 6, the shRNA targeting Gal-8 being encoded by the sequence comprising SEQ ID NO: 5 or 6.

8. The method of claim 1, the ICI therapy-resistant melanoma being metastatic melanoma.

9. A method for slowing the growth of melanoma cells, the method comprising contacting the melanoma cells with an inhibitor of Gal-8 expression and/or function, the melanoma cells being resistant to one or more ICIs.

10. The method of claim 9, the melanoma cells having reduced expression level of GCNT2 prior to contacting the inhibitor of Gal-8.

11. The method of claim 9, the inhibitor being an anti-Gal-8 antibody or Gal-8 binding antagonist.

12. The method of claim 9, the inhibitor being a construct comprising a sequence encoding a siRNA or shRNA targeting Gal-8.

13. The method of claim 12, the shRNA targeting Gal-8 being encoded by the sequence comprising SEQ ID NO: 5 or 6.

14. The method of claim 9, the melanoma cells being metastatic melanoma cells.

15. The method of claim 9, the melanoma cells being under hypoxia.

16. A method for improving survival of a metastatic melanoma patient, the method comprising administering to the metastatic melanoma patient an inhibitor of Gal-8 expression and/or function, the metastatic melanoma patient being resistant to an ICI therapy.

17. The method of claim 16, the inhibitor being an anti-Gal-8 antibody, Gal-8 binding antagonist, or a construct comprising a sequence encoding siRNA targeting Gal-8 or shRNA targeting Gal-8.

18. The method of claim 16, the shRNA targeting Gal-8 being encoded by the sequence comprising SEQ ID NO: 5 or 6.

* * * * *

SEQUENCE LISTING

```
Sequence total quantity: 9
SEQ ID NO: 1            moltype = DNA  length = 40
FEATURE                 Location/Qualifiers
source                  1..40
                        mol_type = genomic DNA
                        organism = Homo sapiens
SEQUENCE: 1
cgacagatct gccaccatga acttttggag gtactgcttt                          40

SEQ ID NO: 2            moltype = DNA  length = 33
FEATURE                 Location/Qualifiers
source                  1..33
                        mol_type = genomic DNA
                        organism = Homo sapiens
SEQUENCE: 2
tgtcaagctt tcaaaaatac cagctgggtt gta                                 33

SEQ ID NO: 3            moltype = DNA  length = 21
FEATURE                 Location/Qualifiers
source                  1..21
                        mol_type = genomic DNA
                        organism = Homo sapiens
SEQUENCE: 3
gctaacaagt ttgagcttaa t                                              21

SEQ ID NO: 4            moltype = DNA  length = 21
FEATURE                 Location/Qualifiers
source                  1..21
                        mol_type = genomic DNA
                        organism = Homo sapiens
SEQUENCE: 4
gctcacctct atattagttt a                                              21

SEQ ID NO: 5            moltype = DNA  length = 21
FEATURE                 Location/Qualifiers
source                  1..21
                        mol_type = genomic DNA
                        organism = Homo sapiens
SEQUENCE: 5
cctacagaat atcatctata a                                              21

SEQ ID NO: 6            moltype = DNA  length = 21
FEATURE                 Location/Qualifiers
source                  1..21
                        mol_type = genomic DNA
                        organism = Homo sapiens
```

```
SEQUENCE: 6
gctcggactt acaaagtacc c                                             21

SEQ ID NO: 7            moltype = DNA   length = 19
FEATURE                 Location/Qualifiers
source                  1..19
                        mol_type = genomic DNA
                        organism = Homo sapiens
SEQUENCE: 7
gcttcgcgcc gtagtctta                                                19

SEQ ID NO: 8            moltype = DNA   length = 4540
FEATURE                 Location/Qualifiers
source                  1..4540
                        mol_type = genomic DNA
                        organism = Homo sapiens
SEQUENCE: 8
aaactgcgtt taccttaaac aggcttactg tgttcactgc tggacgcctc tgggcaatct   60
taccctcctg ggaactgaga gagacaatgc taggagccag aaacatgagg aatacatgag   120
ctcggcgcca atggaacatg ctttcacacc gggtgcagct aaccaccaca tcatacaaaa   180
ctcgtcgctg acgttttaga tgtataatct gattggcatg gactcacaga ggagggagta   240
agggaagagt aagaagattt caaaggagag acacaggttg caggttagca gggaacagg    300
caagccaaat gcaaggagc cacttcagaa atgtgtcaca gaaaagtgaa aatgcaacct    360
agtggtaagt gaagagggga agaagaaaga aaaaggacca gaaccgtgaa ctgaagggac   420
agggaacagc cagacgagag cttcagccat cacgaggatg atttcggaac ctggagaaaa   480
tgtaagttaa atatatctac actctgatcc tatctcaaga gagagatatt ttactcattt   540
cctggttgtg aatgatgggc tcttggaagc actgtctttt tagcgcgtct cttatctctg   600
ccctgatttt tgtatttgtt tacaatactg agttatggga gaataaacgt tttctgaggg   660
cagctctgtc caatgcttca ctgttagcag aagcctgtca tcagattttt gaggggaaag   720
ttttttaccc aacagaaaat gcattgaaaa ctaccctttg tgaagctacc tgctatgagt   780
acatggttcg aagccactat gtaacagaaa cactctctga agaagaggct gggttccctt    840
tagcttacac agtgaccatc cacaaagact tcggcacttt tgagaggctc ttcagggcga   900
tttatatgcc ccaaaatgtc tactgtgtgc acctggatca gaaggcgacg gatgccttta   960
aaggtgcagt gaaacagtta ctcagctgct cccaaatgc ttttctggct tccaagaagg   1020
agtcggttgt ctatgggggg atctccaggc tccaggctga cctgaactgc tggaagacc    1080
ttgtggcctc tgaagttccc tggaagtatg tcatcaacac ctgcgggcaa gactttcccc   1140
tgaaaaccaa cagggaaata gttcagtatc tgaagggatt taagggaaa aatatcaccc    1200
ccggagtgct gcctcctgac cacgctgttg gacggactaa atacgtccac caagaactgt   1260
taaaccacaa aaattcctac gtgattaaaa caacaaatt aaaaactcct cctcctcatg    1320
acatggtgat ttacttttggc acggcctacg tggctctcac aagggacttt gctaacttcg   1380
tcctccaaga ccagctcgca cttgacttac tctcctggtc caaggacacc tacagccccg    1440
acgaacattt ctgggtgaca ctcaacagga ttcccggtgt tcctggctct atgccaaatg   1500
catcctggac tggaaacctc agagctataa agtggagtga catggaagac agacacggag   1560
gctgccacgg ccactatgta catggtattt gtatctatgg aaacggagac ttaaagtggc   1620
tggttaattc accaagcctg tttgctaaca agtttgagct taataccta cccccttactg    1680
tggaatgcct agaactgagg catcgcgaaa gaaccctcaa tcagagtgaa actgcgatac   1740
aacccagctg gtattttga gctattcatg agctactcat gactgaaggg aaactgcagc   1800
tgggaagagg agcctgtttt tgtgagagac ttttgccttc gtaatgttaa ccgtttcagg   1860
accacgttta tagcttcagg acctggctac gtaattatac ttaaaatatc cactggacac   1920
tgtgaaatac actaacagga tggctgggta gagcaatctg ggcactttgg ccaatttag    1980
tcttgctgtt tcttgatgct cacctctata ttagtttatt gttaggatca atgataaatt    2040
taaatgacct cagatctttg caccagatac tcatcatata caaatgtttt agtaaaaaag   2100
agaattgtag ataatactgt ctaggaaaat aagaattagg tttctttgaa gaaggaatct   2160
tttataaac cttaacagtc accactgtgc tcaaccagac agatagtgaa acagcttct    2220
gggtaattca ccaatttcct ttaaaacata agctacctga atggagaata catcttgttt   2280
ctgagtttca acactagcat ttttggctta ctcatggaca aagttctgta tatagtataa   2340
agtcattaac aagaaacagg atatgcttta agacagaatt cactgtctgt tgcttcagta   2400
aaaggacctc ggggaataaa acatttctct cttatatgcc agaatgtagg ctggtccta    2460
tgtcatgtct tccattaaga acactaaaaa gtccttgcaa gaatggagat atgcattcaa   2520
gagaggtgct atcacataga tctagtctga agtctcctga ctttcctct tctatgaccc   2580
ctctctcccc agtattatct tacttgcaaa atggagacca aattctatcc tgtgaggctt   2640
ttaattgcac catagtatgc tctgagtagc tttacactgc ctggtactga tagtagtgc    2700
tcgatttta agagccttca attgtagatg aacatctctg ttatttatcc ctcattcatc    2760
catccgttca ttcattcagc cttcaatcaa catctcttca tgtactgact tgtacaggac   2820
atgtactgag acaaaaagga aacataagag ctttttcact ctaaaaatct tggcaataat   2880
gtcaacacca gaaagcctcc tctggagaat cttacagagt gattgtagtt taatcagga    2940
acacacaggg ctgtgtagca tgataccagg cccaggagat cagtaattac aaattaaggg   3000
ttaaatcaga gattattcaa cagagggga gaaaggagga gacagaggga ggacctgttg   3060
tgttccagcc attctggtat tcctttatgt atctaatttc attcaaacct cacaacagtc   3120
ttgtgaggcc cttatataat tactcccatt ttgcagatga agtaactgag cttagaaag    3180
gttaatagca ccggggaaca atttctctgg gtgagaattg ggactctgtt gctggtcttc   3240
tcagttcatt tcctgaggtg gatttactga gagaggtga aataaagcca tatttagtat   3300
accagagaag gtagattta agaatggtct cagtgttaat actgagaaaa agtcctgtca   3360
gttcagaaaa gtagaagt ctactttagt ttcctgtaa tactaaaccg ttgagtttca    3420
aaatatttat ttattctaac aaaaagcaat tactacaaat ggatgacaca tttaatgaac   3480
acaattttat ttttttttctg taactgtgct tgttgaatgt caatcatatt taagggaat    3540
gactttgaag taaaaccttt tttcttgcta ctgaaaaaaa tggagttgtt ttgggtggta    3600
aagtgttaag gaatagggac agctggtcac acaaggaact cttgaaggcc acatgtgaaa   3660
acctgtcact tgcacagagg ccagtcccac taaggtgacc agagtgggct ccaagcacaa   3720
```

```
actgccattg gctatagatg ggactgtgtc cccccaaaat tcatgtgttg gagccttaac  3780
cctcaatgtg atggtatttg agatggggcc tttggtaagg gaagtttaga tgaggtcacg  3840
agggtaggac cctcatgatg ggatgagtcc ccttacaaga cctctggctt gggccgggcg  3900
tggtggctca cacctgtaat cccaacactt tgggaggcca aggcaggtag atcacttgat  3960
gccaggagtt ccagaccagg ctggccgaca tggtgaaacc ccatctctac taaaaaatat  4020
aaaaattagc cgggctttgt ggcatgtgcc tgtaatccca gctatttggc aggctgaggc  4080
atgagaatcg cttgaaccca ggaggtggag gttacagtga gctgagagtg ccccactgca  4140
ctccagcctg ggtgacagag cgagactttg tcccaaaaca aaataggtga ggggatagcg  4200
aatgcactca gggtcagcag tggagtttaa aaattgtctc ttttcaactt atttaaatga  4260
cagcacctga gaagaggaac cgttttacac tggatgtttc tcatgtagaa caagaaatct  4320
ttctggaatt gatgtttaca tgtctgttgt tggtcatctc tcctgtgtct taaatacttt  4380
aatgttggaa gagcatagtg tttgggctag tgggtttctg acagcccatg gaatgccct  4440
gaaactactg tatctgatgt ttgttttcga tgaggttcca tgttttgttt tcttgggaat  4500
aaattaatat attgttttcc aaaaaaaaaa aaaaaaaaaa                        4540

SEQ ID NO: 9         moltype = AA  length = 402
FEATURE              Location/Qualifiers
source               1..402
                     mol_type = protein
                     organism = Homo sapiens
SEQUENCE: 9
MMGSWKHCLF SASLISALIF VFVYNTELWE NKRFLRAALS NASLLAEACH QIFEGKVFYP   60
TENALKTTLD EATCYEYMVR SHYVTETLSE EEAGFPLAYT VTIHKDFGTF ERLFRAIYMP  120
QNVYCVHLDQ KATDAFKGAV KQLLSCFPNA FLASKKESVV YGGISRLQAD LNCLEDLVAS  180
EVPWKYVINT CGQDFPLKTN REIVQYLKGF KGKNITPGVL PPDHAVGRTK YVHQELLNHK  240
NSYVIKTTKL KTPPPHDMVI YFGTAYVALT RDFANFVLQD QLALDLLSWS KDTYSPDEHF  300
WVTLNRIPGV PGSMPNASWT GNLRAIKWSD MEDRHGGCHG HYVHGICIYG NGDLKWLVNS  360
PSLFANKFEL NTYPLTVECL ELRHRERTLN QSETAIQPSW YF                     402
```